United States Patent
Gadjeva et al.

(10) Patent No.: US 12,428,417 B2
(45) Date of Patent: Sep. 30, 2025

(54) INHIBITORS OF MACROPHAGE MIGRATION INHIBITORY FACTOR

(71) Applicant: The Brigham and Women's Hospital, Inc., Boston, MA (US)

(72) Inventors: Mihaela Gadjeva, Cambridge, MA (US); Nikolay E. Nifantiev, Moscow (RU); Igor V. Zavarzin, Moscow (RU)

(73) Assignee: The Brigham and Women's Hospital, Inc., Boston, MA (US)

( * ) Notice: Subject to any disclaimer, the term of this patent is extended or adjusted under 35 U.S.C. 154(b) by 915 days.

(21) Appl. No.: 17/630,650

(22) PCT Filed: Jul. 27, 2020

(86) PCT No.: PCT/US2020/043693
§ 371 (c)(1),
(2) Date: Jan. 27, 2022

(87) PCT Pub. No.: WO2021/021706
PCT Pub. Date: Feb. 4, 2021

(65) Prior Publication Data
US 2022/0274981 A1    Sep. 1, 2022

(30) Foreign Application Priority Data

Jul. 29, 2019 (RU) .......................... RU2019123849

(51) Int. Cl.
*C07D 471/04*    (2006.01)
*A61K 31/437*    (2006.01)
(Continued)

(52) U.S. Cl.
CPC .......... *C07D 471/04* (2013.01); *A61K 31/437* (2013.01); *A61K 31/505* (2013.01); *A61P 33/06* (2018.01)

(58) Field of Classification Search
CPC .... A61K 31/437; A61K 31/505; A61K 45/06; A61P 33/06; Y02A 50/30; C07D 471/04
See application file for complete search history.

(56) References Cited

U.S. PATENT DOCUMENTS

| 10,077,265 | B2 | 9/2018 | Rohrig et al. |
| 2009/0047246 | A1 | 2/2009 | Beigelman et al. |
| 2017/0283412 | A1* | 10/2017 | Röhrig ................. C07D 471/04 |

FOREIGN PATENT DOCUMENTS

| JP | 2017-222626 | 12/2017 |
| WO | WO 2009/137500 | 11/2009 |

(Continued)

OTHER PUBLICATIONS

Buchko et al., "Sequence of GI-MIF and the other Crystal structure of a macrophage migration inhibitory factor from Giardia lamblia," J Struct Funct Genomics, Jun. 2013, 14 (2): 47-57.

(Continued)

*Primary Examiner* — Savitha M Rao
*Assistant Examiner* — Elena Vladimirovna Vishnyakova
(74) *Attorney, Agent, or Firm* — Fish & Richardson P.C.

(57) ABSTRACT

The present application provides a compound of Formula (I): [Formula I] or a pharmaceutically acceptable salt thereof, wherein $R^1$, $R^2$, $R^3$, $R^4$, $R^5$, $R^6$, W, L, $R^8$, and $R^9$ are as described herein. Pharmaceutical compositions including these compounds and methods of using these compounds for treating parasitic infections (e.g., malaria), cancer, cardiovascular diseases, neurological diseases, inflammatory diseases, neuropathic pain, and other conditions are also disclosed herein.

(Continued)

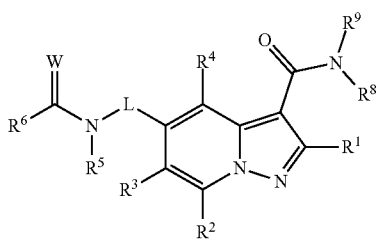

(I)

16 Claims, 2 Drawing Sheets

(51) Int. Cl.
*A61K 31/505* (2006.01)
*A61P 33/06* (2006.01)

(56) References Cited

FOREIGN PATENT DOCUMENTS

| WO | WO 2010/030538 | | 3/2010 | |
|----|----|----|----|----|
| WO | WO-2014078802 | A1 * | 5/2014 | ........... A61K 31/437 |
| WO | WO 2016/046158 | | 3/2016 | |
| WO | WO-2016046158 | A1 * | 3/2016 | ................ A61P 7/02 |
| WO | WO 2021/021706 | | 2/2021 | |

OTHER PUBLICATIONS

CAS Registry No. 1891071-12-7, "Carbamic acid, N-[3-[(dimethylamino)carbonyl]pyrazolo[1,5-a]pyridin-5-yl]-, 1,1-dimethylethyl ester," Apr. 15, 2016, 1 page.
CAS Registry No. 2170248-23-2, "Acetamide, N-[[3-[[4-(4-bromobenzoyl)-3-(4-chlorophenyl)-1-piperazinyl]carbonyl]pyrazolo[1,5-a]pyridin-5-yl]methyl," Jan. 11, 2018, 1 page.
Cho et al., "Allosteric inhibition of macrophage migration inhibitory factor revealed by ibudilast," Proc Natl Acad Sci., Jun. 2010, 107: 11313-11318.
Cooper et al., "The effects of ibudilast, a glial activation inhibitor, on opioid withdrawal symptoms in opioid-dependent volunteers," Addict Biol, Jul. 2016, 21 (4),895-903, 9 pages.
Cooper et al., "Effects of ibudilast on oxycodone-induced analgesia and subjective effects in opioid-dependent volunteers," Drug Alcohol Dependence, 2017, 178:340-347.
Fox et al., " Phase 2 Trial of Ibudilast in Progressive Multiple Sclerosis," The New England Journal of Medicine, Aug. 2018, 379(9):846-855.
Fox et al., "Design, rationale, and baseline characteristics of the randomized double-blind phase II clinical trial of ibudilast in progressive multiple sclerosis," Contemporary Clinical Trials, Sep. 2016, 50:166-177, 30 pages.
Holowka et al., "Leishmania-encoded orthologs of macrophage migration inhibitory factor regulate host immunity to promote parasite persistence," FASEB Journal, Jun. 2016, 30 (6):2249-2265.
International Search Report in International Appln. No. PCT/US2020/043693, dated Oct. 31, 2020, 4 pages.
Kamir et al., "A Leishmania ortholog of macrophage migration inhibitory factor modulates host macrophage responses," The Journal of Immunology, Apr. 2008, 180 (12):8250-8261.
Kawasaki et al., "Effect of ibudilast: a novel antiasthmatic agent, on airway hypersensitivity in bronchial asthma," Journal of Asthma 1992, 29 (4):245-252.
Kishi et al., "Ibudilast: a non-selective PDE inhibitor with multiple actions on blood cells and the vascular wall," Cardiovasc Drug Reviews, 2001, 19(3):215-225.
Leyton-Jaimes et al., "Macrophage migration inhibitory factor: A multifaceted cytokine implicated in multiple neurological diseases," Experimental Neurology, 2017, 301:83-91, 9 pages.
Liu et al., "Protective Effect Against Toxoplasmosis in BALB/c Mice Vaccinated with Toxoplasma gondii Macrophage Migration Inhibitory Factor," Frontiers in Microbiology, Apr. 2019, 10(813):1-10.
Metz et al., "Effects of Ibudilast on the Subjective, Reinforcing, and Analgesic Effects of Oxycodone in Recently Detoxified Adults with Opioid Dependence," Neuropsychopharmacology, May 2017, 42: 1825-1832.
Nobre et al., "Macrophage Migration Inhibitory Factor (MIF): Biological Activities and Relation with Cancer," Pathol. Oncol. Res., Apr. 2017, 23:235-244.
Pubchem.ncbi.nlm.nih.gov [online], "v 5-(Benzylamino)-N-methylpyrazolo[1,5-a]pyridine-3-carboxamide; CID 143956676. Pubchem entry," Dec. 2019, retrieved on Feb. 9, 2022, retrieved from URL <https://pubchem.ncbi.nlm.nih.gov/compound/143956676>, 7 pages.
Richardson et al., "Structual of Leishmania major orthologues of macrophage migration Inhibtory factor," Biochem Biophys Res Commun, 2009, 380(3): 442-448.
Schwenkgrub et al., "The phosphodiesterase inhibitor, ibudilast, attenuates neuroinflammation in the MPTP model of Parkinson's disease," PLoS One, Jul. 2017, 12(7), e0182019: 1-14.
Sparkes et al., "Reprint of: The non-mammalian MIF superfamily," Immunobiology, May 2017, 222 (3): 858-867.
Tilstam et al., "MIF family cytokines in cardiovascular diseases and prospects for precision-based therapeutics," Expert Opin Ther Targets, Jul. 2017, 21 (7):671-683, 27 pages.
Walters, "Neuroinflammatory contributions to pain after SCI: roles for central glial mechanisms and nociceptor-mediated host defense," Experimental Neurology, Feb. 2014, 258:48-61.
PCT International Preliminary Report on Patentability in International Appln. No. PCT/US2020/043693, dated Feb. 1, 2022, 8 pages.

* cited by examiner

INHIBITORS OF MACROPHAGE MIGRATION INHIBITORY FACTOR

CLAIM OF PRIORITY

This application is a national stage application under 35 USC § 371 of International Application No. PCT/US2020/043693, filed on Jul. 27, 2020, which claims the benefit of priority of Russian Application No. 2019123849, filed on Jul. 29, 2019, the entire contents of which are incorporated herein by reference.

TECHNICAL FIELD

This invention relates to organic compounds, and in particular to pyrazolo[1,5-a]pyridine derivatives that are inhibitors of macrophage migration inhibitory factor (MIF).

BACKGROUND

There are numerous deadly diseases affecting current human population. For example, in 2013, there were approximately 200 million clinical cases and 584,000 deaths from malaria caused by parasites of the genus *Plasmodium*. Likewise, cancer is one of the leading causes of death in contemporary society. The numbers of new cancer cases and deaths is increasing each year. Currently, cancer incidence is 454.8 cases of cancer per 100,000 men and women per year, while cancer mortality is 71.2 cancer deaths per 100,000 men and women per year. Additionally, inflammatory conditions and neurodegenerative diseases affect a significant segment of population, especially the elderly. For example, Alzheimer's disease (AD), a neurodegenerative disorder that affects approximately 44 million people world-wide, is the sixth leading cause of death with an estimated socioeconomic burden of more than $200 billion. Currently, there is no cure for any of these debilitating diseases, and new treatments are needed to combat them. The compounds and methods of the present disclosure help meet this need.

SUMMARY

In one general aspect, the present disclosure provides a compound of formula (I):

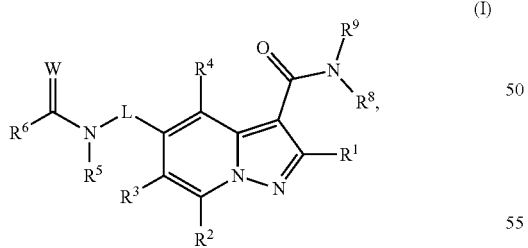

or a pharmaceutically acceptable salt thereof, wherein $R^1$, $R^2$, $R^3$, $R^4$, $R^5$, $R^6$, W, L, $R^8$, and $R^9$ are as described herein.

In another general aspect, the present disclosure provides a pharmaceutical composition comprising a compound of Formula (I), or a pharmaceutically acceptable salt thereof, and a pharmaceutically acceptable carrier.

In yet another general aspect, the present disclosure provides a method selected from:
modulating an activity of a macrophage migration inhibitory factor (MIF) in a cell;
modulating a parasite-induced pathology in a cell;
modulating invasiveness of a parasite in a cell;
modulating a parasite infection in a cell; and
modulating an egress of a parasite from a cell;
the method comprising contacting the cell with an effective amount of a compound of Formula (I), or a pharmaceutically acceptable salt thereof, or a pharmaceutical composition comprising same.

In yet another general aspect, the present disclosure provides a method of treating or preventing a disease or condition selected from:
parasitemia,
parasitic infection (e.g., malaria, malarial anemia, leishmaniasis, toxoplasmosis, giardiasis, or trypanosomiasis),
neurological disease or condition,
cancer,
neuropathic pain,
inflammatory disease or condition, and
cardiovascular disease or condition,
the method comprising administering to a subject in need thereof a therapeutically effective amount of a compound or Formula (I), or a pharmaceutically acceptable salt thereof, of a pharmaceutical composition comprising same.

In yet another general aspect, the present disclosure provides a method selected from:
modulating an activity of a macrophage migration inhibitory factor (MIF) in a cell;
modulating a parasite-induced pathology in a cell;
modulating invasiveness of a parasite in a cell;
modulating a parasite infection in a cell; and
modulating an egress of a parasite from a cell;
the method comprising contacting the cell with an effective amount of a compound selected from:

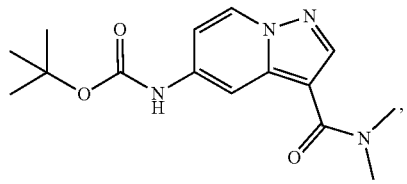

, and

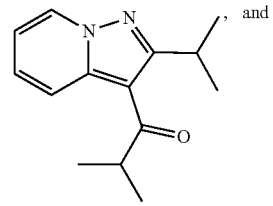

(ibudilast)

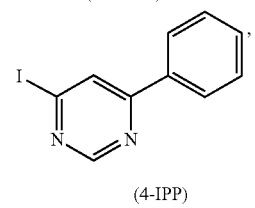

(4-IPP)

or a pharmaceutically acceptable salt thereof, or a pharmaceutical composition comprising same.

In yet another general aspect, the present disclosure provides a method of treating or preventing a disease or condition selected from:

parasitemia, parasitic infection (e.g., malaria, malarial anemia, leishmaniasis, toxoplasmosis, giardiasis, or trypanosomiasis), neurological disease or condition, cancer, neuropathic pain, inflammatory disease or condition, and cardiovascular disease or condition, the method comprising administering to a subject in need thereof a therapeutically effective amount of a compound selected from:

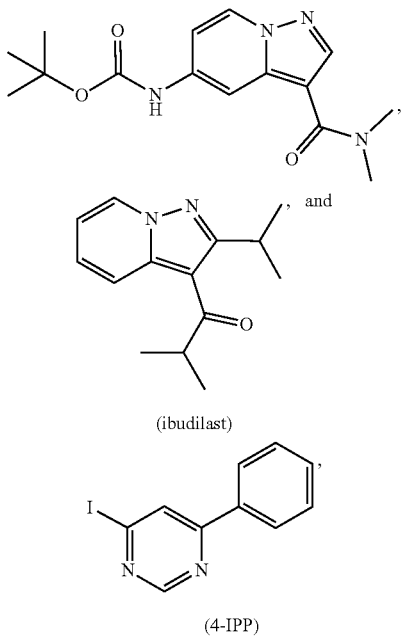

(ibudilast)

(4-IPP)

or a pharmaceutically acceptable salt thereof, of a pharmaceutical composition comprising same.

Unless otherwise defined, all technical and scientific terms used herein have the same meaning as commonly understood by one of ordinary skill in the art to which the present application belongs. Methods and materials are described herein for use in the present application; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the present application will be apparent from the following detailed description and figures, and from the claims.

DETAILED DESCRIPTION

Figure 1:
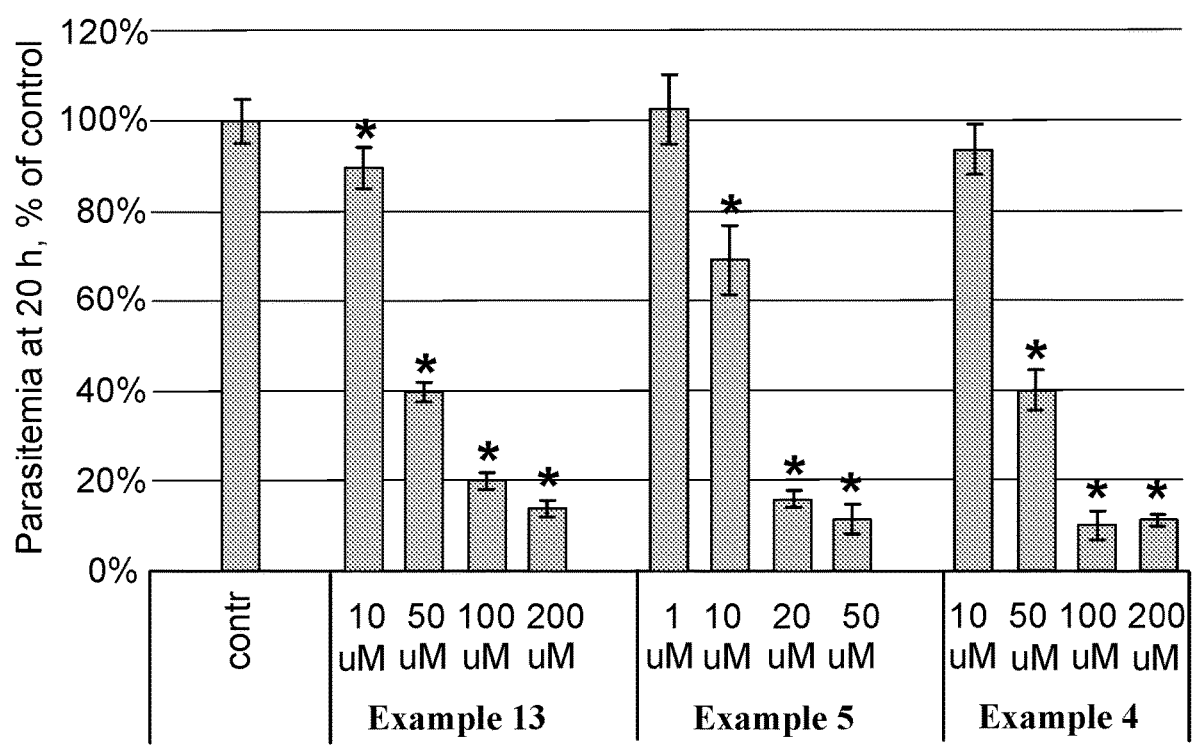
FIG. 1 contains a bar graph showing results of invasion assay for compounds of Examples 4, 5, and 13.

Finding an effective therapeutic to treat, e.g., malaria and, eventually, to eliminate the spread of the parasite is a long-standing and difficult human health challenge. The parasite is easily transmitted (e.g., by mosquitoes in case of malaria), multiplies rapidly, and readily develops resistance to drugs. The present disclosure provides compounds and pharmaceutical compositions containing these compounds that are useful in methods of treating or preventing, e.g., malaria. Certain embodiments of these compounds, compositions, and methods are described herein.

Therapeutic Molecules

In some embodiments, the present disclosure provides a compound of formula (I):

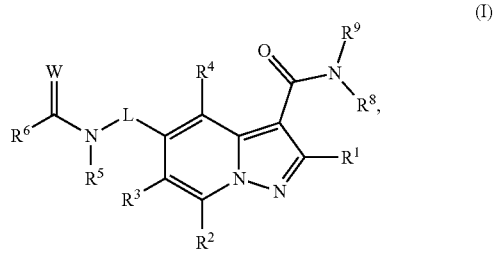

(I)

or a pharmaceutically acceptable salt thereof, wherein:

$R^1$, $R^2$, $R^3$, and $R^4$ are each independently selected from H, halo, CN, $NO_2$, $C_{1-6}$ alkyl, $C_{1-6}$ haloalkyl, $C_{2-6}$ alkenyl, $C_{2-6}$ alkynyl, $OR^{a1}$, $C(O)R^{b1}$, $C(O)NR^{c1}R^{d1}$, $C(O)OR^{a1}$, $NR^{c1}R^{d1}$, $NR^{c1}C(O)R^{b1}$, $NR^{c1}C(O)OR^{a1}$, $NR^{c1}S(O)_2R^{b1}$, $S(O)_2R^{b1}$, and $S(O)_2NR^{c1}R^{d1}$; wherein said $C_{1-6}$ alkyl, $C_{2-6}$ alkenyl, and $C_{2-6}$ alkynyl are each optionally substituted with 1, 2, or 3 substituents independently selected from CN, $NO_2$, $OR^{a1}$, $C(O)R^{b1}$, $C(O)NR^{c1}R^{d1}$, $C(O)OR^{a1}$, $NR^{c1}R^{d1}$, $NR^{c1}C(O)R^{b1}$, $NR^{c1}C(O)OR^{a1}$, $NR^{c1}S(O)_2R^{b1}$, $S(O)_2R^{b1}$, and $S(O)_2NR^{c1}R^{d1}$;

L is selected from $C_{1-3}$ alkylene, $C_{2-4}$ alkenylene, and $C_{2-4}$ alkynylene, each of which is optionally substituted with 1, 2, or 3 substituents independently selected from OH, $NO_2$, CN, halo, $C_{1-6}$ alkoxy, and $C_{1-6}$ haloalkoxy;

$R^6$ is selected from Cy and X-Cy;

X is selected from O, S, and $NR^7$;

$R^5$, $R^7$, and $R^8$ are each independently selected from H and $C_{1-3}$ alkyl;

W is selected from O and S;

$R^9$ is selected from $C_{1-6}$ alkyl, $C_{1-6}$ haloalkyl, $C_{2-6}$ alkenyl, $C_{2-6}$ alkynyl, $Cy^1$, $C(O)R^{b1}$, $C(O)NR^{c1}R^{d1}$, $C(O)OR^{a1}$, $S(O)_2R^{b1}$, and $S(O)_2NR^{c1}R^{d1}$, wherein said $C_{1-6}$ alkyl, $C_{2-6}$ alkenyl, and $C_{2-6}$ alkynyl are each optionally substituted with 1, 2, or 3 substituents independently selected from $Cy^1$, CN, $NO_2$, $OR^{a1}$, $C(O)R^{b1}$, $C(O)NR^{c1}R^{d1}$, $C(O)OR^{a1}$, $NR^{c1}R^{d1}$, $NR^{c1}C(O)R^{b1}$, $NR^{c1}C(O)OR^{a1}$, $NR^{c1}S(O)_2R^{b1}$, $S(O)_2R^{b1}$, and $S(O)_2NR^{c1}R^{d1}$;

or $R^8$ and $R^9$, together with the N atom to which they are attached, form a 4-10 membered heterocycloalkyl ring, which is optionally substituted with 1, 2, or 3 substituents independently selected from $R^{Cy1}$;

Cy is selected from $C_{6-10}$ aryl, $C_{3-10}$ cycloalkyl, 5-14 membered heteroaryl, and 4-10 membered heterocycloalkyl, each of which is optionally substituted with 1, 2, or 3 substituents independently selected from $R^{Cy1}$;

$Cy^1$ is selected from $C_{6-10}$ aryl, $C_{3-10}$ cycloalkyl, 5-14 membered heteroaryl, and 4-10 membered heterocycloalkyl, each of which is optionally substituted with 1, 2, or 3 substituents independently selected from $R^{Cy1}$;

each $R^{Cy1}$ is independently selected from halo, CN, $NO_2$, $Cy^2$, $C_{1-6}$ alkyl, $C_{1-6}$ haloalkyl, $C_{2-6}$ alkenyl, $C_{2-6}$ alkynyl, $OR^{a2}$, $SR^{a2}$, $C(O)R^{b2}$, $C(O)NR^{c2}R^{d2}$, $C(O)OR^{a2}$, $NR^{c2}R^{d2}$, $NR^{c2}C(O)R^{b2}$, $NR^{c2}C(O)OR^{a2}$, $NR^{c2}S(O)_2R^{b2}$, $S(O)_2R^{b2}$, and $S(O)_2NR^{c2}R^{d2}$; wherein said $C_{1-6}$ alkyl, $C_{2-6}$ alkenyl, and $C_{2-6}$ alkynyl are each optionally substituted with 1, 2, or 3 substituents independently selected from $Cy^2$, halo, CN, $NO_2$, $OR^{a2}$, $C(O)R^{b2}$, $C(O)NR^{c2}R^{d2}$, $C(O)OR^{a2}$, $NR^{c2}R^{d2}$, $NR^{c2}C(O)R^{b2}$, $NR^{c2}C(O)OR^{a2}$, $NR^{c2}S(O)_2R^{b2}$, $S(O)_2R^{b2}$, and $S(O)_2NR^{c2}R^{d2}$;

each $Cy^2$ is independently selected from $C_{6-10}$ aryl, $C_{3-10}$ cycloalkyl, 5-10 membered heteroaryl, and 4-10 membered heterocycloalkyl, each of which is optionally substituted with 1, 2, or 3 substituents independently selected from $R^{Cy2}$;

each $R^{Cy2}$ is independently selected from halo, CN, $NO_2$, $C_{1-6}$ alkyl, $C_{1-6}$ haloalkyl, $C_{2-6}$ alkenyl, $C_{2-6}$ alkynyl, $OR^{a2}$, $C(O)R^{b2}$, $C(O)NR^{c2}R^{d2}$, $C(O)OR^{a2}$, $NR^{c2}R^{a2}$, $NR^{c2}C(O)R^{b2}$, $NR^{c2}C(O)OR^{a2}$, $NR^{c2}S(O)_2R^{b2}$, $S(O)_2R^{b2}$, and $S(O)_2NR^{c2}R^{d2}$; wherein said $C_{1-6}$ alkyl, $C_{2-6}$ alkenyl, and $C_{2-6}$ alkynyl are each optionally substituted with 1, 2, or 3 substituents independently selected from halo, CN, $NO_2$, $OR^{a2}$, $C(O)R^{b2}$, $C(O)NR^{c2}R^{d2}$, $C(O)OR^{a2}$, $NR^{c2}R^{a2}$, $NR^{c2}C(O)R^{b2}$, $NR^{c2}C(O)OR^{a2}$, $NR^{c2}S(O)_2R^{b2}$, $S(O)_2R^{b2}$, and $S(O)_2NR^{c2}R^{d2}$;

each $R^{a1}$, $R^{b1}$, $R^{c1}$, $R^{d1}$, $R^{a2}$, $R^{b2}$, $R^{c2}$, and $R^{d2}$ is independently selected from H, $C_{1-6}$ alkyl, $C_{1-4}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkylene, $C_{3-10}$ cycloalkyl-$C_{1-4}$ alkylene, (5-10 membered heteroaryl)-$C_{1-4}$ alkylene, and (4-10 membered heterocycloalkyl)-$C_{1-4}$ alkylene, wherein said $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkylene, $C_{3-10}$ cycloalkyl-$C_{1-4}$ alkylene, (5-10 membered heteroaryl)-$C_{1-4}$ alkylene, and (4-10 membered heterocycloalkyl)-$C_{1-4}$ alkylene are each optionally substituted with 1, 2, 3, 4, or 5 substituents independently selected from $R^g$;

or any $R^{c1}$ and $R^{d1}$ together with the N atom to which they are attached form a 4-7 membered heterocycloalkyl, which is optionally substituted with 1, 2, or 3 substituents independently selected from $R^g$;

or any $R^{c2}$ and $R^{d2}$ together with the N atom to which they are attached form a 4-7 membered heterocycloalkyl, which is optionally substituted with 1, 2, or 3 substituents independently selected from $R^g$; and each $R^g$ is independently selected from OH, $NO_2$, CN, halo, $C_{1-6}$ alkyl, $C_{2-6}$ alkenyl, $C_{2-6}$ alkynyl, $C_{1-4}$ haloalkyl, $C_{1-6}$ alkoxy, $C_{1-6}$ haloalkoxy, cyano-$C_{1-3}$ alkylene, HO—$C_{1-3}$ alkylene, $C_{6-10}$ aryl, $C_{6-10}$ aryloxy, $C_{3-10}$ cycloalkyl, 5-10 membered heteroaryl, 4-10 membered heterocycloalkyl, $C_{6-10}$ aryl-$C_{1-4}$ alkylene, $C_{3-10}$ cycloalkyl-$C_{1-4}$ alkylene, (5-10 membered heteroaryl)-$C_{1-4}$ alkylene, (4-10 membered heterocycloalkyl)-$C_{1-4}$ alkylene, amino, $C_{1-6}$ alkylamino, di($C_{1-6}$ alkyl)amino, thio, $C_{1-6}$ alkylthio, $C_{1-6}$ alkylsulfinyl, $C_{1-6}$ alkylsulfonyl, carbamyl, $C_{1-6}$ alkylcarbamyl, di($C_{1-6}$ alkyl)carbamyl, carboxy, $C_{1-6}$ alkylcarbonyl, $C_{1-6}$ alkoxycarbonyl, $C_{1-6}$ alkylcarbonylamino, $C_{1-6}$ alkylsulfonylamino, aminosulfonyl, $C_{1-6}$ alkylaminosulfonyl, di($C_{1-6}$ alkyl)aminosulfonyl, aminosulfonylamino, $C_{1-6}$ alkylaminosulfonylamino, di($C_{1-6}$ alkyl)aminosulfonylamino, aminocarbonylamino, $C_{1-6}$ alkylaminocarbonylamino, and di($C_{1-6}$ alkyl)aminocarbonylamino.

In some embodiments, X is O.

In some embodiments, X is S.

In some embodiments, X is $NR^7$.

In some embodiments, $R^7$ is H.

In some embodiments, X is NH.

In some embodiments, $R^1$, $R^2$, $R^3$, and $R^4$ are each independently selected from H, halo, CN, $NO_2$, $C_{1-6}$ alkyl, $C_{1-6}$ haloalkyl, OH, $C_{1-6}$ alkoxy, $C_{1-6}$ haloalkoxy, $C(O)R^{b1}$, $C(O)NR^{c1}R^{d1}$, $C(O)OR^{a1}$, $NR^{c1}R^{d1}$, and $NR^{c1}C(O)R^{b1}$; wherein said $C_{1-6}$ alkyl is optionally substituted with 1, 2, or 3 substituents independently selected from CN, $NO_2$, OH, $C_{1-6}$ alkoxy, $C(O)R^{b1}$, $C(O)NR^{c1}R^{d1}$, $C(O)OR^{a1}$, $NR^{c1}R^{d1}$, and $NR^{c1}C(O)R^{b1}$.

In some embodiments, $R^1$, $R^2$, $R^3$, and $R^4$ are each independently selected from H, halo, $C_{1-6}$ alkyl, $C_{1-6}$ haloalkyl, $C_{1-6}$ alkoxy, and $C_{1-6}$ haloalkoxy.

In some embodiments, $R^1$, $R^2$, $R^3$, and $R^4$ are each independently selected from H, halo, $C_{1-6}$ alkyl, and $C_{1-6}$ alkoxy.

In some embodiments, $R^1$, $R^2$, $R^3$, and $R^4$ are each independently selected from H and $C_{1-6}$ alkyl.

In some embodiments, $R^1$, $R^2$, $R^3$, and $R^4$ are each H.

In some embodiments, L is $C_{1-6}$ alkylene, which is optionally substituted with 1, 2, or 3 substituents selected from OH, $NO_2$, CN, halo, $C_{1-6}$ alkoxy, and $C_{1-6}$ haloalkoxy.

In some embodiments, L is $C_{1-6}$ alkylene (e.g., methylene, ethylene, or propylene), which is optionally substituted with 1, 2, or 3 halo.

In some embodiments, L is $C_{1-6}$ alkylene (methylene, ethylene, or propylene), which is optionally substituted with $C_{1-6}$ alkoxy or $C_{1-6}$ haloalkoxy.

In some embodiments, L is $C_{1-3}$ alkylene.

In some embodiments, L is selected from methylene, ethylene, and propylene.

In some embodiments, L is methylene.

In some embodiments, $R^5$ is H.

In some embodiments, W is O.

In some embodiments, W is S.

In some embodiments, Cy is selected from $C_{6-10}$ aryl and $C_{3-10}$ cycloalkyl, each of which is optionally substituted with 1, 2, or 3 substituents independently selected from $R^{Cy1}$.

In some embodiments, Cy is $C_{6-10}$ aryl (e.g., phenyl or naphthyl), optionally substituted with 1, 2, or 3 substituents independently selected from $R^{Cy1}$.

In some embodiments, Cy is $C_{3-10}$ cycloalkyl (e.g., cyclopropyl, cyclobutyl, cyclopentyl, or cyclohexyl), optionally substituted with 1, 2, or 3 substituents independently selected from $R^{Cy1}$.

In some embodiments, Cy is phenyl or cycloalkyl, each of which is optionally substituted with 1, 2, or 3 substituents independently selected from $R^{Cy1}$.

In some embodiments, Cy is phenyl, optionally substituted with 1, 2, or 3 substituents independently selected from $R^{Cy1}$.

In some embodiments, Cy is cyclopropyl, optionally substituted with 1, 2, or 3 substituents independently selected from $R^{Cy1}$.

In some embodiments, $R^8$ is H.

In some embodiments, $R^8$ is $C_{1-6}$ alkyl.

In some embodiments, $R^9$ is selected from $C_{1-6}$ alkyl and $Cy^1$, wherein said $C_{1-6}$ alkyl is optionally substituted with 1, 2, or 3 substituents independently selected from $Cy^1$, CN, $NO_2$, $OR^{a1}$, $C(O)R^{b1}$, $C(O)NR^{c1}R^{d1}$, $C(O)OR^{a1}$, $NR^{c1}R^{d1}$, $NR^{c1}C(O)R^{b1}$, $NR^{c1}C(O)OR^{a1}$, $NR^{c1}S(O)_2R^{b1}$, $S(O)_2R^{b1}$, and $S(O)_2NR^{c1}R^{d1}$.

In some embodiments, $R^9$ is selected from $C_{1-6}$ alkyl and $Cy^1$, wherein said $C_{1-6}$ alkyl is optionally substituted with $Cy^1$ or $NR^{c1}R^{d1}$.

In some embodiments, $R^9$ is $Cy^1$.

In some embodiments, $R^9$ is $C_{1-6}$ alkyl, which is optionally substituted with 1, 2, or 3 substituents independently selected from $Cy^1$, CN, $NO_2$, $OR^{a1}$, $C(O)R^{b1}$, $C(O)NR^{c1}R^{d1}$, $C(O)OR^{a1}$, $NR^{c1}R^{d1}$, $NR^{c1}C(O)R^{b1}$, $NR^{c1}C(O)OR^{a1}$, $NR^{c1}S(O)_2R^{b1}$, $S(O)_2R^{b1}$, and $S(O)_2NR^{c1}R^{d1}$.

In some embodiments, $R^9$ is $C_{1-6}$ alkyl, optionally substituted with $Cy^1$ or $NR^{c1}R^{d1}$.

In some embodiments, $R^9$ is $C_{1-6}$ alkyl substituted with $Cy^1$.

In some embodiments, $R^9$ is $C_{1-6}$ alkyl substituted with $NR^{c1}R^{d1}$.

In some embodiments, $Cy^1$ is selected from $C_{6-10}$ aryl, 5-14 membered heteroaryl, and 4-10 membered heterocycloalkyl, each of which is optionally substituted with 1, 2, or 3 substituents independently selected from $R^{Cy1}$.

In some embodiments, $Cy^1$ is $C_{6-10}$ aryl, optionally substituted with 1, 2, or 3 independently selected $R^{Cy1}$.

In some embodiments, $Cy^1$ is 5-10 membered heteroaryl, optionally substituted with 1, 2, or 3 independently selected $R^{Cy1}$.

In some embodiments, $Cy^1$ is 4-10 membered heterocycloalkyl, optionally substituted with 1, 2, or 3 independently selected $R^{Cy1}$.

In some embodiments, $Cy^1$ is selected from phenyl, piperidine, pyridine, and pyrrolidone, each of which is optionally substituted with 1, 2, or 3 independently selected $R^{Cy1}$.

In some embodiments, $Cy^1$ is selected from phenyl, piperidine, pyridine, and pyrrolidone, each of which is optionally substituted with 1, 2, or 3 independently selected $R^{Cy1}$.

In some embodiments, $Cy^1$ is phenyl, optionally substituted with 1, 2, or 3 independently selected $R^{Cy1}$.

In some embodiments, $Cy^1$ is piperidine, optionally substituted with 1, 2, or 3 independently selected $R^{Cy1}$.

In some embodiments, $Cy^1$ is pyridine, optionally substituted with 1, 2, or 3 independently selected $R^{Cy1}$.

In some embodiments, $Cy^1$ is pyrrolidone, optionally substituted with 1, 2, or 3 independently selected $R^{Cy1}$.

In some embodiments, $R^9$ is $C_{1-6}$ alkyl substituted with phenyl, pyridine, or pyrrolidone, each of which is optionally substituted with 1, 2, or 3 independently selected $R^{Cy1}$.

In some embodiments, $R^9$ is $C_{1-6}$ alkyl substituted with phenyl or pyridine, each of which is optionally substituted with 1, 2, or 3 independently selected $R^{Cy1}$.

In some embodiments, $R^9$ is piperidine, optionally substituted with 1, 2, 3, 4, or 5 independently selected $R^{Cy1}$.

In some embodiments, $R^8$ and $R^9$, together with the N atom to which they are attached, form a 5-10-membered heterocycloalkyl ring, which is optionally substituted with 1, 2, or 3 substituents independently selected from $R^{Cy1}$.

In some embodiments, $R^8$ and $R^9$, together with the N atom to which they are attached, form a heterocycloalkyl ring selected from piperidine, piperazine, tetrahydroisoquinoline, and pyrrolidine, each of which is optionally substituted with 1, 2, or 3 independently selected $R^{Cy1}$.

In some embodiments, $R^8$ and $R^9$, together with the N atom to which they are attached, form piperidine, which is optionally substituted with 1, 2, or 3 independently selected $R^{Cy1}$.

In some embodiments, $R^8$ and $R^9$, together with the N atom to which they are attached, form piperazine, which is optionally substituted with 1, 2, or 3 independently selected $R^{Cy1}$.

In some embodiments, $R^8$ and $R^9$, together with the N atom to which they are attached, form tetrahydroisoquinoline, which is optionally substituted with 1, 2, or 3 independently selected $R^{Cy1}$.

In some embodiments, $R^8$ and $R^9$, together with the N atom to which they are attached, form pyrrolidine, which is optionally substituted with 1, 2, or 3 independently selected $R^{Cy1}$.

In some embodiments, $R^{Cy1}$ is selected from halo, CN, OH, $NO_2$, $Cy^2$, $C_{1-6}$ alkyl, $C_{1-6}$ haloalkyl, $C_{1-6}$ alkoxy, $C_{1-6}$ haloalkoxy, $C(O)R^{b2}$, $C(O)NR^{c2}R^{d2}$, $C(O)OR^{a2}$, and $NR^{c2}R^{d2}$, wherein said $C_{1-6}$ alkyl is optionally substituted with 1, 2, or 3 substituents independently selected from $Cy^2$, halo, CN, OH, $NO_2$, $C_{1-6}$ haloalkyl, $C_{1-6}$ alkoxy, and $C_{1-6}$ haloalkoxy.

In some embodiments, $R^{Cy1}$ is selected from halo, $Cy^2$, $C_{1-6}$ alkyl, $C(O)R^{b2}$, $C(O)NR^{c2}R^{d2}$, $NR^{c2}R^{d2}$, wherein said $C_{1-6}$ alkyl is optionally substituted with $Cy^2$.

In some embodiments, $R^{Cy1}$ is selected from halo, $C_{1-6}$ alkyl, and $NR^{c2}R^{d2}$.

In some embodiments, $R^{Cy1}$ is selected from $Cy^2$, $C_{1-6}$ alkyl, $C(O)R^{b2}$, and $C(O)NR^{c2}R^{d2}$, wherein said $C_{1-6}$ alkyl is optionally substituted with $Cy^2$.

In some embodiments, $R^{Cy1}$ is $C_{1-6}$ alkyl substituted with $Cy^2$.

In some embodiments, $R^{Cy1}$ is $Cy^2$.

In some embodiments, $R^{Cy1}$ is $C(O)R^{b2}$.

In some embodiments, $R^{Cy1}$ is $C(O)NR^{c2}R^{d2}$.

In some embodiments, $Cy^2$ is selected from $C_{6-10}$ aryl, 5-10 membered heteroaryl, and 4-10 membered heterocycloalkyl, each of which is optionally substituted with 1, 2, or 3 substituents independently selected from $R^{Cy2}$.

In some embodiments, $Cy^2$ is $C_{6-10}$ aryl, optionally substituted with 1, 2, or 3 substituents independently selected from $R^{Cy2}$.

In some embodiments, $Cy^2$ is selected from phenyl, piperidine, benzoisothiazole, and benzodioxole, each of which is optionally substituted with 1, 2, or 3 independently selected $R^{Cy2}$.

In some embodiments, $R^{Cy2}$ is selected from halo, CN, $NO_2$, $C_{1-6}$ alkyl, $C_{1-6}$ haloalkyl, and $OR^{a2}$.

In some embodiments, $R^{Cy2}$ is selected from halo, $C_{1-6}$ alkyl, and OH.

In some embodiments, $R^{a1}$, $R^{b1}$, $R^{c1}$, $R^{d1}$, $R^{a2}$, $R^{b2}$, $R^{c2}$, and $R^{d2}$ are each independently selected from H, $C_{1-6}$ alkyl, $C_{1-4}$ haloalkyl, $C_{6-10}$ aryl, $C_{3-10}$ cycloalkyl, 5-10 membered heteroaryl, and 4-10 membered heterocycloalkyl, each of which is optionally substituted with 1, 2, or 3 independently selected $R^g$.

In some embodiments, $R^g$ is selected from OH, $NO_2$, CN, halo, $C_{1-6}$ alkyl, $C_{1-4}$ haloalkyl, $C_{1-6}$ alkoxy, $C_{1-6}$ haloalkoxy, amino, $C_{1-6}$ alkylamino, di($C_{1-6}$ alkyl)amino, carboxy, carbamyl, $C_{1-6}$ alkylcarbonyl, and $C_{1-6}$ alkoxycarbonyl.

In some embodiments:
$R^1$, $R^2$, $R^3$, and $R^4$ are each independently selected from H, halo, CN, $NO_2$, $C_{1-6}$ alkyl, $C_{1-6}$ haloalkyl, OH, $C_{1-6}$ alkoxy, $C_{1-6}$ haloalkoxy, $C(O)R^{b1}$, $C(O)NR^{c1}R^{d1}$, $C(O)OR^{a1}$, $NR^{c1}R^{d1}$, and $NR^{c1}C(O)R^{b1}$, wherein said $C_{1-6}$ alkyl is optionally substituted with 1, 2, or 3 substituents independently selected from CN, NO$_2$, OH, C$_{1-6}$ alkoxy, C(O)R$^{b1}$, C(O)NR$^{c1}$R$^{d1}$, C(O)OR$^{a1}$, NR$^{c1}$R$^{d1}$, and NR$^{c1}$C(O)R$^{b1}$;

L is C$_{1-6}$ alkylene, which is optionally substituted with 1, 2, or 3 substituents selected from OH, NO$_2$, CN, halo, C$_{1-6}$ alkoxy, and C$_{1-6}$ haloalkoxy;

R$^5$ is H;

Cy is selected from C$_{6-10}$ aryl and C$_{3-10}$ cycloalkyl, each of which is optionally substituted with 1, 2, or 3 substituents independently selected from R$^{Cy1}$;

R$^8$ is H;

R$^9$ is selected from C$_{1-6}$ alkyl and Cy$^1$, wherein said C$_{1-6}$ alkyl is optionally substituted with 1, 2, or 3 substituents independently selected from Cy$^1$, CN, NO$_2$, OR$^{a1}$, C(O)R$^{b1}$, C(O)NR$^{c1}$R$^{d1}$, C(O)OR$^{a1}$, NR$^{c1}$R$^{d1}$, NR$^{c1}$C(O)R$^{b1}$, NR$^{c1}$C(O)OR$^{a1}$, NR$^{c1}$S(O)$_2$R$^{b1}$, S(O)$_2$R$^{b1}$, and S(O)$_2$NR$^{c1}$R$^{d1}$; or R$^8$ and R$^9$, together with the N atom to which they are attached, form a 5-10-membered heterocycloalkyl ring, which is optionally substituted with 1, 2, or 3 substituents independently selected from R$^{Cy1}$;

Cy$^1$ is selected from C$_{6-10}$ aryl, 5-14 membered heteroaryl, and 4-10 membered heterocycloalkyl, each of which is optionally substituted with 1, 2, or 3 substituents independently selected from R$^{Cy1}$;

R$^{Cy1}$ is selected from halo, CN, OH, NO$_2$, Cy$^2$, C$_{1-6}$ alkyl, C$_{1-6}$ haloalkyl, C$_{1-6}$ alkoxy, C$_{1-6}$ haloalkoxy, C(O)R$^{b2}$, C(O)NR$^{c2}$R$^{d2}$, C(O)OR$^{a2}$, and NR$^{c2}$R$^{d2}$, wherein said C$_{1-6}$ alkyl is optionally substituted with 1, 2, or 3 substituents independently selected from Cy$^2$, halo, CN, OH, NO$_2$, C$_{1-6}$ haloalkyl, C$_{1-6}$ alkoxy, and C$_{1-6}$ haloalkoxy;

Cy$^2$ is selected from C$_{6-10}$ aryl, 5-10 membered heteroaryl, and 4-10 membered heterocycloalkyl, each of which is optionally substituted with 1, 2, or 3 substituents independently selected from R$^{Cy2}$;

R$^{Cy2}$ is selected from halo, CN, NO$_2$, C$_{1-6}$ alkyl, C$_{1-6}$ haloalkyl, and OR$^{a2}$;

R$^{a1}$, R$^{b1}$, R$^d$, R$^{a1}$, R$^{a2}$, R$^{b2}$, R$^{c2}$, and R$^{d2}$ are each independently selected from H, C$_{1-6}$ alkyl, C$_{1-4}$ haloalkyl, C$_{6-10}$ aryl, C$_{3-10}$ cycloalkyl, 5-10 membered heteroaryl, and 4-10 membered heterocycloalkyl, each of which is optionally substituted with 1, 2, or 3 independently selected R$^g$; and R$^g$ is selected from OH, NO$_2$, CN, halo, C$_{1-6}$ alkyl, C$_{1-4}$ haloalkyl, C$_{1-6}$ alkoxy, C$_{1-6}$ haloalkoxy, amino, C$_{1-6}$ alkylamino, di(C$_{1-6}$ alkyl)amino, carboxy, carbamyl, C$_{1-6}$ alkylcarbonyl, and C$_{1-6}$ alkoxycarbonyl.

In some embodiments:

R$^1$, R$^2$, R$^3$, and R$^4$ are each independently selected from H, halo, C$_{1-6}$ alkyl, C$_{1-6}$ haloalkyl, C$_{1-6}$ alkoxy, and C$_{1-6}$ haloalkoxy;

L is C$_{1-3}$ alkylene;

R$^9$ is selected from C$_{1-6}$ alkyl and Cy$^1$, wherein said C$_{1-6}$ alkyl is optionally substituted with Cy$^1$ or NR$^{c1}$R$^{d1}$; or R$^{Cy1}$ is selected from halo, Cy$^2$, C$_{1-6}$ alkyl, C(O)R$^{b2}$, C(O)NR$^{c2}$R$^2$, NR$^{c2}$R$^2$ wherein said C$_{1-6}$ alkyl is optionally substituted with Cy$^2$; and R$^{Cy2}$ is selected from halo, C$_{1-6}$ alkyl, and OH.

In some embodiments:

Cy is selected from C$_{6-10}$ aryl and C$_{3-10}$ cycloalkyl, each of which is optionally substituted with 1, 2, or 3 substituents independently selected from halo, C$_{1-6}$ alkyl, and NR$^{c2}$R$^{d2}$.

R$^8$ and R$^9$, together with the N atom to which they are attached, form a 5-10-membered heterocycloalkyl ring, which is optionally substituted with 1, 2, or 3 substituents independently selected from Cy$^2$, C$_{1-6}$ alkyl, C(O)R$^{b2}$, and C(O)NR$^{c2}$R$^{d2}$, wherein said C$_{1-6}$ alkyl is optionally substituted with Cy$^2$.

In some embodiments:

R$^1$, R$^2$, R$^3$, and R$^4$ are each H;

L is methylene;

Cy is selected from phenyl and cyclopropyl, each of which is optionally substituted with 1, 2, or 3 substituents independently selected from halo, C$_{1-6}$ alkyl, and NR$^{c2}$R$^{d2}$;

Cy$^1$ is selected from phenyl, piperidine, pyridine, and pyrrolidone, each of which is optionally substituted with C$_{1-6}$ alkyl;

R$^8$ and R$^9$, together with the N atom to which they are attached, form a heterocycloalkyl ring selected from piperidine, piperazine, tetrahydroisoquinoline, and pyrrolidine, each of which is optionally substituted with 1, 2, or 3 substituents independently selected from Cy$^2$, C$_{1-6}$ alkyl, C(O)R$^{b2}$, and C(O)NR$^{c2}$R$^{d2}$, wherein said C$_{1-6}$ alkyl is optionally substituted with Cy$^2$; and Cy$^2$ is selected from phenyl, piperidine, benzoisothiazole, and benzodioxole, each of which is optionally substituted with 1, 2, or 3 independently selected R$^{Cy2}$.

In some embodiments, the compound of Formula (I) has Formula (Ia):

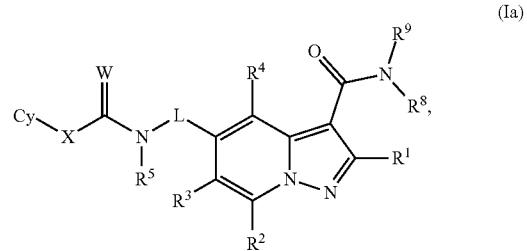

(Ia)

or a pharmaceutically acceptable salt thereof.

In some embodiments, the compound of Formula (I) has Formula (Ib):

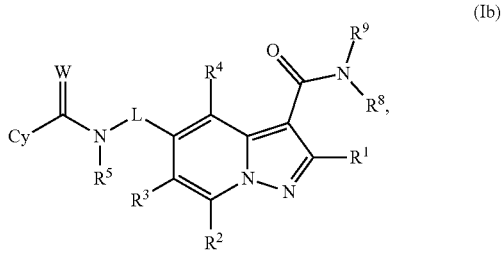

(Ib)

or a pharmaceutically acceptable salt thereof.

In some embodiments, the compound of Formula (I) has Formula (Ic):

(Ic)

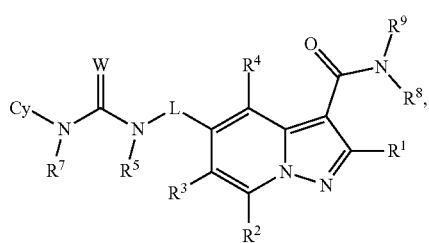

or a pharmaceutically acceptable salt thereof.

In some embodiments, the compound of Formula (I) has formula:

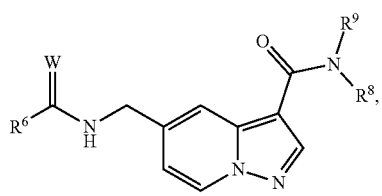

or a pharmaceutically acceptable salt thereof.

In some embodiments, the compound of Formula (I) has formula:

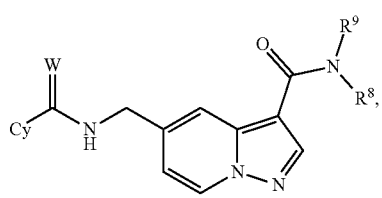

or a pharmaceutically acceptable salt thereof.

In some embodiments, the compound of Formula (I) has formula:

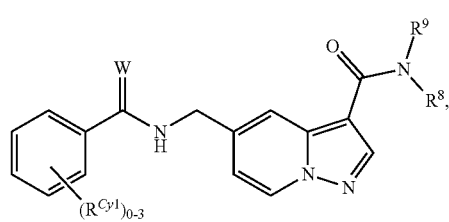

or a pharmaceutically acceptable salt thereof.

In some embodiments, the compound of Formula (I) has formula:

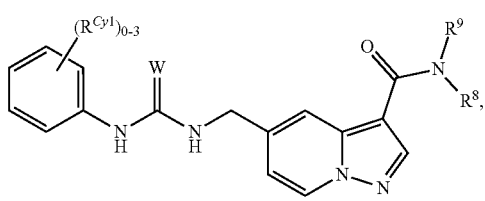

or a pharmaceutically acceptable salt thereof.

In some embodiments, the compound of Formula (I) has formula:

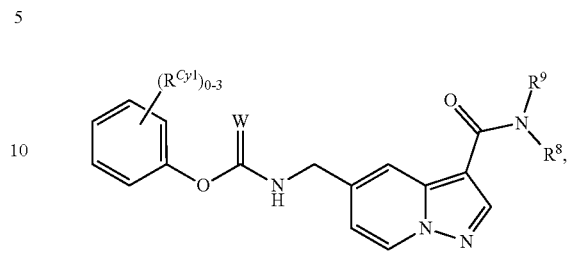

or a pharmaceutically acceptable salt thereof.

In some embodiments, the compound of Formula (I) has formula:

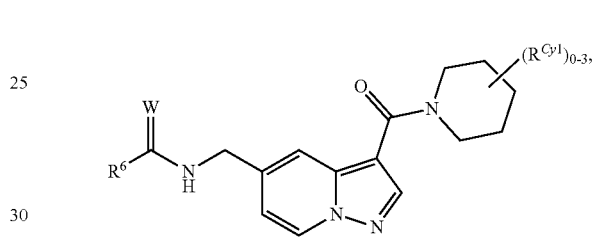

or a pharmaceutically acceptable salt thereof.

In some embodiments, the compound of Formula (I) has formula:

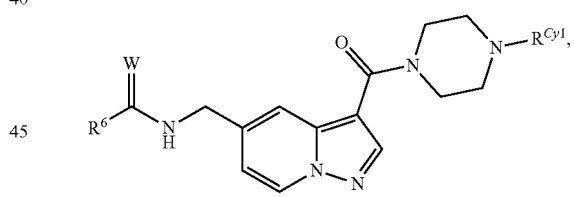

or a pharmaceutically acceptable salt thereof.

In some embodiments, the compound of Formula (I) has formula:

or a pharmaceutically acceptable salt thereof.

In some embodiments, the compound of Formula (I) is selected from any one of the following compounds, or a pharmaceutically acceptable salt thereof:

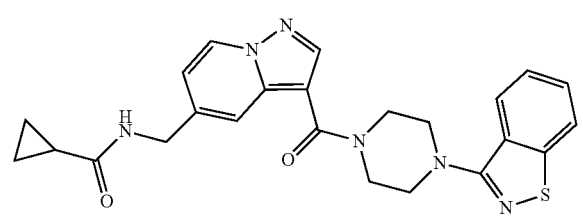
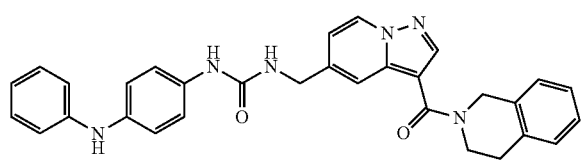
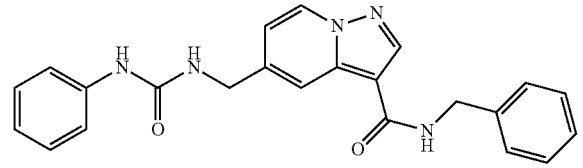
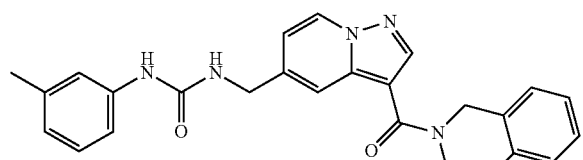
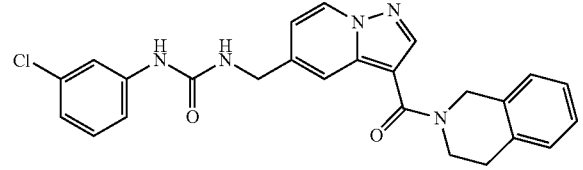
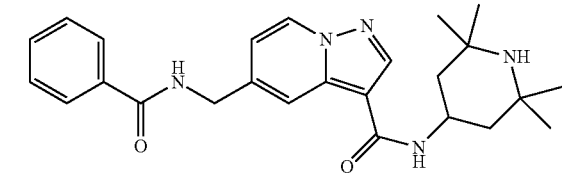
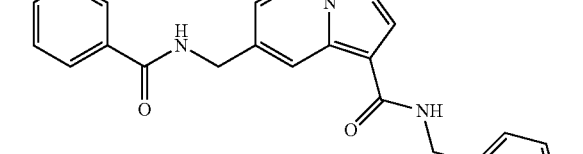
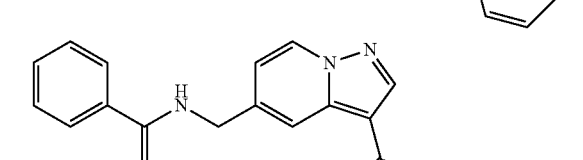
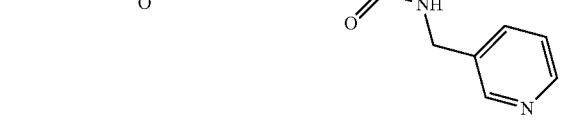
-continued
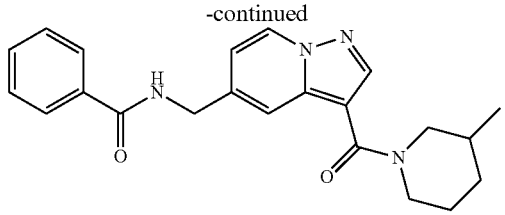
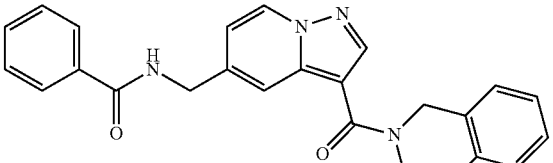
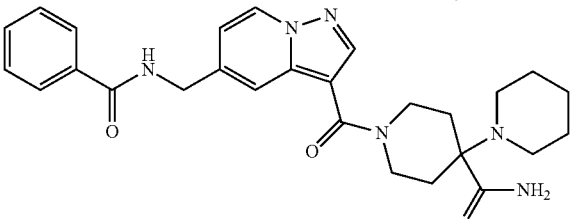
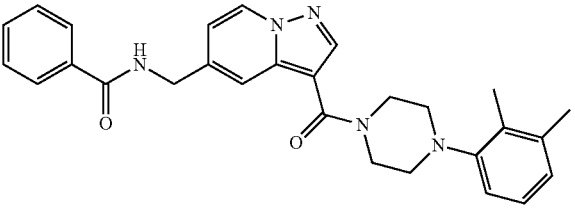
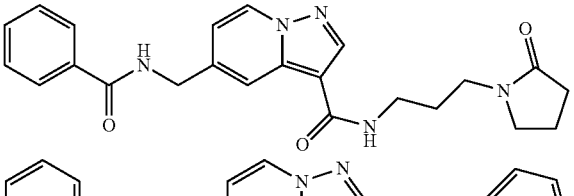
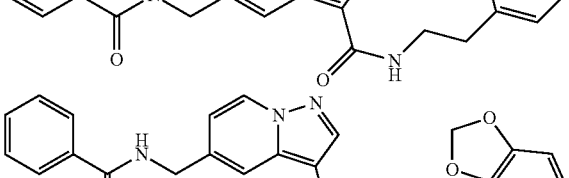
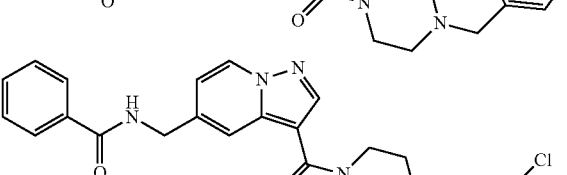
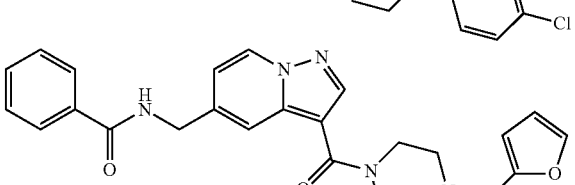

-continued

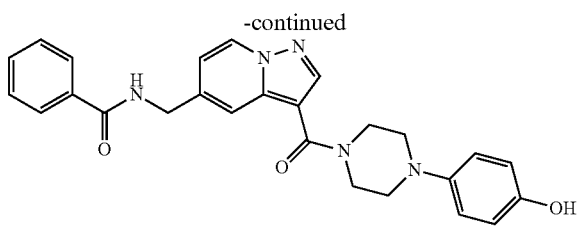

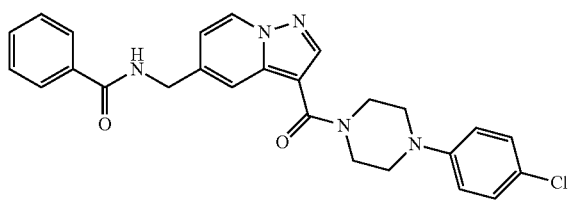

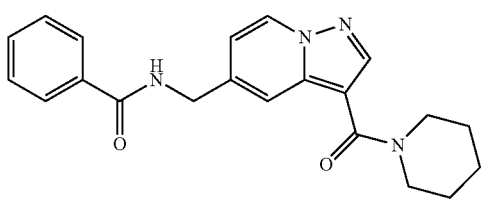

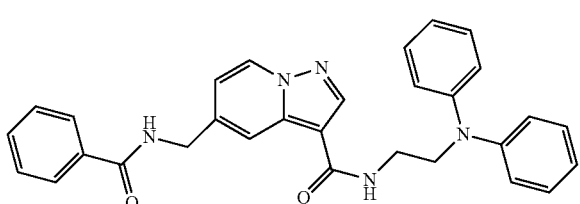

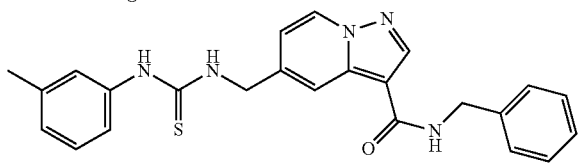

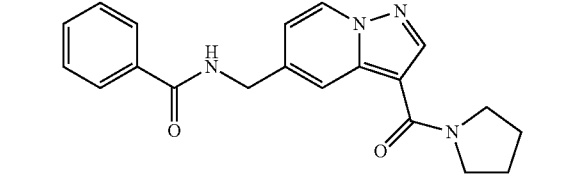

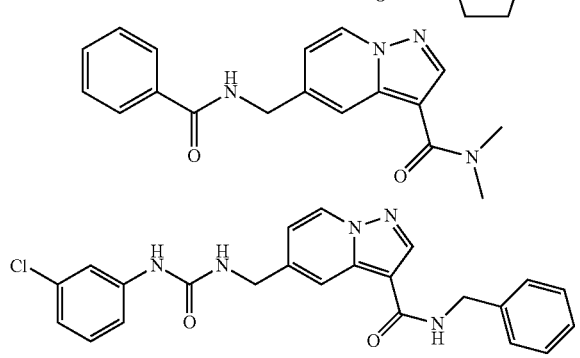

In some embodiments, the present disclosure provides a compound:

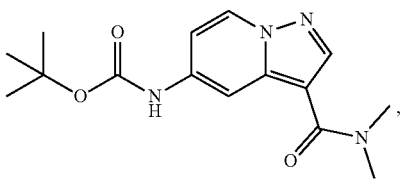 [SMILES: CN(C)C(=O)c1cnn2ccc(NC(=O)OC(C)(C)C)cc12]

or a pharmaceutically acceptable salt thereof.

In some embodiments, the present disclosure provides a compound:

(4-IPP)

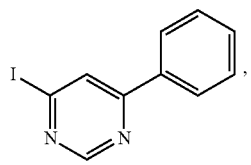

or a pharmaceutically acceptable salt thereof.

In some embodiments, the present disclosure provides a compound:

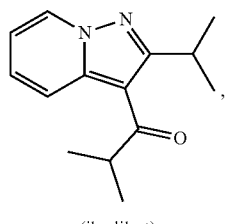

(ibudilast)

or a pharmaceutically acceptable salt thereof.

In some embodiments, the present disclosure provides a compound:

(ISO-1)

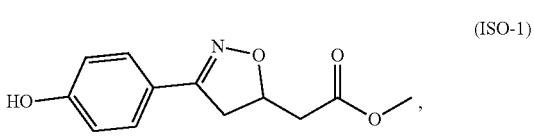 [SMILES: COC(=O)CC1CC(c2ccc(O)cc2)=NO1]

or a pharmaceutically acceptable salt thereof.

In some embodiments, a salt of a compound of Formula (I) disclosed herein, or any other compound disclosed herein, is formed between an acid and a basic group of the compound, such as an amino functional group, or a base and an acidic group of the compound, such as a carboxyl functional group. According to another embodiment, the compound is a pharmaceutically acceptable acid addition salt.

In some embodiments, acids commonly employed to form pharmaceutically acceptable salts of the compound as set forth in Formula (I) disclosed herein include inorganic acids such as hydrogen bisulfide, hydrochloric acid, hydrobromic acid, hydroiodic acid, sulfuric acid and phosphoric acid, as well as organic acids such as para-toluenesulfonic acid, salicylic acid, tartaric acid, bitartaric acid, ascorbic acid, maleic acid, besylic acid, fumaric acid, gluconic acid, glucuronic acid, formic acid, glutamic acid, methanesulfonic acid, ethanesulfonic acid, benzenesulfonic acid, lactic acid, oxalic acid, para-bromophenylsulfonic acid, carbonic acid, succinic acid, citric acid, benzoic acid and acetic acid, as well as related inorganic and organic acids. Such pharmaceutically acceptable salts thus include sulfate, pyrosulfate, bisulfate, sulfite, bisulfite, phosphate, monohydrogenphosphate, dihydrogenphosphate, metaphosphate, pyrophosphate, chloride, bromide, iodide, acetate, propionate, decanoate, caprylate, acrylate, formate, isobutyrate, caprate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, terephthalate, sulfonate, xylene sulfonate, phenylacetate, phenylpropionate, phenylbutyrate, citrate, lactate, β-hydroxybutyrate, glycolate, maleate, tartrate, methanesulfonate, propanesulfonate, naphthalene-1-sulfonate, naphthalene-2-sulfonate, mandelate and other salts. In one embodiment, pharmaceutically acceptable acid addition salts include those formed with mineral acids such as hydrochloric acid and hydrobromic acid, and those formed with organic acids such as maleic acid.

In some embodiments, bases commonly employed to form pharmaceutically acceptable salts of the compound as set forth in Formula (I) include hydroxides of alkali metals, including sodium, potassium, and lithium; hydroxides of alkaline earth metals such as calcium and magnesium; hydroxides of other metals, such as aluminum and zinc; ammonia, organic amines such as unsubstituted or hydroxyl-substituted mono-, di-, or tri-alkylamines, dicyclohexylamine; tributyl amine; pyridine; N-methyl, N-ethylamine; diethylamine; triethylamine; mono-, bis-, or tris-(2-OH—(C1-C6)-alkylamine), such as N,N-dimethyl-N-(2-hydroxyethyl)amine or tri-(2-hydroxyethyl)amine; N-methyl-D-glucamine; morpholine; thiomorpholine; piperidine; pyrrolidine; and amino acids such as arginine, lysine, and the like.

In some embodiments, the compound as set forth in Formula (I) disclosed herein, or pharmaceutically acceptable salts thereof, are substantially isolated.

Methods of Making Compounds of Formula (I)

Compounds as set forth in Formula (I), including salts thereof, can be prepared using organic synthesis techniques and can be synthesized according to any of numerous possible synthetic routes. A person skilled in the art knows how to select and implement appropriate synthetic protocols, and appreciates that a broad repertoire of synthetic organic reactions is available to be potentially employed in synthesizing compounds provided in this disclosure. Suitable synthetic methods of starting materials, intermediates, and products can be identified by reference to the literature, including reference sources such as: *Advances in Heterocyclic Chemistry*, Vols. 1-107 (Elsevier, 1963-2012); *Journal of Heterocyclic Chemistry* Vols. 1-49 (J. Heterocyclic Chemistry, 1964-2012); Carreira et al., (Ed.) *Science of Synthesis*, Vols. 1-48 (2001-2010) and Knowledge Updates KU2010/1-4; 2011/1-4; 2012/1-2 (Thieme, 2001-2012); Katritzky et al., (Ed.) *Comprehensive Organic Functional Group Transformations*, (Pergamon Press, 1996); Katritzky et al., (Ed.) *Comprehensive Organic Functional Group Transformations II* (Elsevier, 2$^{nd}$ Edition, 2004); Katritzky et al., (Ed.) *Comprehensive Heterocyclic Chemistry* (Pergamon Press, 1984); Katritzky et al., *Comprehensive Heterocyclic Chemistry II*, (Pergamon Press, 1996); Smith et al., *March's Advanced Organic Chemistry: Reactions, Mechanisms, and Structure*, 6$^{th}$ Ed. (Wiley, 2007); Trost et al. (Ed.) *Comprehensive Organic Synthesis* (Pergamon Press, 1991).

In one example, the compounds of Formula (I) can be synthesized as shown in Scheme 1.

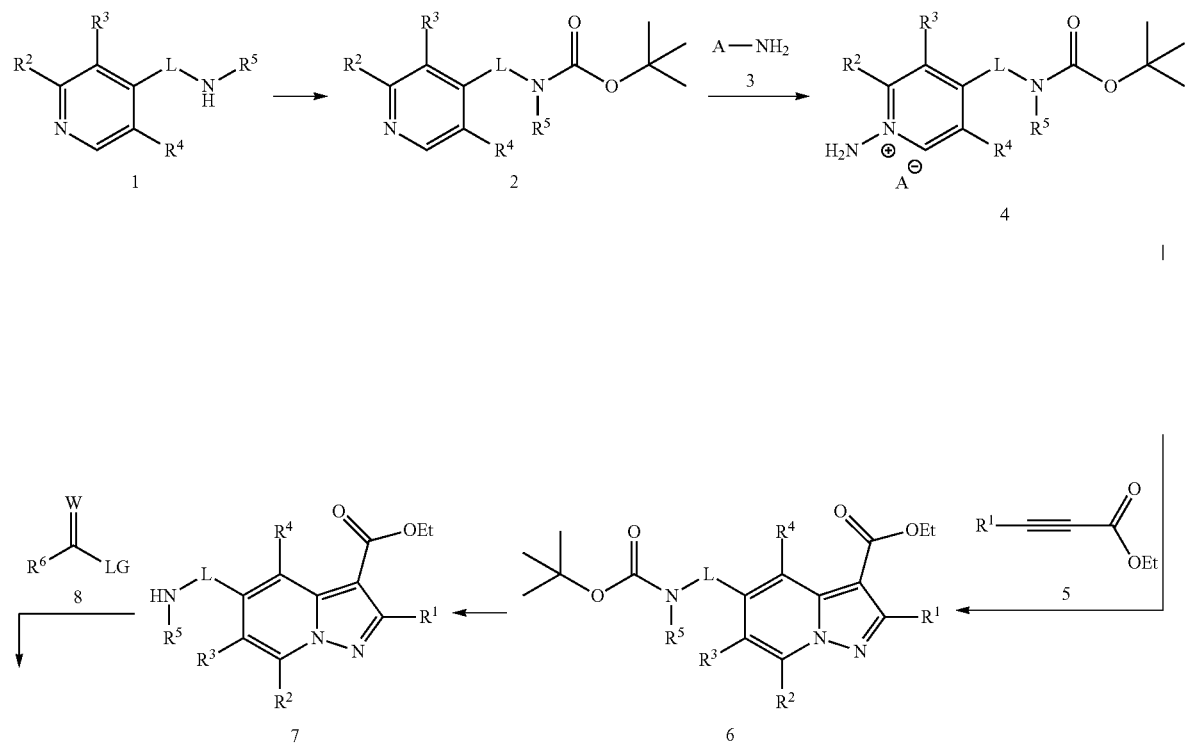

-continued

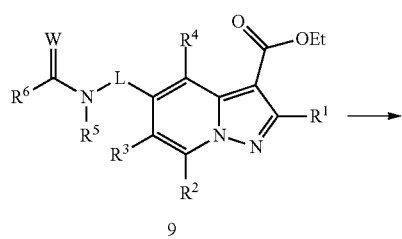

9

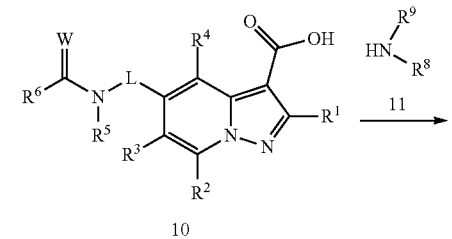

10

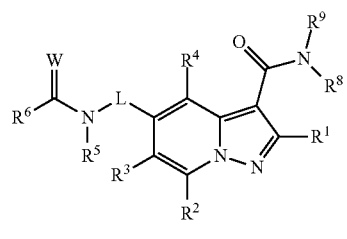

Formula (I)

Referring to Scheme 1, to obtain intermediate (2), a Boc anhydride is added to a mixture of 4-aminoalkylpyridine (1) and a mild base in an aprotic solvent. Suitable examples of a mild base include a triethylamine or an ethylisopropylamine. Suitable examples of an aprotic solvent include dichloromethane and chloroform. The reaction of (1) with Boc anhydride is typically carried out at a low temperature, such as at about 0° C. The reaction mixture may then be stirred at room temperature for several hours, for example, for about 6 hours, to yield the desired intermediate (2) after appropriate isolation and purification procedures. To obtain intermediate (4), the intermediate (2) can be treated with commercially available aminating reagent (3), such as O-(2,4-dinitrophenyl)hydroxylamine (CAS Registry No. 17508-17-7). The reagent (3) is typically commercially available and can be obtained from various commercial sources. The reaction between (2) and (3) is typically carried out in a polar aprotic solvent, such as THF, at about room temperature for several hours, for example, for about 7 hours, to yield product (4) as a precipitate, which can be collected by filtration. To obtain intermediate (6), the intermediate (4) is reacted with an alkyne (5) in the presence of a base in a polar aprotic solvent, such as DMF, at about room temperature for several hours, for example, for about 20 hours. Suitable examples of bases for this reaction include Hunig's base (N,N-diisopropylethylamine) and potassium carbonate. Various alkynes (5) are commercially available from commercial sources. The intermediate (7) can be obtained by deprotecting intermediate (6), for example, by treating compound (6) with a strong acid, such as hydrogen chloride or hydrogen fluoride. The deprotection reaction usually occurs at about room temperature for several hours, for example, for about 6 hours, in a polar aprotic solvent, such as dichloromethane, chloroform, or dioxane, to yield the product (7). The intermediate (7) can be coupled with the starting material (8), where LG is a leaving group, such as halogen, nosylate, or tosylate. The compounds (7) and (8) can be mixed in a polar aprotic solvent in the presence of a base at about 0° C. for several hours, for example, for about 6 hours, to yield intermediate (9) after appropriate purification and isolation procedures. The intermediate (9) can then be treated with a strong base reagent, such as 10 wt. % sodium hydroxide, in a polar protic solvent. Suitable example of a polar protic solvent includes an alcohol, such as ethanol or methanol. The reaction may occur at elevated temperature, for example, at about 40° C., for a period of time of several hours, for example, about 14 hours, to yield carboxylic acid (10). Finally, the carboxylic acid (10) can be coupled with amine (11) to yield the desired compound of Formula (I). The coupling reaction may be aided by the addition of 1-ethyl-3-(3-dimethylaminopropyl)carbodiimide (EDC) and hydroxybenzotriazole (HOBT) to the reaction mixture. A mild base, such as diisopropylethylamine (DIPEA), can also be added to the reaction mixture. The coupling reaction typically occurs at low temperature, such as at about 0° C., for several hours, for example, for about 1 hour, and then at room temperature for about 24 hours, to yield compound of Formula (I) after appropriate purification and isolation procedures.

In another example, the compounds of Formula (Ic), which correspond to the compound of Formula (I) where $R^6$ is $NR^7$-Cy, can be synthesized as shown in Scheme 2.

Scheme 2

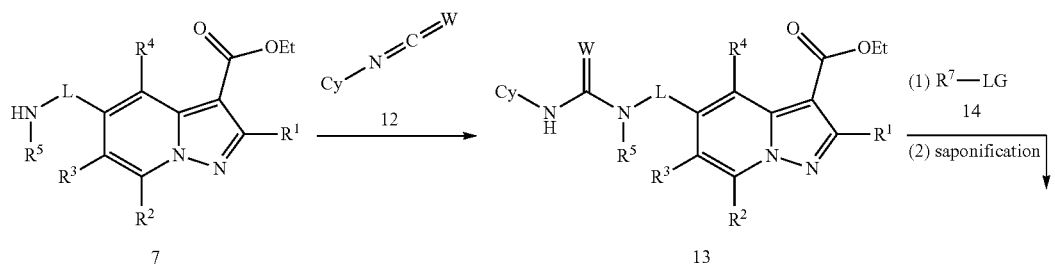

-continued

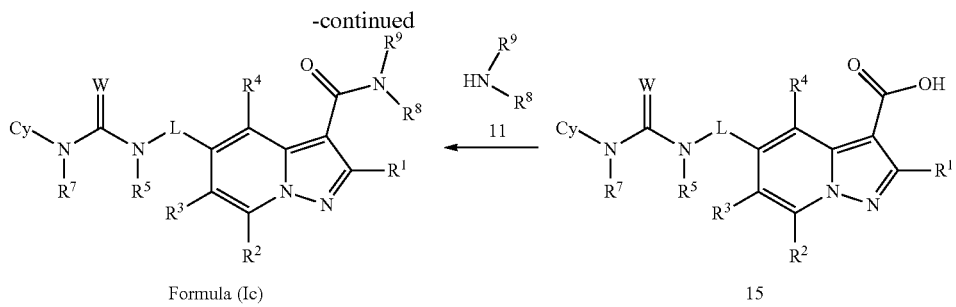

Formula (Ic)   15

Referring to Scheme 2, to obtain intermediate (13), the intermediate (7) can be treated with isocyanate or isothiocyanate (12). The reaction can be carried out in a polar aprotic solvent, such as dichloromethane or chloroform, in the presence of a base, such as triethylamine, at low temperature, for example, at about 0° C., for several hours, for example, for about 6 hours, to yield the compound of Formula (Ic) after appropriate purification and isolation procedures. The intermediate (13), in turn, can be reacted with a compound (14), in which $R^7$ is a substituent other than H and LG is a leaving group, such as halogen, tosylate, or nosylate, followed by saponification of the reaction product with a base, such as an alkali hydroxide, to obtain a urea or a thiourea (15). The intermediate (15) can then be reacted with an amine (11) as described above for Scheme 1, to obtain the compound of Formula (Ic).

In general, the reactions for preparing the compounds provided herein can be carried out in suitable solvents that can be readily selected by one of skill in the art of organic synthesis. Suitable solvents can be substantially non-reactive with the starting materials (reactants), the intermediates, or products at the temperatures at which the reactions are carried out, e.g., temperatures that can range from the solvent's freezing temperature to the solvent's boiling temperature. A given reaction can be carried out in one solvent or a mixture of more than one solvent. Depending on the particular reaction step, suitable solvents for a particular reaction step can be selected by the skilled artisan. Preparation of the compounds provided herein can involve the protection and deprotection of various chemical groups. The need for protection and deprotection, and the selection of appropriate protecting groups, can be readily determined by one skilled in the art. The chemistry of protecting groups can be found, for example, in P. G. M. Wuts and T. W. Greene, *Protective Groups in Organic Synthesis*, 4$^{th}$ Ed., Wiley & Sons, Inc., New York (2006).

Methods of Use

Human MIF (huMIF) is an immune mediator that promotes a sustained pro-inflammatory response. It is a 37.5 kDa homotrimer with two enzymatic activities, one as a phenylpyruvate tautomerase and the second as an oxidoreductase. When the tautomerase site is intact, MIF binds to a number of receptors, including CD74, CD44, CXCR4, CXCR7, and CXCR2. Inhibitors of the tautomerase activity alter the conformation of MIF and thereby inhibit its interaction with receptors. The RBC cytoplasm contains functionally active MIF, and MIF levels in the circulation correlate directly with the severity of malarial anemia. A series of studies have demonstrated that a higher number of CATT repeats in the promoter region of MIF (−794(CATT)*6/7/8) are correlated with increased levels of MIF synthesis, higher parasitemia, and greater risk of severe malarial anemia.

In some embodiments, the present disclosure provides compounds (e.g., compounds of Formula (I), 4-IPP, ibudilast), or pharmaceutically acceptable salts thereof, that modulate (e.g., inhibit) MIF and subsequently modulate a parasite-induced pathology in a cell (e.g., *P. falciparum*-induced pathology in a cell).

In some embodiments, a compound of the present disclosure inhibits huMIF. In some embodiments, a compound of the present disclosure inhibits a parasitic MIF (e.g., *P. falciparum* MIF, *T gondii* MIF, *Trypanosoma cruzi* MIF, *Leishmania major* MIF, *Giardia* app. MIF). In some embodiments, a compound of the present disclosure inhibits PfMVIF. In one example, the compound shows preferential (e.g., selective) binding to parasitic IF (e.g., *P. falciparum* MIF) as compared to huMIF. In some embodiments, the compound is at least 100 times more selective to parasitic MIF (e.g., PfMIF) as compared to huMIF. In some embodiments, modulating MIF comprises modulating a tautomerase activity of MIF (e.g., selectively modulating a tautomerase activity of MIF as compared to an oxidoreductase activity of MIF).

In some embodiments, the present disclosure provides a method for modulating (e.g., inhibiting) invasiveness of a parasite in a cell, comprising contacting the cell with an effective (e.g., therapeutically effective) amount of a compound of Formula (I), ibudilast, or 4-IPP, or a pharmaceutically acceptable salt thereof. The method may be carried out in vitro, in vivo (e.g., in a subject), or ex vivo.

In some embodiments, the present disclosure provides a method for modulating (e.g., inhibiting) a parasite-induced pathology in a cell, comprising contacting the cell with an effective (e.g., therapeutically effective) amount of a compound of Formula (I), ibudilast, or 4-IPP, or a pharmaceutically acceptable salt thereof. The method may be carried out in vitro, in vivo (e.g., in a subject), or ex vivo.

In some embodiments, the present disclosure provides a method for modulating (e.g., inhibiting) a parasite infection in a cell, comprising contacting the cell with an effective (e.g., therapeutically effective) amount of a compound of Formula (I), ibudilast, or 4-IPP, or a pharmaceutically acceptable salt thereof. The method may be carried out in vitro, in vivo (e.g., in a subject), or ex vivo.

In some embodiments, the present disclosure provides a method for modulating (e.g., inhibiting) an egress of a parasite from a cell, comprising contacting the cell with an effective (e.g., therapeutically effective) amount of a compound of Formula (I), ibudilast, or 4-IPP, or a pharmaceutically acceptable salt thereof. The method may be carried out in vitro, in vivo (e.g., in a subject), or ex vivo.

In some embodiments, in any of the methods disclosed herein, the cell is a human red blood cell (RBC). That is, the compound disclosed herein inhibits egress of the parasite from a red blood cell, inhibits parasite-induced pathology in a red blood cell, and modulates parasite infection in the red blood cell. In some embodiments, in any of the methods disclosed herein, the cell is a macrophage. That is, the compound disclosed herein inhibits egress of the parasite from a macrophage, inhibits parasite-induced pathology in a macrophage, and modulates parasite infection in the macrophage.

In some embodiments, in any of the methods disclosed herein, the parasite is a protozoan parasite. For example, the parasite belongs to a *Plasmodium* genus. In some embodiments, the parasite is *Plasmodium falciparum*: (*P. falciparum*), *P. vivax, P. ovale, P. malariae*, or *P. knowlesi*. In some embodiments, the parasite affects red blood cells of a subject and causes malaria (or malarial anemia) in the subject. In some embodiments of the present disclosure, the parasite is *Plasmodium falciparum*: (*P. falciparum*).

MIF homologues are identified in many parasitic species including *P. falciparum, T. gondii, Trypanosoma cruzi, Leishmania major*, and *Giardia* app. *Leishmania major* has two MIF orthologues which share about 30% sequence homology with huMIF or *P. falciparum* MIF. *L. major* MIFs retain the tautomerase active site, suggesting that these MIFs may be modulated by the compounds of the present disclosure. Several lines of research suggest that targeting *L. major* MIFs has beneficial therapeutic consequences. It has been reported that *L. major* MIF orthologues induce Erk activation and, thereby, reduce p53Ser phosphorylation extending the half-life of the infected macrophages and protecting them from apoptosis. Secondly, in chronic leishmaniasis the parasite-encoded MIFs suppress the development of a protective T-cell responses, similar to what has been reported for *P. falciparum* MIF. Therefore, inhibiting *L. major* MIF is beneficial for treatment of this disease. Structures of LmjMIF orthologues and their implication in the parasitic infection is discussed in Richardson et al, *Biochem Biophys Res Commun*. 2009; 380(3), 442-448, which is incorporated herein by reference in its entirety.

*Toxoplasma gondii* (*T. gondii*) has a homologue of MIF and a recent report documented that immunization with *T. gondii* MIF elicited strong humoral and cellular immune responses with high levels of IgG antibody and IFN-γ production compared to those of the controls, in addition to slight higher levels of IL-4 production. After vaccination, a stronger lymphoproliferative response was also noted. Correspondingly, the survival time of mice immunized with TgMIF was longer than that of the mice in control groups after challenge infection with virulent *T. gondii* RH tachyzoites. This data shows that the compounds of the present disclosure that preferentially target parasitic MIF (e.g., *T. gondii* MIF) are therapeutically effective against parasitic infections (e.g, *T. gondii* infections such as toxoplasmosis). Implication of TgMIF in toxoplasmosis is discussed, for example, in Liu et al, *Front Microbiol*. 2019, 10, 813, which is incorporated herein by reference in its entirety.

*Giardia lamblia*, a protozoan parasite responsible for giardiasis, was reported to have MIF implicated in the pathology of the infection. Implications of GlMIF in giardiasis are discussed, for example, in Buchko, G. et. al., *J Struct Funct Genomics*. 2013, 14, (2), 47-57, which is incorporated herein by reference in its entirety.

In some embodiments of the present disclosure, the parasite is selected from *Plasmodium falciparum* (*P. falciparum*), *T gondii, Trypanosoma cruzi, Leishmania major*, and *Giardia* app. That is, the parasite-associated infection treatable by the compounds of the present disclosure is selected from malaria (including malarial anemia), toxoplasmosis, trypanosomiasis, leishmaniasis, and giardiasis, respectively.

In some embodiments of the present disclosure, the parasite is selected from an ectoparasite, a helminth, and a protozoa. In some embodiments, the parasite is selected from a plasmodium, a tachyzoite, a schistosome, a fluke, a hookworm, a pinworm, a flatworm, a tapeworm, and a roundworm. Some parasites, such as hookworms, enter through skin on the soles of the feet when a person walks barefoot on contaminated soil. Others, such as schistosomes, which are flukes, enter through the skin when a person swims or bathes in water containing the parasites. Yet, others enter the body through the mouth. Doctors diagnose the infection by taking samples of blood, stool, urine, lymph, phlegm, or other infected tissue and examining or sending them to a laboratory for analysis.

In some embodiments, the parasitic infection treatable by the compounds of the present disclosure is ectoparasitic. Suitable examples of ectoparasitic infections include myiasis, pediculosis, phthiriasis, scabies, and trombiculosis.

In some embodiments, the parasitic infection treatable by the compounds of the present disclosure is helminthic. Suitable examples of helminthic infections include ascariasis, cestodiasis, clonorchiasis, echinococcosis, enterobiasis, fascioliasis, fasciolopsiasis, filariasis, guinea worm disease, heart worm disease, heterophyiasis, hookworm disease, loiasis, onchocerciasis, paragonimiasis, rat lung worm disease (angiostrongyliasis), schistosomiasis, strongyloidiasis, trichinosis, and trichuriasis.

In some embodiments, the parasitic infection treatable by the compounds of the present disclosure is protozoan. Suitable examples of protozoan infections include amebiasis, amebic dysentery, avian malaria, babesiosis, balantidiosis, black water fever, river blindness, Chagas disease, coccidiosis, enterohepatitis, giardiasis, ich, leishmaniasis, malaria, malarial anemia, sleeping sickness, toxoplasmosis, trichomoniasis, and trypanosomiasis.

In some embodiments, the present disclosure provides a method of modulating (e.g., inhibiting) parasite-induced Erk activation in a cell, comprising contacting the cell with an effective (e.g., therapeutically effective) amount of a compound of Formula (I), ibudilast, or 4-IPP, or a pharmaceutically acceptable salt thereof. The method may be carried out in vitro, in vivo (e.g., in a subject), or ex vivo. In some embodiments, the cell is an immune system cell (e.g., a macrophage) or a red blood cell. In some embodiments, the present disclosure provides a method of modulating (e.g., inhibiting) parasite-induced Erk activation in a subject, comprising administering to the subject a therapeutically effective amount of a compound of Formula (I), ibudilast, or 4-IPP, or a pharmaceutically acceptable salt thereof. In some embodiments, the subject is identified as in need of treatment (e.g., by a treating physician), that is, the subject is diagnosed with a parasitic infection.

In some embodiments, the present disclosure provides a method of modulating (e.g., reducing or inhibiting) parasite-induced p53Ser phosphorylation in a cell, comprising contacting the cell with an effective (e.g., therapeutically effective) amount of a compound of Formula (I), ibudilast, or 4-IPP, or a pharmaceutically acceptable salt thereof. The method may be carried out in vitro, in vivo (e.g., in a subject), or ex vivo. In some embodiments, the cell is an immune system cell (e.g., a macrophage). In some embodiments, the present disclosure provides a method of modulating (e.g., reducing or inhibiting) parasite-induced p53Ser phosphorylation in a subject, comprising administering to the subject a therapeutically effective amount of a compound of Formula (I), ibudilast, or 4-IPP, or a pharmaceutically acceptable salt thereof. In some embodiments, the subject is identified as in need of treatment (e.g., by a treating physician), that is, the subject is diagnosed with a parasitic infection.

Accordingly, the present disclosure provides a method for treating (or preventing) a disease or condition selected from parasitic infection (e.g., malaria, malarial anemia, leishmaniasis, toxoplasmosis, giardiasis, or trypanosomiasis) and parasitemia in a subject, comprising administering to the subject (e.g., in need thereof) an effective (e.g., therapeutically effective) amount of a compound of Formula (I), ibudilast, or 4-IPP, or a pharmaceutically acceptable salt thereof. In some embodiments, the malarial anemia is severe. In other embodiments, the malaria anemia is acute. Malaria is a mosquito-borne infectious disease that causes symptoms that typically include fever, tiredness, vomiting, headaches, yellow skin, seizures, and coma. Accordingly, the present disclosure provides a method for treating (or preventing) malaria in a subject, comprising administering to the subject (e.g., in need thereof) an effective (e.g., therapeutically effective) amount of a compound of Formula (I), ibudilast, or 4-IPP, or a pharmaceutically acceptable salt thereof.

Microphage migration inhibitory factor (MIF) is implicated in numerous neurological diseases (See, e.g., Leyton-Jaimes et al, *Experimental Neurology* 301 (2018) 83-91, which is incorporated herein by reference in its entirety). In these disease states, MIF modulates chemo-attraction, cytokine activity, and receptor binding, among other functions. In some embodiments, the compounds of the present disclosure may be used for treating or preventing a neurological disease, disorder, or condition, such as a neurodegenerative disease. In some embodiments, the neurodegenerative disease is selected from the group consisting of Alzheimer's disease (AD), Parkinson's disease (PD), Huntington's Disease (HD), motor neuron disease (MND), and Prion disease. In some embodiments, the neurological disorder is selected from cerebral amyloid angiopathy, vascular cognitive impairment (VCI), dementia, dementia with Lewy bodies, frontotemporal dementia (FTD), amyotrophic lateral sclerosis (ALS), multiple sclerosis, hippocampal sclerosis, Binswanger's disease, autism, and autistic spectrum disorders. In some embodiments, the neurological disorder is selected from the group consisting of AIDS dementia and HIV-1 induced neurotoxicity; cerebral ischemia, cerebrovascular ischemia, brain ischemia, cerebral palsy; cerebral tumour; chemotherapy-induced brain damage; cisplatin-induced neurotoxicity, Creutzfeldt-Jacob disease and its new variant associated with "mad cow" disease; diabetic neuropathy; diabetic neuropathic pain, Down's syndrome; epilepsy, post-traumatic epilepsy; Friedreich's ataxia; frontotemporal dementia; Hallervorden-Spatz disease; stroke, ischemic stroke; macular degeneration; methanol-induced neurotoxicity; meningitis (aseptic and tuberculous); multiple system atrophy; neoplasia; perinatal asphyxia; progressive supra-nuclear palsy; radiotherapy-induced brain damage; senile dementia; schizophrenia; depression, major depressive disorder, subharrachnoid haemorrhage/cerebral vasospasm; surgical trauma, including neurosurgery; neurosurgical trauma, transient ischemic attack (TIA); traumatic brain injury (TBI); traumatic spinal injury; spinal cord injury, vascular dementia; viral meningitis; encephalitis, and viral encephalitis.

Microphage migration inhibitory factor (MIF) is implicated in cancer (See, e.g., Nobre et al, *Pathol. Oncol. Res.* (2017) 23, 235-244, which is incorporated herein by reference in its entirety). MIF is found in almost all types of human cancers and is implicated in seemingly all stages of development of the tumors. MIF is produced by virtually all types of human body cells, in response to stress caused by different factors, leading to pathological conditions such as chronic inflammation and immunomodulation with suppression of immune surveillance and of immune response against tumors, angiogenesis, and carcinogenesis. Accordingly, in some embodiments, the compounds of the present disclosure are useful in treating cancer in a subject. In some embodiments, the cancer is selected from bladder cancer, brain cancer, breast cancer, colorectal cancer, cervical cancer, gastrointestinal cancer, genitourinary cancer, head and neck cancer, lung cancer, ovarian cancer, pancreatic cancer, prostate cancer, renal cancer, skin cancer, and testicular cancer. In some embodiments, the cancer is prostate cancer. In some embodiments, cancer is selected from sarcoma, angiosarcoma, fibrosarcoma, rhabdomyosarcoma, liposarcoma, myxoma, rhabdomyoma, fibroma, lipoma, teratoma, lung cancer, bronchogenic carcinoma squamous cell, undifferentiated small cell, undifferentiated large cell, adenocarcinoma, alveolar bronchiolar carcinoma, bronchial adenoma, sarcoma, lymphoma, chondromatous hamartoma, mesothelioma, gastrointestinal cancer, cancer of the esophagus, squamous cell carcinoma, adenocarcinoma, leiomyosarcoma, lymphoma, cancer of the stomach, carcinoma, lymphoma, leiomyosarcoma, cancer of the pancreas, ductal adenocarcinoma, insulinoma, glucagonoma, gastrinoma, carcinoid tumor, vipoma, cancer of the small bowel, adenocarcinoma, lymphoma, carcinoid tumors, Kaposi's sarcoma, leiomyoma, hemangioma, lipoma, neurofibroma, fibroma, cancer of the large bowel or colon, tubular adenoma, villous adenoma, hamartoma, leiomyoma, genitourinary tract cancer, cancer of the kidney adenocarcinoma, Wilm's tumor (nephroblastoma), lymphoma, leukemia, cancer of the bladder, cancer of the urethra, squamous cell carcinoma, transitional cell carcinoma, cancer of the prostate, cancer of the testis, seminoma, teratoma, embryonal carcinoma, teratocarcinoma, choriocarcinoma, sarcoma, interstitial cell carcinoma, fibroma, fibroadenoma, adenomatoid tumors, lipoma, liver cancer, hepatoma hepatocellular carcinoma, cholangiocarcinoma, hepatoblastoma, angiosarcoma, hepatocellular adenoma, hemangioma, bone cancer, osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor, chordoma, osteochrondroma (osteocartilaginous exostoses), benign chondroma, chondroblastoma, chondromyxofibroma, osteoid osteoma giant cell tumor, nervous system cancer, cancer of the skull, osteoma, hemangioma, granuloma, xanthoma, osteitis deformans, cancer of the meninges meningioma, meningiosarcoma, gliomatosis, cancer of the brain, astrocytoma, medulloblastoma, glioma, ependymoma, germinoma (pinealoma), glioblastoma multiforme, oligodendroglioma, schwannoma, retinoblastoma, congenital tumors, cancer of the spinal cord, neurofibroma, meningioma, glioma, sarcoma, gynecological cancer, cancer of the uterus, endometrial carcinoma, cancer of the cervix, cervical carcinoma, pre tumor cervical dysplasia, cancer of the ovaries, ovarian carcinoma, serous cystadenocarcinoma, mucinous cystadenocarcinoma, unclassified carcinoma, granulosa-theca cell tumor, Sertoli Leydig cell tumor, dysgerminoma, malignant teratoma, cancer of the vulva, squamous cell carcinoma, intraepithelial carcinoma, adenocarcinoma, fibrosarcoma, melanoma, cancer of the vagina, clear cell carcinoma, squamous cell carcinoma, botryoid sarcoma, embryonal rhabdomyosarcoma, cancer of the fallopian tubes, hematologic cancer, cancer of the blood, acute myeloid leukemia (AML), chronic myeloid leukemia (CML), acute lymphoblastic leukemia (ALL), chronic lymphoblastic leukemia, chronic lymphocytic leukemia, myeloproliferative diseases, multiple myeloma, myelodysplastic syndrome, Hodgkin's lymphoma, non-Hodgkin's lymphoma (malignant lymphoma), Waldenstrom's macroglobulinemia, skin cancer, malignant melanoma, basal cell carcinoma, squamous cell carcinoma, Kaposi's sarcoma, moles dysplastic nevi, lipoma, angioma, dermatofibroma, keloids, psoriasis, adrenal gland cancer, and neuroblastoma. In some embodiments, the compounds of the present disclosure can be used in treatment of breast cancer, AML, pancreatic ductal carcinoma, prostate cancer, EBV-associated tumors, glioblastoma, gastric cancer, oral squamous cancer, colorectal cancer, melanoma, esophageal squamous cell carcinoma, head and neck carcinoma, non-small cell lung carcinoma, cervical cancer, osteosarcoma and various other types of cancer as provided by Japanese patent application JP201722626, which is incorporated by reference herein in its entirety.

Microphage migration inhibitory factor (MIF) is implicated in inflammatory pathogenesis (See, e.g., Tilstam et al, *Expert Opin Ther Targets* 2017, 21 (7), 671-683, which is incorporated herein by reference in its entirety). Accordingly, in some embodiments, the compounds of the present disclosure are useful in treating or preventing an inflammatory disease or condition (e.g., rheumatoid arthritis, psoriasis, multiple sclerosis, rheumatoid arthritis, psoriasis, psoriatic arthritis, osteoarthritis, degenerative arthritis, polymyalgia rheumatic, ankylosing spondylitis, reactive arthritis, gout, pseudogout, inflammatory joint disease, systemic lupus erythematosus, polymyositis, or fibromyalgia). Additional types of inflammatory disease or conditions include achilles tendinitis, achondroplasia, acromegalic arthropathy, adhesive capsulitis, adult onset Still's disease, anserine bursitis, avascular necrosis, Behcet's syndrome, bicipital tendinitis, Blount's disease, brucellar spondylitis, bursitis, calcaneal bursitis, calcium pyrophosphate dihydrate deposition disease (CPPD), crystal deposition disease, Caplan's syndrome, carpal tunnel syndrome, chondrocalcinosis, chondromalacia patellae, chronic synovitis, chronic recurrent multifocal osteomyelitis, Churg-Strauss syndrome, Cogan's syndrome, corticosteroid-induced osteoporosis, costosternal syndrome, CREST syndrome, cryoglobulinemia, degenerative joint disease, dermatomyositis, diabetic finger sclerosis, diffuse idiopathic skeletal hyperostosis (DISH), discitis, discoid lupus erythematosus, drug-induced lupus, Duchenne's muscular dystrophy, Dupuytren's contracture, Ehlers-Danlos syndrome, enteropathic arthritis, epicondylitis, erosive inflammatory osteoarthritis, exercise-induced compartment syndrome, Fabry's disease, familial Mediterranean fever, Farber's lipogranulomatosis, Felty's syndrome, Fifth's disease, flat feet, foreign body synovitis, Freiberg's disease, fungal arthritis, Gaucher's disease, giant cell arteritis, gonococcal arthritis, Goodpasture's syndrome, granulomatous arteritis, hemarthrosis, hemochromatosis, Henoch-Schonlein purpura, Hepatitis B surface antigen disease, hip dysplasia, Hurler syndrome, hypermobility syndrome, hypersensitivity vasculitis, hypertrophic osteoarthropathy, immune complex disease, impingement syndrome, Jaccoud's arthropathy, juvenile ankylosing spondylitis, juvenile dermatomyositis, juvenile rheumatoid arthritis, Kawasaki disease, Kienbock's disease, Legg-Calve-Perthes disease, Lesch-Nyhan syndrome, linear scleroderma, lipoid dermatoarthritis, Lofgren's syndrome, Lyme disease, malignant synovioma, Marfan's syndrome, medial plica syndrome, metastatic carcinomatous arthritis, mixed connective tissue disease (MCTD), mixed cryoglobulinemia, mucopolysaccharidosis, multicentric reticulohistiocytosis, multiple epiphyseal dysplasia, mycoplasmal arthritis, myofascial pain syndrome, neonatal lupus, neuropathic arthropathy, nodular panniculitis, ochronosis, olecranon bursitis, Osgood-Schlatter's disease, osteoarthritis, osteochondromatosis, osteogenesis imperfecta, osteomalacia, osteomyelitis, osteonecrosis, osteoporosis, overlap syndrome, pachydermoperiostosis, Paget's disease of bone, palindromic rheumatism, patellofemoral pain syndrome, Pellegrini-Stieda syndrome, pigmented villonodular synovitis, piriformis syndrome, plantar fasciitis, polyarteritis nodos, polymyalgia rheumatica, polymyositis, popliteal cysts, posterior tibial tendinitis, Pott's disease, prepatellar bursitis, prosthetic joint infection, pseudoxanthoma elasticum, psoriatic arthritis, Raynaud's phenomenon, reactive arthritis/Reiter's syndrome, reflex sympathetic dystrophy syndrome, relapsing polychondritis, reperfusion injury, retrocalcaneal bursitis, rheumatic fever, rheumatoid vasculitis, rotator cuff tendinitis, sacroiliitis, salmonella osteomyelitis, sarcoidosis, saturnine gout, Scheuermann's osteochondritis, scleroderma, septic arthritis, seronegative arthritis, shigella arthritis, shoulder-hand syndrome, sickle cell arthropathy, Sjogren's syndrome, slipped capital femoral epiphysis, spinal stenosis, spondylolysis, staphylococcus arthritis, Stickler syndrome, subacute cutaneous lupus, Sweet's syndrome, Sydenham's chorea, syphilitic arthritis, systemic lupus erythematosus (SLE), Takayasu's arteritis, tarsal tunnel syndrome, tennis elbow, Tietse's syndrome, transient osteoporosis, traumatic arthritis, trochanteric bursitis, tuberculosis arthritis, arthritis of Ulcerative colitis, undifferentiated connective tissue syndrome (UCTS), urticarial vasculitis, viral arthritis, Wegener's granulomatosis, Whipple's disease, Wilson's disease, and yersinial arthritis.

Microphage migration inhibitory factor (MIF) is implicated in cardiovascular diseases (See, e.g., Tilstam et al, *Expert Opin Ther Targets* 2017, 21 (7), 671-683, which is incorporated herein by reference in its entirety). MIF is released by myocardium and modulate the manifestations of cardiovascular disease, specifically in myocardial ischemia. Accordingly, in some embodiments, the compounds of the present disclosure can be used for treating or preventing cardiovascular diseases such as hypertension, atherosclerosis, coronary artery disease (CAD), ischemia/reperfusion injury, ischemia, cerebral ischemia, heart attack, stroke, myocardial infarction, angina, heart failure, hypertensive heart disease, rheumatic heart disease, cardiomyopathy, celiac disease, cardiac arrest, high blood pressure, arrhythmia, congenital heart disease, peripheral artery disease, ischemic stroke or bronchial asthma. The compound of the present disclosure may be used to inhibit platelet aggregation and vasodilatation (in vitro, in vivo, and ex vivo), improve cerebral blood flow and attenuate allergic reactions. There effects of the compounds may be due to synergistic elevation of intracellular cyclic nucleotides and release of nitric oxide (NO) or prostacyclin from endothelium of a cell. The inhibition of platelet aggregation mediates anti-thrombotic activity of the compound. Accordingly, the compounds of the present disclosure can be used for treating multiple sclerosis, neuropathic pain, and in the improved efficacy and safety of opioids by decreasing opioid tolerance, withdrawal and reinforcement. The compounds slow progression of cortical atrophy as well as magnetization transfer ratio, a measure of tissue injury. The compounds are also useful for treating opioid use disorders and may enhance the analgesic effects of oxycodone.

Pharmaceutical Compositions and Formulations

This document also provides pharmaceutical compositions comprising an effective amount of a compound of Formula (I) disclosed herein, or a pharmaceutically acceptable salt thereof; and a pharmaceutically acceptable carrier. The pharmaceutical composition also can comprise any one of the additional therapeutic agents and/or therapeutic molecules described herein. The carrier(s) are "acceptable" in the sense of being compatible with the other ingredients of the formulation and, in the case of a pharmaceutically acceptable carrier, not deleterious to the recipient thereof in an amount used in the medicament.

Pharmaceutically acceptable carriers, adjuvants, and vehicles that can be used in the pharmaceutical compositions provided herein include, without limitation, ion exchangers, alumina, aluminum stearate, lecithin, serum proteins (e.g., human serum albumin), buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol, and wool fat.

The compositions or dosage forms can contain any one or more of the compounds or therapeutic agents described herein in the range of 0.005 percent to 100 percent with the balance made up from the suitable pharmaceutically acceptable carriers or excipients. The contemplated compositions can contain from about 0.001 percent to about 100 percent (e.g., from about 0.1 percent to about 95 percent, from about 75 percent to about 85 percent, or from about 20 percent to about 80 percent) of any one or more of the compounds or therapeutic agents provided herein, wherein the balance can be made up of any pharmaceutically acceptable carrier or excipient described herein, or any combination of these carriers or excipients.

Routes of Administration and Dosage Forms

The therapeutic compounds and/or pharmaceutical compositions provided herein (e.g., a composition containing one or more compounds of Formula (I), or a pharmaceutically acceptable salt thereof) can include those suitable for any acceptable route of administration. Acceptable routes of administration include, without limitation, buccal, cutaneous, endocervical, endosinusial, endotracheal, enteral, epidural, interstitial, intra-abdominal, intra-arterial, intrabronchial, intrabursal, intracerebral, intracisternal, intracoronary, intradermal, intracranial, intraductal, intraduodenal, intradural, intraepidermal, intraesophageal, intragastric, intragingival, intraileal, intralymphatic, intramedullary, intrameningeal, intramuscular, intranasal, intraovarian, intraperitoneal, intraprostatic, intrapulmonary, intrasinal, intraspinal, intrasynovial, intratesticular, intrathecal, intratubular, intratumoral, intrauterine, intravascular, intravenous, nasal, nasogastric, oral, parenteral, percutaneous, peridural, rectal, respiratory (inhalation), subcutaneous, sublingual, submucosal, topical, transdermal, transmucosal, transtracheal, ureteral, urethral, vaginal, intravitreal, subretinal or other intraocular routes of administrations.

Compositions and formulations described herein can conveniently be presented in a unit dosage form, e.g., tablets, sustained release capsules, and in liposomes, and can be prepared by any methods well known in the art of pharmacy. See, for example, Remington: The Science and Practice of Pharmacy, Lippincott Williams & Wilkins, Baltimore, MD (20th ed. 2000). Such preparative methods include, without limitation, the step of bringing into association with the molecule to be administered ingredients such as a carrier that constitutes one or more accessory ingredients. In general, the compositions can be prepared by uniformly and intimately bringing into association the active ingredients with liquid carriers, liposomes, or finely divided solid carriers, or both, and then, if necessary, shaping the product.

In some embodiments, any one or more of the compounds or therapeutic agents described herein can be administered orally. Compositions described herein that are suitable for oral administration can be presented as discrete units such as capsules, sachets, granules, or tablets each containing a predetermined amount (e.g., effective amount) of the active ingredient(s); a powder or granules; a solution or a suspension in an aqueous liquid or a non-aqueous liquid; an oil-in-water liquid emulsion; a water-in-oil liquid emulsion; packed in liposomes; or as a bolus. Soft gelatin capsules can be useful for containing such suspensions, which can beneficially increase the rate of compound absorption. In the case of tablets for oral use, carriers that are commonly used include, without limitation, lactose, sucrose, glucose, mannitol, silicic acid, and starches. Other acceptable excipients can include, without limitation, (a) fillers or extenders such as starches, lactose, sucrose, glucose, mannitol, and silicic acid, (b) binders such as carboxymethylcellulose, alginates, gelatin, polyvinylpyrrolidone, sucrose, and acacia, (c) humectants such as glycerol, (d) disintegrating agents such as agar-agar, calcium carbonate, potato or tapioca starch, alginic acid, certain silicates, and sodium carbonate, (e) solution retarding agents such as paraffin, (f) absorption accelerators such as quaternary ammonium compounds, (g) wetting agents such as cetyl alcohol and glycerol monostearate, (h) absorbents such as kaolin and bentonite clay, and (i) lubricants such as talc, calcium stearate, magnesium stearate, solid polyethylene glycols, sodium lauryl sulfate, and mixtures thereof. For oral administration in a capsule form, useful diluents include, without limitation, lactose and dried cornstarch. When aqueous suspensions are administered orally, the active ingredient(s) can be combined with emulsifying and suspending agents. If desired, certain sweetening and/or flavoring and/or coloring agents can be added. Compositions suitable for oral administration include, without limitation, lozenges comprising ingredients in a flavored basis, usually sucrose and acacia or tragacanth; and pastilles comprising the active ingredient(s) in an inert basis such as gelatin and glycerin, or sucrose and acacia.

Compositions suitable for parenteral administration include, without limitation, aqueous and non-aqueous sterile injection solutions or infusion solutions that may contain antioxidants, buffers, bacteriostats, and solutes that render the formulation isotonic with the blood of the intended recipient; and aqueous and non-aqueous sterile suspensions that may include suspending agents and thickening agents. The formulations can be presented in unit-dose or multi-dose containers, for example, sealed ampules and vials, and may be stored in a freeze dried (lyophilized) condition requiring only the addition of the sterile liquid carrier, for example water, for injections, saline (e.g., 0.9% saline solution), or 5% dextrose solution, immediately prior to use. Extemporaneous injection solutions and suspensions can be prepared from sterile powders, granules, and tablets. The injection solutions can be in the form of, for example, a sterile injectable aqueous or oleaginous suspension. This suspension can be formulated according to techniques known in the art using suitable dispersing or wetting agents and suspending agents. A sterile injectable preparation also can be a sterile injectable solution or suspension in a non-toxic parenterally-acceptable diluent or solvent, for example, as a solution in 1,3-butanediol. Among the acceptable vehicles and solvents that can be employed are mannitol, water, Ringer's solution, and isotonic sodium chloride solution. In addition, sterile, fixed oils can be used as a solvent or suspending medium. For this purpose, any bland fixed oil can be used including, without limitation, synthetic mono- or diglycerides. Fatty acids such as oleic acid and its glyceride derivatives can be used to prepare injectables. In some cases, natural pharmaceutically acceptable oils such as olive oil or castor oil, especially in their polyoxyethylated versions, can be used to prepare injectables. These oil solutions or suspensions also can contain a long-chain alcohol diluent or dispersant.

In some cases, a therapeutic compound and/or pharmaceutical composition provided herein can be administered in the form of suppository for rectal administration. These compositions can be prepared by mixing a compound described herein (e.g., a compound of Formula (I), or a pharmaceutically acceptable salt thereof) with a suitable non-irritating excipient that is solid at room temperature but liquid at the rectal temperature and therefore will melt in the rectum to release the active component(s). Such materials include, without limitation, cocoa butter, beeswax, and polyethylene glycols.

In some cases, a therapeutic compounds and/or pharmaceutical composition provided herein can be administered by nasal aerosol or inhalation. Such compositions can be prepared according to techniques well known in the art of pharmaceutical formulation and can be prepared as solutions in saline, employing benzyl alcohol or other suitable preservatives, absorption promoters to enhance bioavailability, fluorocarbons, and/or other solubilizing or dispersing agents known in the art. See, for example, U.S. Pat. No. 6,803,031. Additional formulations and methods for intranasal administration are found in Ilium, L., *J. Pharm. Pharmacol.*, 56:3-17 (2004); and Ilium, L., *Eur. J. Pharm. Sci.*, 11:1-18 (2000).

In some cases, a therapeutic compounds and/or pharmaceutical composition provided herein can be prepared as a topical composition and used in the form of an aerosol spray, cream, emulsion, solid, liquid, dispersion, foam, oil, gel, hydrogel, lotion, mousse, ointment, powder, patch, pomade, solution, pump spray, stick, towelette, soap, or other forms commonly employed in the art of topical administration and/or cosmetic and skin care formulation. The topical compositions can be in an emulsion form. Topical administration of a therapeutic compounds and/or pharmaceutical composition provided herein can be useful when the desired treatment involves areas or organs readily accessible by topical application. In some cases, a topical composition can include a combination of any one or more of the compounds or therapeutic agents described herein (e.g., a compound of Formula (I), or a pharmaceutically acceptable salt thereof), and one or more additional ingredients, carriers, excipients, or diluents including, without limitation, absorbents, anti-irritants, anti-acne agents, preservatives, antioxidants, coloring agents/pigments, emollients (moisturizers), emulsifiers, film-forming/holding agents, fragrances, leave-on exfoliants, prescription drugs, preservatives, scrub agents, silicones, skin-identical/repairing agents, slip agents, sunscreen actives, surfactants/detergent cleansing agents, penetration enhancers, and thickeners.

In some cases, one or more compounds or therapeutic agent described herein (e.g., a compound of Formula (I), or a pharmaceutically acceptable salt thereof) can be incorporated into a composition for coating an implantable medical device such as a prosthesis, artificial valve, vascular graft, stent, or catheter. Suitable coatings and the general preparation of coated implantable devices are known in the art and are exemplified in U.S. Pat. Nos. 6,099,562; 5,886,026; and 5,304,121. The coatings can be biocompatible polymeric materials such as a hydrogel polymer, polymethyldisiloxane, polycaprolactone, polyethylene glycol, polylactic acid, ethylene vinyl acetate, or mixture thereof. In some cases, the coating can optionally be further covered by a suitable topcoat of fluorosilicone, polysaccharides, polyethylene glycol, phospholipids or combinations thereof to impart controlled release characteristics in the composition.

In some cases, this document provides an implantable drug release device impregnated with or containing one or more compounds or therapeutic agents described herein (e.g., a compound of Formula (I), or a pharmaceutically acceptable salt thereof) such that the compound(s) or therapeutic agent(s) are released from the device and are therapeutically active.

Dosages and Regimens

A composition (e.g., pharmaceutical compositions provided herein) containing a compound provided herein (e.g., a compound of Formula (I), or a pharmaceutically acceptable salt thereof) can include that compound in an effective amount (e.g., a therapeutically effective amount).

Effective doses can vary, depending on the disease, disorder, or condition being treated (or prevented), the severity of the disease, disorder, or condition, the route of administration, the sex, age and general health condition of the subject, excipient usage, the possibility of co-usage with other therapeutic treatments such as use of other agents, and the judgment of the treating physician.

In some embodiments, an effective amount of a compound of Formula (I), or a pharmaceutically acceptable salt thereof, can range, for example, from about 0.1 mg to about 1000 mg. In some cases, the effective amount can be from about 0.5 mg to about 500 mg of a compound disclosed herein, or any amount in between these two values, for example, one of about 0.5 mg, about 1 mg, about 2 mg, about 5 mg, about 10 mg, about 20 mg, about 50 mg, about 100 mg, about 200 mg, about 250 mg, about 300 mg, about 400 mg, or about 500 mg. The effective amount can be an amount sufficient to alleviate or reduce one or more of the symptoms associated with a disease, disorder, or condition being treated (or prevented) as described herein.

In some cases, an effective amount of a compound of Formula (I), or a pharmaceutically acceptable salt thereof, can range, for example, from about 0.001 mg/kg to about 500 mg/kg (e.g., from about 0.001 mg/kg to about 200 mg/kg; from about 0.01 mg/kg to about 200 mg/kg; from about 0.01 mg/kg to about 150 mg/kg; from about 0.01 mg/kg to about 100 mg/kg; from about 0.01 mg/kg to about 50 mg/kg; from about 0.01 mg/kg to about 10 mg/kg; from about 0.01 mg/kg to about 5 mg/kg; from about 0.01 mg/kg to about 1 mg/kg; from about 0.01 mg/kg to about 0.5 mg/kg; from about 0.01 mg/kg to about 0.1 mg/kg; from about 0.1 mg/kg to about 200 mg/kg; from about 0.1 mg/kg to about 150 mg/kg; from about 0.1 mg/kg to about 100 mg/kg; from about 0.1 mg/kg to about 50 mg/kg; from about 0.1 mg/kg to about 10 mg/kg; from about 0.1 mg/kg to about 5 mg/kg; from about 0.1 mg/kg to about 2 mg/kg; from about 0.1 mg/kg to about 1 mg/kg; from about 0.1 mg/kg to about 0.5 mg/kg, or from about 0.5 mg/kg to about 500 mg/kg).

In some cases, an effective amount of a compound of Formula (I), or a pharmaceutically acceptable salt thereof, can be about 0.1 mg/kg, about 0.5 mg/kg, about 1 mg/kg, about 2 mg/kg, or about 5 mg/kg.

The foregoing dosages can be administered on a daily basis (e.g., as a single dose or as two or more divided doses, e.g., once daily, twice daily, thrice daily) or on a non-daily basis (e.g., every other day, every two days, every three days, once weekly, twice weekly, once every two weeks, or once a month). In some cases, the dosages can be administered every 4 hours, 6 hours, 8 hours, 12 hours, or 24 hours.

Kits

This document also provides pharmaceutical kits useful, for example, to inhibit MIF. In some cases, this document provides pharmaceutical kits useful, for example, to treat or prevent a disease, disorder, or condition referred to herein. Such pharmaceutical kits can include one or more containers containing a pharmaceutical composition that includes a therapeutically effective amount of a compound provided herein (e.g., a compound of Formula (I), or a pharmaceutically acceptable salt thereof). In some cases, such kits can further include, if desired, one or more of various conventional pharmaceutical kit components such as containers with one or more pharmaceutically acceptable carriers. Instructions, either as inserts or as labels, indicating quantities of the components to be administered, guidelines for administration, and/or guidelines for mixing the components also can be included in a kit provided herein. In some embodiments, the kit comprising at least one additional therapeutic agent as described herein, or a pharmaceutically acceptable salt thereof, or a pharmaceutical composition comprising same.

Combination Therapies

In some cases, one or more compounds provided herein (e.g., a compound set forth in Formula (I), or a pharmaceutically acceptable salt thereof) can be combined with one or more additional therapeutic molecules. Examples of therapeutic molecules that can be used in combination with one or more compounds provided herein (e.g., a compound set forth in Formula (I), or a pharmaceutically acceptable salt thereof) include, without limitation, a drug that cures or prevents malaria, an anti-cancer drug, or a drug that treats or prevents neurodegenerative disease or condition, and a drug that treats or prevents a cardiovascular condition. Other classes of therapeutic agents may also be used in combination with the compounds of the present disclosure.

Suitable examples of additional therapeutic agents include anti-malarial agents such as quinine and related agents, chloroquine, amodiaquine, pyrimethamine, proguanil, sulfonamides, mefloquine, atovaquone, primaquine, artemisinin and derivatives, halofantrine, doxycycline, or clindamycin.

Other suitable examples of additional therapeutic agents include anti-cancer agents such as antimetabolites (including, without limitation, folic acid antagonists, pyrimidine analogs, purine analogs and adenosine deaminase inhibitors) such as methotrexate, 5-fluorouracil, floxuridine, cytarabine, 6-mercaptopurine, 6-thioguanine, fludarabine phosphate, pentostatine, and gemcitabine. Other examples of anti-cancer agents include alkylating agents (including, without limitation, nitrogen mustards, ethylenimine derivatives, alkyl sulfonates, nitrosoureas and triazenes) such as uracil mustard, chlormethine, cyclophosphamide, ifosfamide, melphalan, chlorambucil, pipobroman, triethylene-melamine, triethylenethiophosphoramine, busulfan, carmustine, lomustine, streptozocin, dacarbazine, and temozolomide. In some embodiments, the compound of the present disclosure can be combined with a surgical cancer treatment or a radiotherapy.

Yet other suitable examples of additional therapeutic agents include cardiac medications, such as rivaroxaban, dabigatran, apixaban, heparin, warfarin, aspirin, clopidogrel, dipyridamole, prasugrel, ticagrelor, benazepril, captopril, enalapril, fosinopril, lisinopril, moexipril, perindopril, quinapril, ramipril, trandolapril, candesartan, eprosartan, irbesartan, losartan, telmisartan, valsartan, acebutolol, atenolol, betaxolol, bisoprolol/hydrochlorothiazide, bisoprolol, metoprolol, nadolol, propranolol, sotalol, amlodipine, diltiazem, felodipine, nifedipine, nimodipine, nisoldipine, verapamil), amiloride, bumetanide, chlorothiazide, chlorthalidone, furosemide, hydro-chlorothiazide, indapamide, spironolactone, isosorbidedinitrate, nesiritide, hydralazine, nitrates, or minoxidil.

Yet other suitable examples of additional therapeutic agents include neurological agents (e.g., L-DOPA, memantine, and riluzole), and therapies for a neurodegenerative disease (e.g., edaravone or tetrabenazine) or agents intended to raise NAD levels (nicotinamide riboside or nicotinamide mononucleotide).

Additional examples of therapeutic molecules that can be used in combination with one or more compounds provided herein (e.g., a compound set forth in Formula (I), or a pharmaceutically acceptable salt thereof) include, without limitation, anti-inflammatory agents (e.g., NSAIDs, steroids and antibodies against IL-6 or TNF-alpha) and antimicrobial agents (e.g., antibiotics, anti-mycobacterial drugs, and antiviral agents).

One or more compounds provided herein (e.g., a compound set forth in Formula (I), or a pharmaceutically acceptable salt thereof) and the one or more therapeutic molecules can be administered in any order or simultaneously. If simultaneously administered, they can be provided in a single, unified, form or in multiple forms (e.g., either as a single pill or as two separate pills). One of the items can be given in multiple doses, or both can be given as multiple doses. If not simultaneous, the timing between the multiple doses can vary from more than zero weeks to less than four weeks.

Definitions

As used herein, the term "about" means "approximately" (e.g., plus or minus approximately 10% of the indicated value).

At various places in the present specification, substituents of compounds of the invention are disclosed in groups or in ranges. It is specifically intended that the invention include each and every individual subcombination of the members of such groups and ranges. For example, the term "$C_{1-6}$ alkyl" is specifically intended to individually disclose methyl, ethyl, $C_3$ alkyl, $C_4$ alkyl, $C_5$ alkyl, and $C_6$ alkyl.

At various places in the present specification various aryl, heteroaryl, cycloalkyl, and heterocycloalkyl rings are described. Unless otherwise specified, these rings can be attached to the rest of the molecule at any ring member as permitted by valency. For example, the term "a pyridine ring" or "pyridinyl" may refer to a pyridin-2-yl, pyridin-3-yl, or pyridin-4-yl ring.

It is further appreciated that certain features of the invention, which are, for clarity, described in the context of separate embodiments, can also be provided in combination in a single embodiment. Conversely, various features of the invention which are, for brevity, described in the context of a single embodiment, can also be provided separately or in any suitable subcombination.

The term "aromatic" refers to a carbocycle or heterocycle having one or more polyunsaturated rings having aromatic character (i.e., having (4n+2) delocalized π (pi) electrons where n is an integer).

The term "n-membered" where n is an integer typically describes the number of ring-forming atoms in a moiety where the number of ring-forming atoms is n. For example, piperidinyl is an example of a 6-membered heterocycloalkyl ring, pyrazolyl is an example of a 5-membered heteroaryl ring, pyridyl is an example of a 6-membered heteroaryl ring, and 1,2,3,4-tetrahydro-naphthalene is an example of a 10-membered cycloalkyl group.

As used herein, the phrase "optionally substituted" means unsubstituted or substituted. The substituents are independently selected, and substitution may be at any chemically accessible position. As used herein, the term "substituted" means that a hydrogen atom is removed and replaced by a substituent. A single divalent substituent, e.g., oxo, can replace two hydrogen atoms. It is to be understood that substitution at a given atom is limited by valency.

Throughout the definitions, the term "$C_{n-m}$" indicates a range which includes the endpoints, wherein n and m are integers and indicate the number of carbons. Examples include $C_{1-4}$, $C_{1-6}$, and the like.

As used herein, the term "$C_{n-m}$ alkyl", employed alone or in combination with other terms, refers to a saturated hydrocarbon group that may be straight-chain or branched, having n to m carbons. Examples of alkyl moieties include, but are not limited to, chemical groups such as methyl, ethyl, n-propyl, isopropyl, n-butyl, tert-butyl, isobutyl, sec-butyl; higher homologs such as 2-methyl-1-butyl, n-pentyl, 3-pentyl, n-hexyl, 1,2,2-trimethylpropyl, and the like. In some embodiments, the alkyl group contains from 1 to 6 carbon atoms, from 1 to 4 carbon atoms, from 1 to 3 carbon atoms, or 1 to 2 carbon atoms.

As used herein, the term "$C_{n-m}$ haloalkyl", employed alone or in combination with other terms, refers to an alkyl group having from one halogen atom to 2s+1 halogen atoms which may be the same or different, where "s" is the number of carbon atoms in the alkyl group, wherein the alkyl group has n to m carbon atoms. In some embodiments, the haloalkyl group is fluorinated only. In some embodiments, the alkyl group has 1 to 6, 1 to 4, or 1 to 3 carbon atoms.

As used herein, "$C_{n-m}$ alkenyl" refers to an alkyl group having one or more double carbon-carbon bonds and having n to m carbons. Example alkenyl groups include, but are not limited to, ethenyl, n-propenyl, isopropenyl, n-butenyl, sec-butenyl, and the like. In some embodiments, the alkenyl moiety contains 2 to 6, 2 to 4, or 2 to 3 carbon atoms.

As used herein, "$C_{n-m}$ alkynyl" refers to an alkyl group having one or more triple carbon-carbon bonds and having n to m carbons. Example alkynyl groups include, but are not limited to, ethynyl, propyn-1-yl, propyn-2-yl, and the like. In some embodiments, the alkynyl moiety contains 2 to 6, 2 to 4, or 2 to 3 carbon atoms.

As used herein, the term "$C_{n-m}$ alkylene", employed alone or in combination with other terms, refers to a divalent alkyl linking group having n to m carbons. Examples of alkylene groups include, but are not limited to, ethan-1,1-diyl, ethan-1,2-diyl, propan-1,1,-diyl, propan-1,3-diyl, propan-1,2-diyl, butan-1,4-diyl, butan-1,3-diyl, butan-1,2-diyl, 2-methyl-propan-1,3-diyl, and the like. In some embodiments, the alkylene moiety contains 2 to 6, 2 to 4, 2 to 3, 1 to 6, 1 to 4, or 1 to 2 carbon atoms.

As used herein, the term "$C_{n-m}$ alkoxy", employed alone or in combination with other terms, refers to a group of formula —O-alkyl, wherein the alkyl group has n to m carbons. Example alkoxy groups include, but are not limited to, methoxy, ethoxy, propoxy (e.g., n-propoxy and isopropoxy), butoxy (e.g., n-butoxy and tert-butoxy), and the like. In some embodiments, the alkyl group has 1 to 6, 1 to 4, or 1 to 3 carbon atoms.

As used herein, "$C_{n-m}$ haloalkoxy" refers to a group of formula —O-haloalkyl having n to m carbon atoms. An example haloalkoxy group is $OCF_3$. In some embodiments, the haloalkoxy group is fluorinated only. In some embodiments, the alkyl group has 1 to 6, 1 to 4, or 1 to 3 carbon atoms.

As used herein, the term "amino" refers to a group of formula —$NH_2$.

As used herein, the term "$C_{n-m}$ alkylamino" refers to a group of formula —NH(alkyl), wherein the alkyl group has n to m carbon atoms. In some embodiments, the alkyl group has 1 to 6, 1 to 4, or 1 to 3 carbon atoms. Examples of alkylamino groups include, but are not limited to, N-methylamino, N-ethylamino, N-propylamino (e.g., N-(n-propyl)amino and N-isopropylamino), N-butylamino (e.g., N-(n-butyl)amino and N-(tert-butyl)amino), and the like.

As used herein, the term "di($C_{n-m}$-alkyl)amino" refers to a group of formula —N(alkyl)$_2$, wherein the two alkyl groups each has, independently, n to m carbon atoms. In some embodiments, each alkyl group independently has 1 to 6, 1 to 4, or 1 to 3 carbon atoms.

As used herein, the term "$C_{n-m}$ alkoxycarbonyl" refers to a group of formula —C(O)O-alkyl, wherein the alkyl group has n to m carbon atoms. In some embodiments, the alkyl group has 1 to 6, 1 to 4, or 1 to 3 carbon atoms. Examples of alkoxycarbonyl groups include, but are not limited to, methoxycarbonyl, ethoxycarbonyl, propoxycarbonyl (e.g., n-propoxycarbonyl and isopropoxycarbonyl), butoxycarbonyl (e.g., n-butoxycarbonyl and tert-butoxycarbonyl), and the like.

As used herein, the term "$C_{n-m}$ alkylcarbonyl" refers to a group of formula —C(O)— alkyl, wherein the alkyl group has n to m carbon atoms. In some embodiments, the alkyl group has 1 to 6, 1 to 4, or 1 to 3 carbon atoms. Examples of alkylcarbonyl groups include, but are not limited to, methylcarbonyl, ethylcarbonyl, propylcarbonyl (e.g., n-propylcarbonyl and isopropylcarbonyl), butylcarbonyl (e.g., n-butylcarbonyl and tert-butylcarbonyl), and the like.

As used herein, the term "$C_{n-m}$ alkylcarbonylamino" refers to a group of formula —NHC(O)-alkyl, wherein the alkyl group has n to m carbon atoms. In some embodiments, the alkyl group has 1 to 6, 1 to 4, or 1 to 3 carbon atoms.

As used herein, the term "$C_{n-m}$ alkylsulfonylamino" refers to a group of formula —NHS(O)$_2$-alkyl, wherein the alkyl group has n to m carbon atoms. In some embodiments, the alkyl group has 1 to 6, 1 to 4, or 1 to 3 carbon atoms.

As used herein, the term "aminosulfonyl" refers to a group of formula —S(O)$_2NH_2$.

As used herein, the term "$C_{n-m}$ alkylaminosulfonyl" refers to a group of formula —S(O)$_2$NH(alkyl), wherein the alkyl group has n to m carbon atoms. In some embodiments, the alkyl group has 1 to 6, 1 to 4, or 1 to 3 carbon atoms.

As used herein, the term "di($C_{n-m}$ alkyl)aminosulfonyl" refers to a group of formula —S(O)$_2$N(alkyl)$_2$, wherein each alkyl group independently has n to m carbon atoms. In some embodiments, each alkyl group has, independently, 1 to 6, 1 to 4, or 1 to 3 carbon atoms.

As used herein, the term "aminosulfonylamino" refers to a group of formula —NHS(O)$_2NH_2$.

As used herein, the term "$C_{n-m}$ alkylaminosulfonylamino" refers to a group of formula —NHS(O)$_2$NH(alkyl), wherein the alkyl group has n to m carbon atoms. In some embodiments, the alkyl group has 1 to 6, 1 to 4, or 1 to 3 carbon atoms.

As used herein, the term "di($C_{n-m}$ alkyl)aminosulfonylamino" refers to a group of formula —NHS(O)$_2$N(alkyl)$_2$, wherein each alkyl group independently has n to m carbon atoms. In some embodiments, each alkyl group has, independently, 1 to 6, 1 to 4, or 1 to 3 carbon atoms.

As used herein, the term "aminocarbonylamino", employed alone or in combination with other terms, refers to a group of formula —NHC(O)NH$_2$.

As used herein, the term "$C_{n-m}$ alkylaminocarbonylamino" refers to a group of formula —NHC(O)NH(alkyl), wherein the alkyl group has n to m carbon atoms. In some embodiments, the alkyl group has 1 to 6, 1 to 4, or 1 to 3 carbon atoms.

As used herein, the term "di($C_{n-m}$ alkyl)aminocarbonylamino" refers to a group of formula —NHC(O)N(alkyl)$_2$, wherein each alkyl group independently has n to m carbon atoms. In some embodiments, each alkyl group has, independently, 1 to 6, 1 to 4, or 1 to 3 carbon atoms.

As used herein, the term "carbamyl" to a group of formula —C(O)NH$_2$.

As used herein, the term "$C_{n-m}$ alkylcarbamyl" refers to a group of formula —C(O)—NH(alkyl), wherein the alkyl group has n to m carbon atoms. In some embodiments, the alkyl group has 1 to 6, 1 to 4, or 1 to 3 carbon atoms.

As used herein, the term "di($C_{n-m}$-alkyl)carbamyl" refers to a group of formula —C(O)N(alkyl)$_2$, wherein the two alkyl groups each has, independently, n to m carbon atoms. In some embodiments, each alkyl group independently has 1 to 6, 1 to 4, or 1 to 3 carbon atoms.

As used herein, the term "thio" refers to a group of formula —SH.

As used herein, the term "$C_{n-m}$ alkylthio" refers to a group of formula —S-alkyl, wherein the alkyl group has n to m carbon atoms. In some embodiments, the alkyl group has 1 to 6, 1 to 4, or 1 to 3 carbon atoms.

As used herein, the term "$C_{n-m}$ alkylsulfinyl" refers to a group of formula —S(O)— alkyl, wherein the alkyl group has n to m carbon atoms. In some embodiments, the alkyl group has 1 to 6, 1 to 4, or 1 to 3 carbon atoms.

As used herein, the term "$C_{n-m}$ alkylsulfonyl" refers to a group of formula —S(O)$_2$-alkyl, wherein the alkyl group has n to m carbon atoms. In some embodiments, the alkyl group has 1 to 6, 1 to 4, or 1 to 3 carbon atoms.

As used herein, the term "carbonyl", employed alone or in combination with other terms, refers to a —C(=O)— group, which may also be written as C(O).

As used herein, the term "carboxy" refers to a —C(O)OH group.

As used herein, the term "cyano-$C_{1-3}$ alkyl" refers to a group of formula —($C_{1-3}$ alkylene)-CN.

As used herein, the term "HO—$C_{1-3}$ alkyl" refers to a group of formula —($C_{1-3}$ alkylene)-OH.

As used herein, "halo" refers to F, Cl, Br, or I. In some embodiments, a halo is F, Cl, or Br.

As used herein, the term "aryl," employed alone or in combination with other terms, refers to an aromatic hydrocarbon group, which may be monocyclic or polycyclic (e.g., having 2, 3 or 4 fused rings). The term "$C_{n-m}$ aryl" refers to an aryl group having from n to m ring carbon atoms. Aryl groups include, e.g., phenyl, naphthyl, anthracenyl, phenanthrenyl, indanyl, indenyl, and the like. In some embodiments, aryl groups have from 6 to 10 carbon atoms. In some embodiments, the aryl group is phenyl or naphthyl.

As used herein, "cycloalkyl" refers to non-aromatic cyclic hydrocarbons including cyclized alkyl and/or alkenyl groups. Cycloalkyl groups can include mono- or polycyclic (e.g., having 2, 3 or 4 fused rings) groups and spirocycles. Ring-forming carbon atoms of a cycloalkyl group can be optionally substituted by 1 or 2 independently selected oxo or sulfide groups (e.g., C(O) or C(S)). Also included in the definition of cycloalkyl are moieties that have one or more aromatic rings fused (i.e., having a bond in common with) to the cycloalkyl ring, for example, benzo or thienyl derivatives of cyclopentane, cyclohexane, and the like. A cycloalkyl group containing a fused aromatic ring can be attached through any ring-forming atom including a ring-forming atom of the fused aromatic ring. Cycloalkyl groups can have 3, 4, 5, 6, 7, 8, 9, or 10 ring-forming carbons ($C_{3-10}$). In some embodiments, the cycloalkyl is a $C_{3-10}$ monocyclic or bicyclic cycloalkyl. In some embodiments, the cycloalkyl is a $C_{3-7}$ monocyclic cycloalkyl. Example cycloalkyl groups include cyclopropyl, cyclobutyl, cyclopentyl, cyclohexyl, cycloheptyl, cyclopentenyl, cyclohexenyl, cyclohexadienyl, cycloheptatrienyl, norbornyl, norpinyl, norcarnyl, adamantyl, and the like. In some embodiments, cycloalkyl is cyclopropyl, cyclobutyl, cyclopentyl, or cyclohexyl.

As used herein, "heteroaryl" refers to a monocyclic or polycyclic aromatic heterocycle having at least one heteroatom ring member selected from sulfur, oxygen, and nitrogen. In some embodiments, the heteroaryl ring has 1, 2, 3, or 4 heteroatom ring members independently selected from nitrogen, sulfur and oxygen. In some embodiments, any ring-forming N in a heteroaryl moiety can be an N-oxide. In some embodiments, the heteroaryl is a 5-10 membered monocyclic or bicyclic heteroaryl having 1, 2, 3 or 4 heteroatom ring members independently selected from nitrogen, sulfur and oxygen. In some embodiments, the heteroaryl is a 5-6 monocyclic heteroaryl having 1 or 2 heteroatom ring members independently selected from nitrogen, sulfur and oxygen.

In some embodiments, the heteroaryl is a five-membered or six-membered heteroaryl ring. A five-membered heteroaryl ring is a heteroaryl with a ring having five ring atoms wherein one or more (e.g., 1, 2, or 3) ring atoms are independently selected from N, O, and S. Exemplary five-membered ring heteroaryls are thienyl, furyl, pyrrolyl, imidazolyl, thiazolyl, oxazolyl, pyrazolyl, isothiazolyl, isoxazolyl, 1,2,3-triazolyl, tetrazolyl, 1,2,3-thiadiazolyl, 1,2,3-oxadiazolyl, 1,2,4-triazolyl, 1,2,4-thiadiazolyl, 1,2,4-oxadiazolyl, 1,3,4-triazolyl, 1,3,4-thiadiazolyl, and 1,3,4-oxadiazolyl. A six-membered heteroaryl ring is a heteroaryl with a ring having six ring atoms wherein one or more (e.g., 1, 2, or 3) ring atoms are independently selected from N, O, and S. Exemplary six-membered ring heteroaryls are pyridyl, pyrazinyl, pyrimidinyl, triazinyl and pyridazinyl.

As used herein, "heterocycloalkyl" refers to non-aromatic monocyclic or polycyclic heterocycles having one or more ring-forming heteroatoms selected from O, N, or S. Included in heterocycloalkyl are monocyclic 4-, 5-, 6-, 7-, 8-, 9- or 10-membered heterocycloalkyl groups. Heterocycloalkyl groups can also include spirocycles. Example heterocycloalkyl groups include pyrrolidin-2-one, 1,3-isoxazolidin-2-one, pyranyl, tetrahydropyran, oxetanyl, azetidinyl, morpholino, thiomorpholino, piperazinyl, tetrahydrofuranyl, tetrahydrothienyl, piperidinyl, pyrrolidinyl, isoxazolidinyl, isothiazolidinyl, pyrazolidinyl, oxazolidinyl, thiazolidinyl, imidazolidinyl, azepanyl, benzazapene, and the like. Ring-forming carbon atoms and heteroatoms of a heterocycloalkyl group can be optionally substituted by 1 or 2 independently selected oxo or sulfido groups (e.g., C(O), S(O), C(S), or S(O)$_2$, etc.). The heterocycloalkyl group can be attached through a ring-forming carbon atom or a ring-forming heteroatom. In some embodiments, the heterocycloalkyl group contains 0 to 3 double bonds. In some embodiments, the heterocycloalkyl group contains 0 to 2 double bonds. Also included in the definition of heterocycloalkyl are moieties that have one or more aromatic rings fused (i.e., having a bond in common with) to the cycloalkyl ring, for example, benzo or thienyl derivatives of piperidine, morpholine, azepine, etc. A heterocycloalkyl group containing a fused aromatic ring can be attached through any ring-forming atom including a ring-forming atom of the fused aromatic ring. In some embodiments, the heterocycloalkyl is a monocyclic 4-6 membered heterocycloalkyl having 1 or 2 heteroatoms independently selected from nitrogen, oxygen, or sulfur and having one or more oxidized ring members. In some embodiments, the heterocycloalkyl is a monocyclic or bicyclic 4-10 membered heterocycloalkyl having 1, 2, 3, or 4 heteroatoms independently selected from nitrogen, oxygen, or sulfur and having one or more oxidized ring members.

At certain places, the definitions or embodiments refer to specific rings (e.g., an azetidine ring, a pyridine ring, etc.). Unless otherwise indicated, these rings can be attached to any ring member provided that the valency of the atom is not exceeded. For example, an azetidine ring may be attached at any position of the ring, whereas a pyridin-3-yl ring is attached at the 3-position.

As used herein, the term "oxo" refers to an oxygen atom as a divalent substituent, forming a carbonyl group when attached to a carbon (e.g., C=O), or attached to a heteroatom forming a sulfoxide or sulfone group.

The term "compound" as used herein is meant to include all stereoisomers, geometric isomers, tautomers, and isotopes of the structures depicted. Compounds herein identified by name or structure as one particular tautomeric form are intended to include other tautomeric forms unless otherwise specified.

The compounds described herein can be asymmetric (e.g., having one or more stereocenters). All stereoisomers, such as enantiomers and diastereomers, are intended unless otherwise indicated. Compounds of the present invention that contain asymmetrically substituted carbon atoms can be isolated in optically active or racemic forms. Methods on how to prepare optically active forms from optically inactive starting materials are known in the art, such as by resolution of racemic mixtures or by stereoselective synthesis. Many geometric isomers of olefins, C=N double bonds, N=N double bonds, and the like can also be present in the compounds described herein, and all such stable isomers are contemplated in the present invention. Cis and trans geometric isomers of the compounds of the present invention are described and may be isolated as a mixture of isomers or as separated isomeric forms. In some embodiments, the compound has the (R)-configuration. In some embodiments, the compound has the (S)-configuration.

Compounds provided herein also include tautomeric forms. Tautomeric forms result from the swapping of a single bond with an adjacent double bond together with the concomitant migration of a proton. Tautomeric forms include prototropic tautomers which are isomeric protonation states having the same empirical formula and total charge. Example prototropic tautomers include ketone-enol pairs, amide-imidic acid pairs, lactam-lactim pairs, enamine-imine pairs, and annular forms where a proton can occupy two or more positions of a heterocyclic system, for example, 1H- and 3H-imidazole, 1H-, 2H- and 4H-1,2,4-triazole, 1H- and 2H-isoindole, and 1H- and 2H-pyrazole. Tautomeric forms can be in equilibrium or sterically locked into one form by appropriate substitution.

As used herein, the term "cell" is meant to refer to a cell that is in vitro, ex vivo or in vivo. In some embodiments, an ex vivo cell can be part of a tissue sample excised from an organism such as a mammal. In some embodiments, an in vitro cell can be a cell in a cell culture. In some embodiments, an in vivo cell is a cell living in an organism such as a mammal. In some embodiments, the cell is a red blood cell. In some embodiments, the cell is a myocardial cell. In some embodiments, the cell is a nerve cell (e.g., a neuron).

As used herein, the term "contacting" refers to the bringing together of indicated moieties in an in vitro system or an in vivo system. For example, "contacting" the MIF with a compound of the invention includes the administration of a compound of the present invention to an individual or patient, such as a human, having MIF, as well as, for example, introducing a compound of the invention into a sample containing a cellular or purified preparation containing the MIF.

As used herein, the term "individual", "patient", or "subject" used interchangeably, refers to any animal, including mammals, preferably mice, rats, other rodents, rabbits, dogs, cats, swine, cattle, sheep, horses, or primates, and most preferably humans.

As used herein, the phrase "effective amount" or "therapeutically effective amount" refers to the amount of active compound or pharmaceutical agent that elicits the biological or medicinal response in a tissue, system, animal, individual or human that is being sought by a researcher, veterinarian, medical doctor or other clinician.

As used herein the term "treating" or "treatment" refers to 1) inhibiting the disease; for example, inhibiting a disease, condition or disorder in an individual who is experiencing or displaying the pathology or symptomatology of the disease, condition or disorder (i.e., arresting further development of the pathology and/or symptomatology), or 2) ameliorating the disease; for example, ameliorating a disease, condition or disorder in an individual who is experiencing or displaying the pathology or symptomatology of the disease, condition or disorder (i.e., reversing the pathology and/or symptomatology).

As used herein, the term "preventing" or "prevention" of a disease, condition or disorder refers to decreasing the risk of occurrence of the disease, condition or disorder in a subject or group of subjects (e.g., a subject or group of subjects predisposed to or susceptible to the disease, condition or disorder). In some embodiments, preventing a disease, condition or disorder refers to decreasing the possibility of acquiring the disease, condition or disorder and/or its associated symptoms. In some embodiments, preventing a disease, condition or disorder refers to completely or almost completely stopping the disease, condition or disorder from occurring.

EXAMPLES

Example 1—N-((3-(4-(benzo[d]isothiazol-3-yl)piperazine-1-carbonyl)pyrazolo[1,5-a]pyridin-5-yl)methyl)cyclopropanecarboxamide

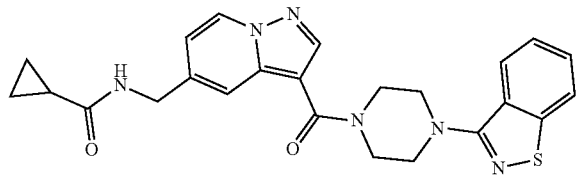 [SMILES: O=C(NCc1ccn2ncc(C(=O)N3CCN(c4nsc5ccccc45)CC3)c2c1)C1CC1]

MP 124-126° C. Found (%): C, 62.46; H, 5.37, N, 18.41, S, 7.16. $C_{24}H_{24}N_6O_2S$. Calculated (%): C, 62.59; H, 5.25, N, 18.25, O, 6.95, S, 6.96. $^1H$ NMR (300 MHz, CDCl$_3$, δ) 0.69-0.73 (m, 2H); 0.91-0.95 (m, 2H); 1.19-1.21 (m, 1H); 3.29-3.31 (m, 4H); 3.81-3.85 (m, 4H); 4.21-4.24 (m, 2H); 6.79-6.81 (m, 1H); 7.26-7.28 (m, 1H); 7.49 (s, 1H); 7.73-7.80 (m, 2H); 8.10-8.25 (m, 2H); 8.39-8.43 (m, 2H). (ESI, m/z): 461.1754 (found); 461.1746 (calculated).

Example 2—1-(4-(phenylamino)phenyl)-3-((3-(1,2,3,4-tetrahydroisoquinoline-2-carbonyl)pyrazolo[1,5-a]pyridin-5-yl)methyl)thiourea

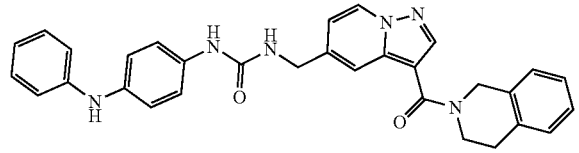 [SMILES: O=C(NCc1ccn2ncc(C(=O)N3CCc4ccccc4C3)c2c1)Nc1ccc(Nc2ccccc2)cc1]

MP 175-177° C. Found (%): C, 69.86; H, 5.41, N, 15.90, S, 6.27. $C_{31}H_{28}N_6OS$. Calculated (%): C, 69.90; H, 5.30, N, 15.78, O, 3.00, S, 6.02. $^1H$ NMR (300 MHz, CDCl$_3$, δ) 2.01-2.03 (m, 1H); 3.11-3.18 (m, 2H); 3.62-3.65 (m, 2H); 4.03-4.05 (m, 2H); 4.22-4.23 (m, 2H); 4.69-4.70 (m, 2H); 6.20-6.22 (m, 2H); 6.34-6.37 (m, 2H); 6.73-6.75 (m, 1H); 6.79-6.81 (m, 1H); 7.19-7.25 (m, 4H); 7.43-7.54 (m, 3H); 7.79-7.81 (m, 1H); 8.39-8.40 (m, 1H). Mass spectrum (ESI, m/z): 533.2109 (found); 533.2118 (calculated).

Example 3—N-benzyl-5-((3-phenylureido)methyl)pyrazolo[1,5-a]pyridine-3-carboxamide

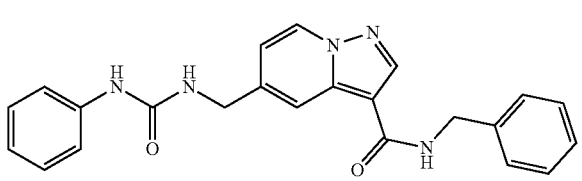 [SMILES: O=C(NCc1ccn2ncc(C(=O)NCc3ccccc3)c2c1)Nc1ccccc1]

MP 242-244° C. Found (%): C, 69.03; H, 5.41; N, 17.64. $C_{23}H_{21}N_5O_2$. Calculated (%): C, 69.16; H, 5.30; N, 17.53; 0, 8.01. NMR $^1H$ (300 MHz, CDCl$_3$, δ) 4.11-4.15 (m, 2H); 4.21-4.25 (m, 2H); 6.09-6.15 (m, 2H); 6.70-6.74 (m, 1H); 7.19-7.39 (m, 6H); 7.20-7.27 (m, 4H); 7.31-7.34 (m, 2H); 7.42-7.45 (m, 2H); 7.52-7.63 (m, 3H); 7.83-7.86 (m, 1H); 8.39-8.41 (m, 1H). Mass spectrum (ESI, m/z): 400.1760 (found); 400.1768 (calculated).

Example 4—1-((3-(1,2,3,4-tetrahydroisoquinoline-2-carbonyl)pyrazolo[1,5-a]pyridin-5-yl)methyl)-3-(m-tolyl)urea

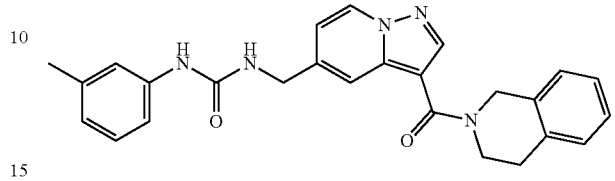

MP 223-225° C. Found (%): C, 70.94; H, 5.88, N, 16.07. $C_{26}H_{25}N_5O_2$. Calculated (%): C, 71.05; H, 5.73, N, 15.93, O, 7.28. $^1H$ NMR (300 MHz, CDCl$_3$, δ) 2.29 (s, 3H); 3.06-3.09 (m, 2H); 3.46-3.51 (m, 2H); 4.15-4.27 (m, 4H); 6.12-6.17 (m, 2H); 6.72-6.74 (m, 1H); 7.02-7.09 (m, 1H); 7.15-7.25 (m, 3H); 7.37-7.43 (m, 3H); 7.51-7.79 (m, 3H); 8.31-8.37 (m, 1H). Mass spectrum (ESI, m/z): 533.2109 (found); 533.2118 (calculated).

Example 5—1-(3-chlorophenyl)-3-((3-(1,2,3,4-tetrahydroisoquinoline-2-carbonyl)pyrazolo[1,5-a]pyridin-5-yl)methyl)urea

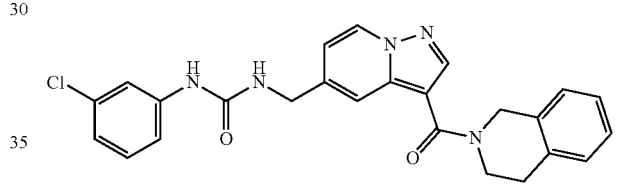

MP 225-227° C. Found (%): C, 65.15; H, 4.96; Cl, 7.87; N, 15.36. $C_{25}H_{22}ClN_5O_2$. Calculated (%): C, 65.29; H, 4.82; Cl, 7.71; N, 15.23; 0, 6.96. $^1H$ NMR (300 MHz, CDCl$_3$, δ) 3.10-3.13 (m, 2H); 3.47-3.53 (m, 2H); 4.19-4.3 (m, 4H); 6.10-6.18 (m, 2H); 6.69-6.72 (m, 1H); 7.10-7.16 (m, 1H); 7.15-7.25 (m, 3H); 7.37-7.43 (m, 2H); 7.51-7.79 (m, 3H); 8.31-8.37 (m, 2H). Mass spectrum (ESI, m/z): 460.1525 (found); 460.1535 (calculated).

Example 6—N-benzyl-5-((3-(3,4-dichlorophenyl)ureido)methyl)pyrazolo[1,5-a]pyridine-3-carboxamide

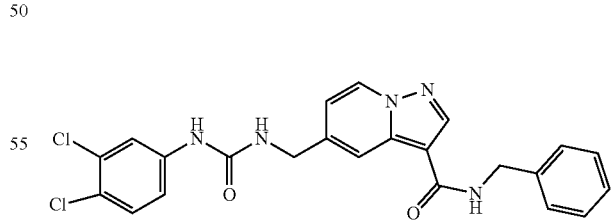

MP 230-232° C. Found (%): C, 58.85; H, 4.21; Cl, 15.29; N, 15.17. $C_{23}H_{19}Cl_2N_5O_2$. Calculated (%): C, 58.98; H, 4.09; Cl, 15.14; N, 14.95; 0, 6.83. $^1H$ NMR (300 MHz, CDCl$_3$, δ) 4.07-4.10 (m, 2H); 4.18-4.22 (m, 2H); 6.09-6.15 (m, 2H); 6.71-6.75 (m, 1H); 7.19-7.39 (m, 6H); 7.47-7.91 (m, 4H); 8.00-8.05 (m, 1H); 8.37-8.39 (m, 1H). Mass spectrum (ESI, m/z): 468.0982 (found); 468.0989 (calculated).

Examples 7-27

The following compounds were prepared according to the synthetic methods and procedures described in this disclosure and show in Schemes 1 and 2.

| No. | Compound structure | Chemical name |
| --- | --- | --- |
| 7 | 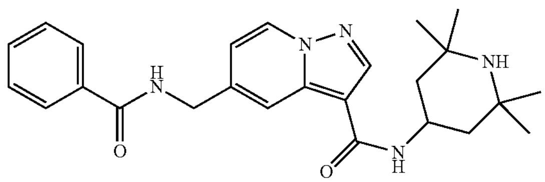 [SMILES: CC1(C)CC(NC(=O)c2cnn3ccc(CNC(=O)c4ccccc4)cc23)CC(C)(C)N1] | 5-(benzamidomethyl)-N-(2,2,6,6-tetramethylpiperidin-4-yl)pyrazolo[1,5-a]pyridine-3-carboxamide |
| 8 | 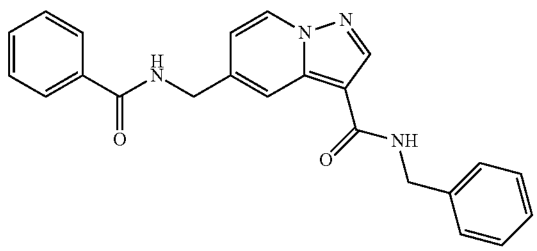 [SMILES: O=C(NCc1ccn2ncc(C(=O)NCc3ccccc3)c2c1)c1ccccc1] | 5-(benzamidomethyl)-N-benzylpyrazolo[1,5-a]pyridine-3-carboxamide |
| 9 | 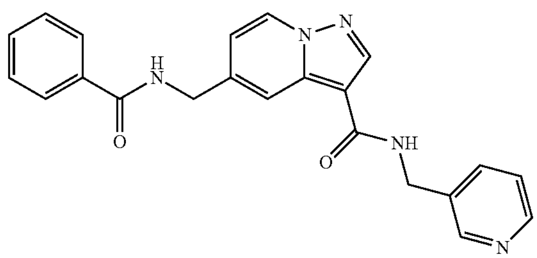 [SMILES: O=C(NCc1ccn2ncc(C(=O)NCc3cccnc3)c2c1)c1ccccc1] | 5-(benzamidomethyl)-N-(pyridin-3-ylmethyl)pyrazolo[1,5-a]pyridine-3-carboxamide |
| 10 | 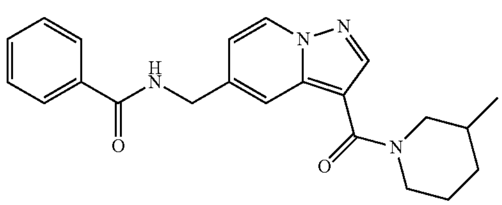 [SMILES: CC1CCCN(C(=O)c2cnn3ccc(CNC(=O)c4ccccc4)cc23)C1] | N-((3-(3-methylpiperidine-1-carbonyl)pyrazolo[1,5-a]pyridin-5-yl)methyl)benzamide |
| 11 | 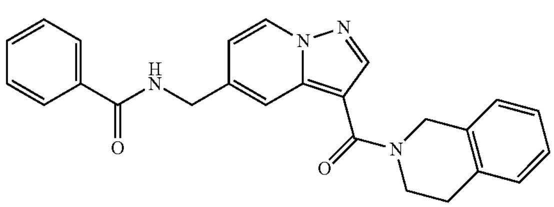 [SMILES: O=C(NCc1ccn2ncc(C(=O)N3CCc4ccccc4C3)c2c1)c1ccccc1] | N-((3-(1,2,3,4-tetrahydroisoquinoline-2-carbonyl)pyrazolo[1,5-a]pyridin-5-yl)methyl)benzamide |
| 12 | 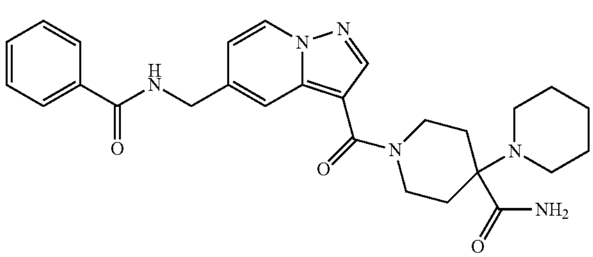 [SMILES: NC(=O)C1(N2CCCCC2)CCN(C(=O)c2cnn3ccc(CNC(=O)c4ccccc4)cc23)CC1] | 1'-(5-(benzamidomethyl)pyrazolo[1,5-a]pyridine-3-carbonyl)-[1,4'-bipiperidine]-4'-carboxamide |

-continued

| No. | Compound structure | Chemical name |
|---|---|---|
| 13 | 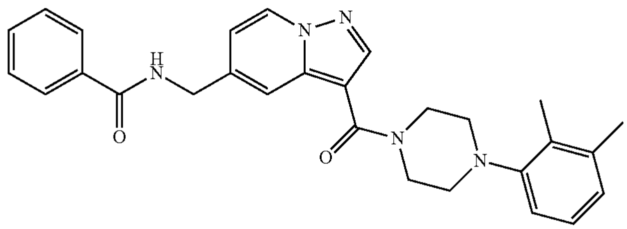 [SMILES: Cc1cccc(N2CCN(C(=O)c3cnn4ccc(CNC(=O)c5ccccc5)cc34)CC2)c1C] | N-((3-(4-(2,3-dimethylphenyl)piperazine-1-carbonyl)pyrazolo[1,5-a]pyridin-5-yl)methyl)benzamide |
| 14 | 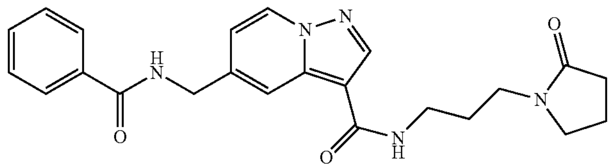 [SMILES: O=C(NCc1ccn2ncc(C(=O)NCCCN3CCCC3=O)c2c1)c1ccccc1] | 5-(benzamidomethyl)-N-(3-(2-oxopyrrolidin-1-yl)propyl)pyrazolo[1,5-a]pyridine-3-carboxamide |
| 15 | 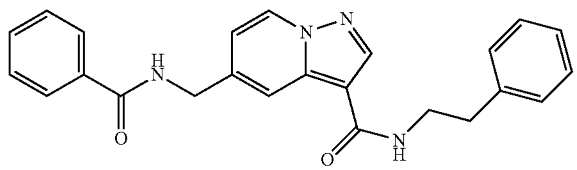 [SMILES: O=C(NCc1ccn2ncc(C(=O)NCCc3ccccc3)c2c1)c1ccccc1] | 5-(benzamidomethyl)-N-phenethylpyrazolo[1,5-a]pyridine-3-carboxamide |
| 16 | 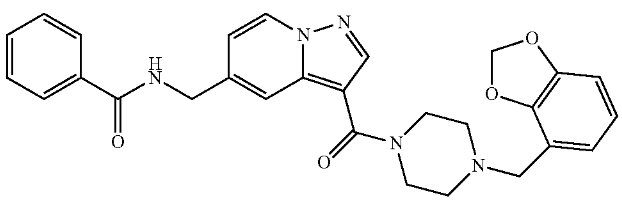 [SMILES: O=C(NCc1ccn2ncc(C(=O)N3CCN(Cc4cccc5c4OCO5)CC3)c2c1)c1ccccc1] | N-((3-(4-(benzo[d][1,3]dioxol-4-ylmethyl)piperazine-1-carbonyl)pyrazolo[1,5-a]pyridin-5-yl)methyl)benzamide |
| 17 | 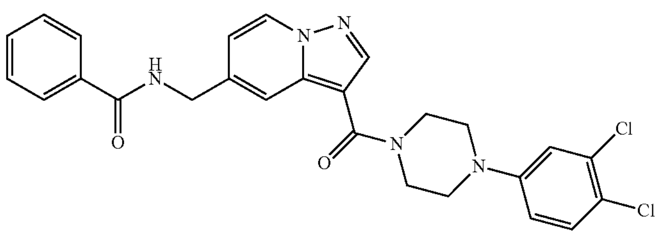 [SMILES: O=C(NCc1ccn2ncc(C(=O)N3CCN(c4ccc(Cl)c(Cl)c4)CC3)c2c1)c1ccccc1] | N-((3-(4-(3,4-dichlorophenyl)piperazine-1-carbonyl)pyrazolo[1,5-a]pyridin-5-yl)methyl)benzamide |
| 18 | 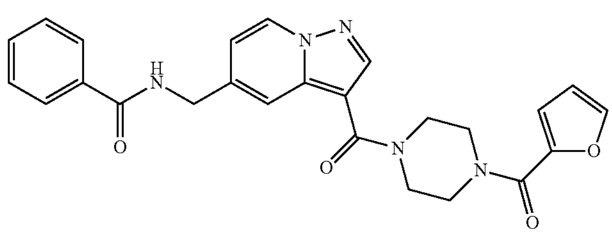 [SMILES: O=C(NCc1ccn2ncc(C(=O)N3CCN(C(=O)c4ccco4)CC3)c2c1)c1ccccc1] | N-((3-(4-(furan-2-carbonyl)piperazine-1-carbonyl)pyrazolo[1,5-a]pyridin-5-yl)methyl)benzamide |
| 19 | 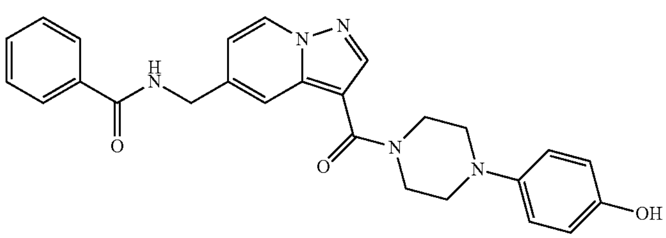 [SMILES: O=C(NCc1ccn2ncc(C(=O)N3CCN(c4ccc(O)cc4)CC3)c2c1)c1ccccc1] | N-((3-(4-(4-hydroxyphenyl)piperazine-carbonyl)pyrazolo[1,5-a]pyridin-5-yl)methyl)benzamide |

| No. | Compound structure | Chemical name |
|---|---|---|
| 20 | 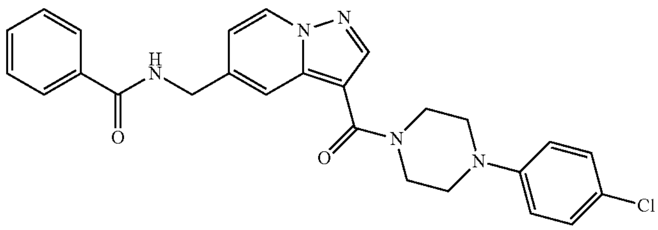 [SMILES: O=C(NCc1ccn2ncc(C(=O)N3CCN(c4ccc(Cl)cc4)CC3)c2c1)c1ccccc1] | N-((3-(4-(4-chlorophenyl)piperazine-1-carbonyl)pyrazolo[1,5-a]pyridin-5-yl)methyl)benzamide |
| 21 | 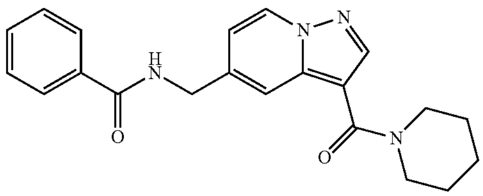 [SMILES: O=C(NCc1ccn2ncc(C(=O)N3CCCCC3)c2c1)c1ccccc1] | N-((3-(piperidine-1-carbonyl)pyrazolo[1,5-a]pyridin-5-yl)methyl)benzamide |
| 22 | 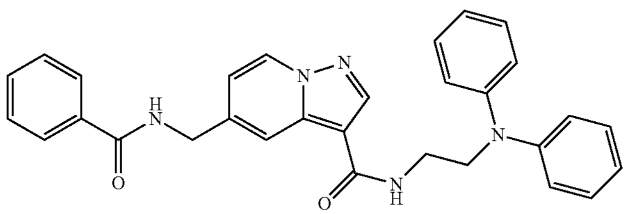 [SMILES: O=C(NCc1ccn2ncc(C(=O)NCCN(c3ccccc3)c3ccccc3)c2c1)c1ccccc1] | 5-(benzamidomethyl)-N-(2-(diphenylamino)ethyl)pyrazolo[1,5-a]pyridine-3-carboxamide |
| 23 | 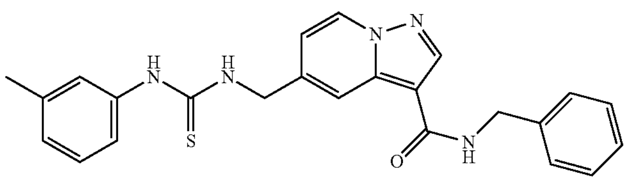 [SMILES: Cc1cccc(NC(=S)NCc2ccn3ncc(C(=O)NCc4ccccc4)c3c2)c1] | N-benzyl-5-((3-(m-tolyl)thioureido)methyl)pyrazolo[1,5-a]pyridine-3-carboxamide |
| 24 | 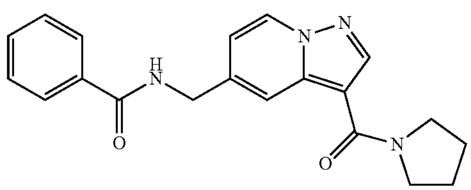 [SMILES: O=C(NCc1ccn2ncc(C(=O)N3CCCC3)c2c1)c1ccccc1] | N-((3-(pyrrolidine-1-carbonyl)pyrazolo[1,5-a]pyridin-5-yl)methyl)benzamide |
| 25 | 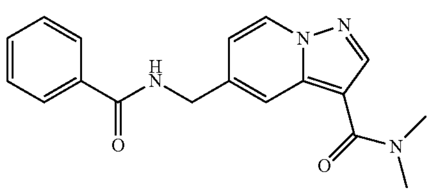 [SMILES: CN(C)C(=O)c1cnn2ccc(CNC(=O)c3ccccc3)cc12] | 5-(benzamidomethyl)-N,N-dimethylpyrazolo[1,5-a]pyridine-3-carboxamide |
| 26 | 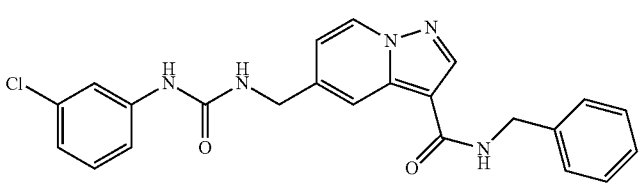 [SMILES: O=C(NCc1ccn2ncc(C(=O)NCc3ccccc3)c2c1)Nc1cccc(Cl)c1] | N-benzyl-5-((3-(3-chlorophenyl)ureido)methyl)pyrazolo[1,5-a]pyridine-3-carboxamide |

| No. | Compound structure | Chemical name |
|---|---|---|
| 27 | 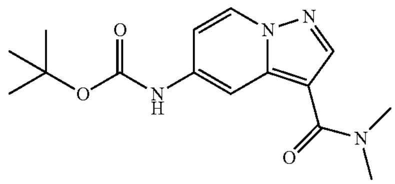 [SMILES: CN(C)C(=O)c1cnn2ccc(NC(=O)OC(C)(C)C)cc12] | tert-butyl (3-(dimethylcarbamoyl)pyrazolo[1,5-a]pyridin-5-yl)carbamate |

Example 28—Biological Activity of Exemplified Compounds $EC_{50}$ for exemplified compounds against huMIF and PfMIF are shown in Table 1.

TABLE 1

| No. | NP code | $EC_{50}$, µM |
|---|---|---|
| 1 | NP-F-0055 | |
| 2 | NP-F-2419 | 2.192 |
| 3 | NP-F-3758 | 58.32 |
| 4 | NP-F-3847 | 36.96 |
| 5 | NP-F-4119 | 4.163 |
| 6 | NP-F-4234 | 64.40 |
| 7 | NP-F-0412 | 223.1 |
| 8 | NP-F-0426 | 61.63 |
| 9 | NP-F-0432 | 95.45 |
| 10 | NP-F-0448 | 77.87 |
| 11 | NP-F-0447 | 40.05 |
| 12 | NP-F-0457 | 129.4 |
| 13 | NP-F-0411 | 30.78 |
| 14 | NP-F-0422 | 141.6 |
| 15 | NP-F-0427 | 34.18 |
| 16 | NP-F-0433 | 33.48 |
| 17 | NP-F-0444 | 38.26 |
| 18 | NP-F-0455 | 31.63 |
| 19 | NP-F-0458 | 71.68 |
| 20 | NP-F-0460 | 13.53 |
| 21 | NP-F-0465 | 59.49 |
| 22 | NP-F-0475 | 85.79 |
| 23 | NP-F-4051 | 10.65 |
| 24 | NP-F-0464 | 105.9 |
| 25 | NP-F-0469 | 88.27 |
| 26 | NP-F-4098 | 70.07 |
| 27 | NP-A-0981 | 146.0 |

Example 29—Invasion Assay

FIG. 1 shows results of invasion assay in the presence of compounds of Example 13, Example 5, and Example 4. Experimental protocol: Synchronized late-stage schizonts were added at 1% initial parasitemia to uninfected recipient normal RBCs and parasitemia was measured by FACS. Parasitemia is normalized to the control no-inhibitor condition. Data analyzed by one-way ANOVA. Statistically significant differences are indicated with a star over the bar. Asterisk (*) indicates $p<0.01$ compared to control (no-inhibitor).

Example 30

Figure 2:
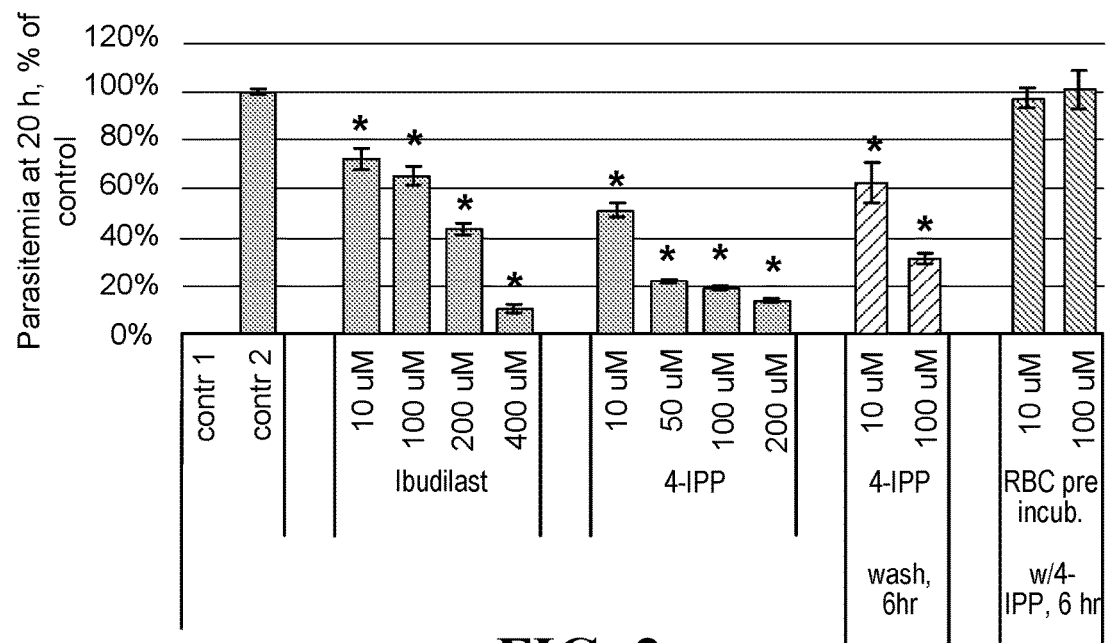
FIG. 2 contains bar graphs showing results of invasion assay in presence of titrated amounts of ibudilast and 4-IPP FIG. 3 contains images showing results of treatment of P. falciparum (Pf)-infected red blood cells (RBCs) with protease inhibitors E-64 and leupeptin, and with MIF inhibitor 4-IPP.

FIG. 2 describes results of invasion assay in presence of titrated amounts of MIF inhibitors. Ibudilast (inhibitor of MIF and PDE4) and 4-IPP (MIF inhibitor) reduced parasitemia up to 90% at dosages comparable to the currently prescribed regimen of ibudilast. All data is normalized to the control no-inhibitor condition. Removal of 4-IPP 6 h post-infection did not recover the parasitemia, while treating only the recipient RBCs for 3 h and 6 h followed by washing of 4-IPP before infection showed parasitemia at the level of the control condition. Asterisk (*) indicates $p<0.01$ compared to control (no-inhibitor).

Ibudilast and 4-IPP significantly lowered parasitemia in vitro suggesting that their target(s) may be essential for supporting parasite development (FIG. 2; representative of more than 4 experiments). P. falciparum strain NF54 attB parasites (Dr. Niles, MIT). Synchronized late-stage schizonts were added at 1% initial parasitemia to uninfected recipient normal RBCs and parasitemia was measured by FACS (FIG. 2). The parasitemia was significantly and progressively decreased as the amount of inhibitor increased. Given that ibudilast has inhibitory effect on the function of MIF as well as phosphodiesterase 4 (PDE4) in the RBC, it was evaluated whether specific inhibitors of MIF and PDE4 would cause major decline in parasitemia at similar dosages. While inhibition of parasite growth was not observed due to abolishing the function of PDE4 (data not shown), inhibition of the tautomerase activity of MIF in vitro by an irreversible inhibitor of MIF—4-IPP—caused a significant decline in the levels of parasitemia (FIG. 2). These results suggest that the inhibitory effect of ibudilast on P. falciparum parasitemia is related to its effect on MIF activity. Further, pretreatment of healthy, target RBC with 4-IPP for 6 h prior to infection, did not reduce parasitemia levels (FIG. 2), suggesting that the target of the 4-IPP activity may be the Pf-MIF but not the hu-MIF. Consistently, another MIF inhibitor, ISO-1, which is exclusively specific to the human (hu)-MIF but not P. falciparum (Pf)-MIF, did not reduce the invasion at a range of concentrations (data not shown). Moreover, invasion assay in presence of exogenous hu-MIF did not show reduced or increased parasitemia compared to control conditions even when the cells were preincubated with huMIF for up to 6 h (data not shown). In addition, FACS analysis of infected RBC cultures treated with 4-IPP showed significant increase in the percentage of mature schizont at 48 to 60 hours post infection (hpi), suggestive of a blockade egress (data not shown). Further experiments revealed no recovery of invasion upon removal of 4-IPP 6 hpi (FIG. 2), illustrating that the lowered parasitemia is likely not due to temporary developmental arrest of the schizont-stage P. falciparum.

Figure 3:
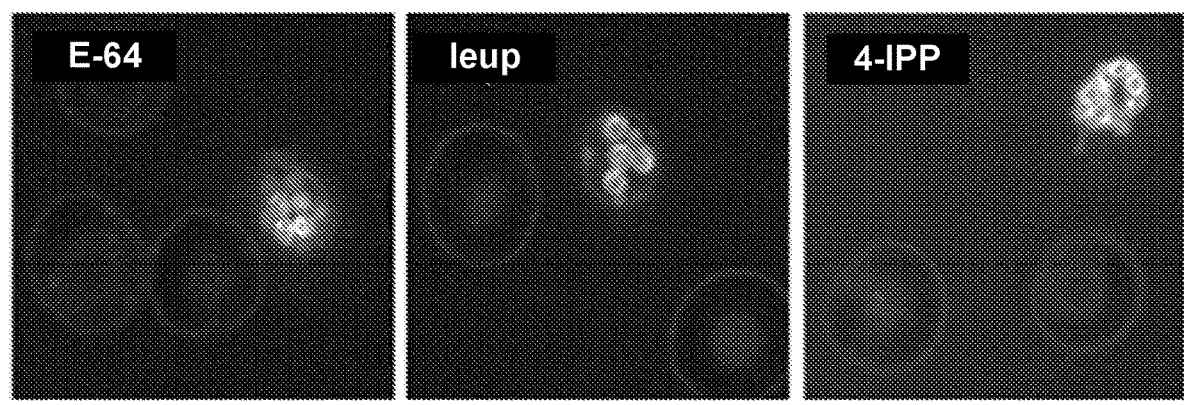

FIG. 3 shows results of treatment of Pf-infected RBCs with protease inhibitors E-64 and leupeptin, which block parasite egress, and with MIF inhibitor 4-IPP, followed by BODIPY™ TR lipophilic intracellular staining. One plane of confocal microscopy z-stack is shown. The data indicate that the mature schizonts remain encapsulated when treated with ibudilast (data not shown) or 4-IPP (FIG. 3).

REFERENCES

1. Cho, Y., et al. (2010) Allosteric inhibition of macrophage migration inhibitory factor revealed by ibudilast. *Proc Natl Acad Sci USA* 107, 11313-11318

2. Kawasaki, A., et al. (1992) Effect of ibudilast: a novel antiasthmatic agent, on airway hypersensitivity in bronchial asthma. *J Asthma* 29, 245-252
3. Kishi, Y., et al. (2001) Ibudilast: a non-selective PDE inhibitor with multiple actions on blood cells and the vascular wall. *Cardiovasc Drug Rev* 19, 215-225
4. Fox, R. J., et al. (2016) Design, rationale, and baseline characteristics of the randomized double-blind phase II clinical trial of ibudilast in progressive multiple sclerosis. *Contemp Clin Trials* 50, 166-177
5. Fox, R. J., et al. (2018) Phase 2 Trial of Ibudilast in Progressive Multiple Sclerosis. *N Engl J Med* 379, 846-855
6. Cooper, Z. D., et al. (2017) Effects of ibudilast on oxycodone-induced analgesia and subjective effects in opioid-dependent volunteers. *Drug Alcohol Depend* 178, 340-347
7. Cooper, Z. D., et al. (2016) The effects of ibudilast, a glial activation inhibitor, on opioid withdrawal symptoms in opioid-dependent volunteers. *Addict Biol* 21, 895-903
8. Metz, V. E., et al. (2017) Effects of Ibudilast on the Subjective, Reinforcing, and Analgesic Effects of Oxycodone in Recently Detoxified Adults with Opioid Dependence. *Neuropsychopharmacology* 42, 1825-1832
9. Schwenkgrub, J., et al. (2017) The phosphodiesterase inhibitor, ibudilast, attenuates neuroinflammation in the MPTP model of Parkinson's disease. *PLoS One* 12, e0182019
10. Walters, E. T. (2014) Neuroinflammatory contributions to pain after SCI: roles for central glial mechanisms and nociceptor-mediated host defense. *Exp Neurol* 258, 48-61
11. Nobre, C., et al. (2017) Macrophage Migration Inhibitory Factor (MIF): Biological Activities and Relation with Cancer, *Pathol. Oncol. Res.* 23, 235-244
12. Tilstam, P., et al. (2017) MIF family cytokines in cardiovascular diseases and prospects for precision-based therapeutics, *Expert Opin Ther Targets.* 21 (7), 671-683
13. Sparkes, A., et al. (2017) Reprint of: The non-mammalian MIF superfamily, *Immunobiology* 222 (3), 473-482
14. Leyton-Jaimes, M., et al., Macrophage migration inhibitory factor: A multifaceted cytokine implicated in multiple neurological diseases, *Experimental Neurology* 301, 83-91
15. Holowka T, et al., *Leishmania*-encoded orthologs of macrophage migration inhibitory factor regulate host immunity to promote parasite persistence. *FASEB J.* 2016, 30 (6), 2249-2265.
16. Kamir D, et al., A *Leishmania* ortholog of macrophage migration inhibitory factor modulates host macrophage responses. *J Immunol.* 2008, 180 (12), 8250-8261.
17. Richardson J., et al., Structures of *Leishmania major* orthologues of macrophage migration inhibitory factor. *Biochem Biophys Res Commun.* 2009, 380 (3), 442-448
18. Liu K, et al., Protective Effect Against Toxoplasmosis in BALB/c Mice Vaccinated With *Toxoplasma gondii* Macrophage Migration Inhibitory Factor. Front Microbiol. 2019, 10, 813
19. Buchko, G. et. al., Sequence of Gl-MIF and the other Crystal structure of a macrophage migration inhibitory factor from *Giardia lamblia*, J Struct Funct Genomics. 2013, 14 (2), 47-57

OTHER EMBODIMENTS

It is to be understood that while the present application has been described in conjunction with the detailed description thereof, the foregoing description is intended to illustrate and not limit the scope of the present application, which is defined by the scope of the appended claims. Other aspects, advantages, and modifications are within the scope of the following claims.

What is claimed is:
1. A compound of formula (I):

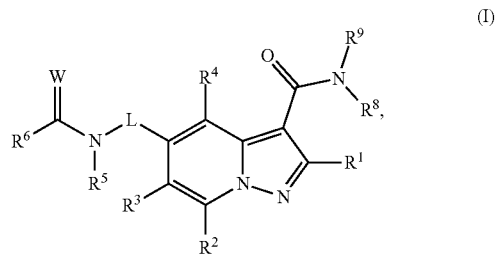

or a pharmaceutically acceptable salt thereof, wherein:
$R^1$, $R^2$, $R^3$, and $R^4$ are each independently selected from H, halo, CN, $NO_2$, $C_{1-6}$ alkyl, $C_{1-6}$ haloalkyl, $C_{2-6}$ alkenyl, $C_{2-6}$ alkynyl, $OR^{a1}$, $C(O)R^{b1}$, $C(O)NR^{c1}R^{d1}$, $C(O)OR^{a1}$, $NR^{c1}R^{d1}$, $NR^{c1}C(O)R^{b1}$, $NR^{c1}C(O)OR^{a1}$, $NR^{c1}S(O)_2R^{b1}$, $S(O)_2R^{b1}$, and $S(O)_2NR^{c1}R^{d1}$, wherein said $C_{1-6}$ alkyl, $C_{2-6}$ alkenyl, and $C_{2-6}$ alkynyl are each optionally substituted with 1, 2, or 3 substituents independently selected from CN, $NO_2$, $OR^{a1}$, $C(O)R^{b1}$, $C(O)NR^{c1}R^{d1}$, $C(O)OR^{a1}$, $NR^{c1}R^{d1}$, $NR^{c1}C(O)R^{b1}$, $NR^{c1}C(O)OR^{a1}$, $NR^{c1}S(O)_2R^{b1}$, $S(O)_2R^{b1}$, and $S(O)_2NR^{c1}R^{d1}$;

L is selected from $C_{1-3}$ alkylene, $C_{2-4}$ alkenylene, and $C_{2-4}$ alkynylene, each of which is optionally substituted with 1, 2, or 3 substituents independently selected from OH, $NO_2$, CN, halo, $C_{1-6}$ alkoxy, and $C_{1-6}$ haloalkoxy;

$R^6$ is selected from Cy and X-Cy;

X is selected from O, S, and $NR^7$;

$R^5$, $R^7$, and $R^8$ are each independently selected from H and $C_{1-3}$ alkyl;

W is selected from O and S;

$R^9$ is selected from $C_{1-6}$ alkyl, $C_{1-6}$ haloalkyl, $C_{2-6}$ alkenyl, $C_{2-6}$ alkynyl, $Cy^1$, $C(O)R^{b1}$, $C(O)NR^{c1}R^{d1}$, $C(O)OR^{a1}$, $S(O)_2R^{b1}$, and $S(O)_2NR^{c1}R^{d1}$, wherein said $C_{1-6}$ alkyl, $C_{2-6}$ alkenyl, and $C_{2-6}$ alkynyl are each optionally substituted with 1, 2, or 3 substituents independently selected from $Cy^1$, CN, $NO_2$, $OR^{a1}$, $C(O)R^{b1}$, $C(O)NR^{c1}R^{d1}$, $C(O)OR^{a1}$, $NR^{c1}R^{d1}$, $NR^{c1}C(O)R^{b1}$, $NR^{c1}C(O)OR^{a1}$, $NR^{c1}S(O)_2R^{b1}$, $S(O)_2R^{b1}$, and $S(O)_2NR^{c1}R^{d1}$, or $R^8$ and $R^9$, together with the N atom to which they are attached, form a 4-10 membered heterocycloalkyl ring, which is optionally substituted with 1, 2, or 3 substituents independently selected from $R^{Cy1}$;

Cy is selected from $C_{6-10}$ aryl, $C_{3-10}$ cycloalkyl, 5-14 membered heteroaryl, and 4-10 membered heterocycloalkyl, each of which is optionally substituted with 1, 2, or 3 substituents independently selected from $R^{Cy1}$;

$Cy^1$ is selected from $C_{6-10}$ aryl, $C_{3-10}$ cycloalkyl, 5-14 membered heteroaryl, and 4-10 membered heterocycloalkyl, each of which is optionally substituted with 1, 2, or 3 substituents independently selected from $R^{Cy1}$;

each $R^{Cy1}$ is independently selected from halo, CN, $NO_2$, $Cy^2$, $C_{1-6}$ alkyl, $C_{1-6}$ haloalkyl, $C_{2-6}$ alkenyl, $C_{2-6}$ alkynyl, $OR^{a2}$, $SR^{a2}$, $C(O)R^{b2}$, $C(O)NR^{c2}R^{d2}$, $C(O)OR^{a2}$, $NR^{c2}R^{d2}$, $NR^{c2}C(O)R^{b2}$, $NR^{c2}C(O)OR^{a2}$, $NR^{c2}S(O)_2R^{b2}$, $S(O)_2R^{b2}$, and $S(O)_2NR^{c2}R^{d2}$, wherein said $C_{1-6}$ alkyl, $C_{2-6}$ alkenyl, and $C_{2-6}$ alkynyl are each optionally substituted with 1, 2, or 3 substituents independently selected from $Cy^2$, halo, CN, $NO_2$, $OR^{a2}$, $C(O)R^{b2}$, $C(O)NR^{c2}R^{d2}$, $C(O)OR^{a2}$, $NR^{c2}R^{d2}$, $NR^{c2}C(O)R^{b2}$, $NR^{c2}C(O)OR^{a2}$, $NR^{c2}S(O)_2R^{b2}$, $S(O)_2R^{b2}$, and $S(O)_2NR^{c2}R^{d2}$;

each $Cy^2$ is independently selected from $C_{6-10}$ aryl, $C_{3-10}$ cycloalkyl, 5-10 membered heteroaryl, and 4-10 membered heterocycloalkyl, each of which is optionally substituted with 1, 2, or 3 substituents independently selected from $R^{Cy2}$;

each $R^{Cy2}$ is independently selected from halo, CN, $NO_2$, $C_{1-6}$ alkyl, $C_{1-6}$ haloalkyl, $C_{2-6}$ alkenyl, $C_{2-6}$ alkynyl, $OR^{a2}$, $C(O)R^{b2}$, $C(O)NR^{c2}R^{d2}$, $C(O)OR^{a2}$, $NR^{c2}R^{d2}$, $NR^{c2}C(O)R^{b2}$, $NR^{c2}C(O)OR^{a2}$, $NR^{c2}S(O)_2R^{b2}$, $S(O)_2R^{b2}$, and $S(O)_2NR^{c2}R^{d2}$; wherein said $C_{1-6}$ alkyl, $C_{2-6}$ alkenyl, and $C_{2-6}$ alkynyl are each optionally substituted with 1, 2, or 3 substituents independently selected from halo, CN, $NO_2$, $OR^{a2}$, $C(O)R^{b2}$, $C(O)NR^{c2}R^{d2}$, $C(O)OR^{a2}$, $NR^{c2}R^{d2}$, $NR^{c2}C(O)R^{b2}$, $NR^{c2}C(O)OR^{a2}$, $NR^{c2}S(O)_2R^{b2}$, $S(O)_2R^{b2}$, and $S(O)_2NR^{c2}R^{d2}$;

each $R^{a1}$, $R^{b1}$, $R^{c1}$, $R^{d1}$, $R^{a2}$, $R^{b2}$, $R^{c2}$, and $R^{d2}$ is independently selected from H, $C_{1-6}$ alkyl, $C_{1-4}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkylene, $C_{3-10}$ cycloalkyl-$C_{1-4}$ alkylene, (5-10 membered heteroaryl)-$C_{1-4}$ alkylene, and (4-10 membered heterocycloalkyl)-$C_{1-4}$ alkylene, wherein said $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkylene, $C_{3-10}$ cycloalkyl-$C_{1-4}$ alkylene, (5-10 membered heteroaryl)-$C_{1-4}$ alkylene, and (4-10 membered heterocycloalkyl)-$C_{14}$ alkylene are each optionally substituted with 1, 2, 3, 4, or 5 substituents independently selected from $R^g$;

or any $R^{c1}$ and $R^{d1}$ together with the N atom to which they are attached form a 4-7 membered heterocycloalkyl, which is optionally substituted with 1, 2, or 3 substituents independently selected from $R^g$;

or any $R^{c2}$ and $R^{d2}$ together with the N atom to which they are attached form a 4-7 membered heterocycloalkyl, which is optionally substituted with 1, 2, or 3 substituents independently selected from $R^g$; and each $R^g$ is independently selected from OH, $NO_2$, CN, halo, $C_{1-6}$ alkyl, $C_{2-6}$ alkenyl, $C_{2-6}$ alkynyl, $C_{1-4}$ haloalkyl, $C_{1-6}$ alkoxy, $C_{1-6}$ haloalkoxy, cyano-$C_{1-3}$ alkylene, HO-$C_{1-3}$ alkylene, $C_{6-10}$ aryl, $C_{6-10}$ aryloxy, $C_{3-10}$ cycloalkyl, 5-10 membered heteroaryl, 4-10 membered heterocycloalkyl, $C_{6-10}$ aryl-$C_{1-4}$ alkylene, $C_{3-10}$ cycloalkyl-$C_{1-4}$ alkylene, (5-10 membered heteroaryl)-$C_{1-4}$ alkylene, (4-10 membered heterocycloalkyl)-$C_{1-4}$ alkylene, amino, $C_{1-6}$ alkylamino, di($C_{1-6}$ alkyl)amino, thio, $C_{1-6}$ alkylthio, $C_{1-6}$ alkylsulfinyl, $C_{1-6}$ alkylsulfonyl, carbamyl, $C_{1-6}$ alkylcarbamyl, di($C_{1-6}$ alkyl) carbamyl, carboxy, $C_{1-6}$ alkylcarbonyl, $C_{1-6}$ alkoxycarbonyl, $C_{1-6}$ alkylcarbonylamino, $C_{1-6}$ alkylsulfonylamino, aminosulfonyl, $C_{1-6}$ alkylaminosulfonyl, di($C_{1-6}$ alkyl) aminosulfonyl, aminosulfonylamino, $C_{1-6}$ alkylaminosulfonylamino, di($C_{1-6}$ alkyl)aminosulfonylamino, aminocarbonylamino, $C_{1-6}$ alkylaminocarbonylamino, and di($C_{1-6}$ alkyl)aminocarbonylamino.

2. The compound of claim 1, wherein the compound of Formula (I) has Formula (Ia):

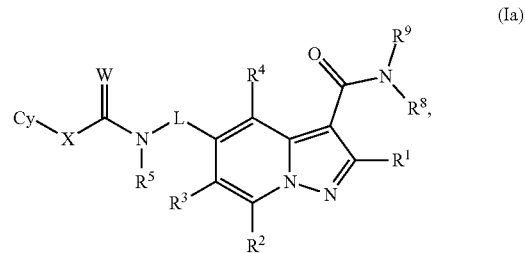

or a pharmaceutically acceptable salt thereof.

3. The compound of claim 2, wherein X is O.
4. The compound of claim 2, wherein X is S.
5. The compound of claim 2, wherein X is NH.
6. The compound of claim 1, wherein the compound of Formula (I) has Formula (Ib):

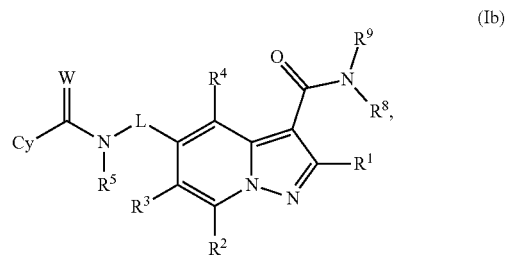

or a pharmaceutically acceptable salt thereof.

7. The compound of claim 1, wherein W is O.
8. The compound of claim 1, wherein W is S.
9. The compound of claim 1, wherein L is $C_{1-6}$ alkylene, which is optionally substituted with 1, 2, or 3 substituents independently selected from OH, $NO_2$, CN, halo, $C_{1-6}$ alkoxy, and $C_{1-6}$ haloalkoxy.
10. The compound of claim 9, wherein L is $C_{1-3}$ alkylene.
11. The compound of claim 1, wherein:
$R^1$, $R^2$, $R^3$, and $R^4$ are each independently selected from H, halo, CN, $NO_2$, $C_{1-6}$ alkyl, $C_{1-6}$ haloalkyl, OH, $C_{1-6}$ alkoxy, $C_{1-6}$ haloalkoxy, $C(O)R^{b1}$, $C(O)NR^{c1}R^{d1}$, $C(O)OR^{a1}$, $NR^{c1}R^{d1}$, and $NR^{c1}C(O)R^{b1}$, wherein said $C_{1-6}$ alkyl is optionally substituted with 1, 2, or 3 substituents independently selected from CN, $NO_2$, OH, $C_{1-6}$ alkoxy, $C(O)R^{b1}$, $C(O)NR^{c1}R^{d1}$, $C(O)OR^{a1}$, $NR^{c1}R^{d1}$, and $NR^{c1}C(O)R^{b1}$;
L is $C_{1-6}$ alkylene, which is optionally substituted with 1, 2, or 3 substituents selected from OH, $NO_2$, CN, halo, $C_{1-6}$ alkoxy, and $C_{1-6}$ haloalkoxy;
$R^5$ is H;
Cy is selected from $C_{6-10}$ aryl and $C_{3-10}$ cycloalkyl, each of which is optionally substituted with 1, 2, or 3 substituents independently selected from $R^{Cy1}$;
$R^8$ is H;
$R^9$ is selected from $C_{1-6}$ alkyl and $Cy^1$, wherein said $C_{1-6}$ alkyl is optionally substituted with 1, 2, or 3 substituents independently selected from $Cy^1$, CN, $NO_2$, $OR^{a1}$, $C(O)R^{b1}$, $C(O)NR^{c1}R^{d1}$, $C(O)OR^{a1}$, $NR^{c1}R^{d1}$, $NR^{c1}C(O)R^{b1}$, $NR^{c1}C(O)OR^{a1}$, $NR^{c1}S(O)_2R^{b1}$, $S(O)_2R^{b1}$, and $S(O)_2NR^{c1}R^{d1}$; or R⁸ and R⁹, together with the N atom to which they are attached, form a 5-10-membered heterocycloalkyl ring, which is optionally substituted with 1, 2, or 3 substituents independently selected from $R^{Cy1}$;

Cy¹ is selected from $C_{6-10}$ aryl, 5-14 membered heteroaryl, and 4-10 membered heterocycloalkyl, each of which is optionally substituted with 1, 2, or 3 substituents independently selected from $R^{Cy1}$;

$R^{Cy1}$ is selected from halo, CN, OH, NO₂, Cy², $C_{1-6}$ alkyl, $C_{1-6}$ haloalkyl, $C_{1-6}$ alkoxy, $C_{1-6}$ haloalkoxy, $C(O)R^{b2}$, $C(O)NR^{c2}R^{d2}$, $C(O)OR^{a2}$, and $NR^{c2}R^{d2}$, wherein said $C_{1-6}$ alkyl is optionally substituted with 1, 2, or 3 substituents independently selected from Cy², halo, CN, OH, NO₂, $C_{1-6}$ haloalkyl, $C_{1-6}$ alkoxy, and $C_{1-6}$ haloalkoxy;

Cy² is selected from $C_{6-10}$ aryl, 5-10 membered heteroaryl, and 4-10 membered heterocycloalkyl, each of which is optionally substituted with 1, 2, or 3 substituents independently selected from $R^{Cy2}$;

$R^{Cy2}$ is selected from halo, CN, NO₂, $C_{1-6}$ alkyl, $C_{1-6}$ haloalkyl, and $OR^{a2}$;

$R^{a1}$, $R^{b1}$, $R^{c1}$, $R^{d1}$, $R^{a2}$, $R^{b2}$, $R^{c2}$, and $R^{d2}$ are each independently selected from H, $C_{1-6}$ alkyl, $C_{1-4}$ haloalkyl, $C_{6-10}$ aryl, $C_{3-10}$ cycloalkyl, 5-10 membered heteroaryl, and 4-10 membered heterocycloalkyl, each of which is optionally substituted with 1, 2, or 3 independently selected $R^g$; and $R^g$ is selected from OH, NO₂, CN, halo, $C_{1-6}$ alkyl, $C_{1-4}$ haloalkyl, $C_{1-6}$ alkoxy, $C_{1-6}$ haloalkoxy, amino, $C_{1-6}$ alkylamino, di($C_{1-6}$ alkyl)amino, carboxy, carbamyl, $C_{1-6}$ alkylcarbonyl, and $C_{1-6}$ alkoxycarbonyl.

12. The compound of claim 11, wherein:
R¹, R², R³, and R⁴ are each independently selected from H, halo, $C_{1-6}$ alkyl, $C_{1-6}$ haloalkyl, $C_{1-6}$ alkoxy, and $C_{1-6}$ haloalkoxy;
L is $C_{1-3}$ alkylene;
R⁹ is selected from $C_{1-6}$ alkyl and Cy¹, wherein said $C_{1-6}$ alkyl is optionally substituted with Cy¹ or $NR^{c1}R^{d1}$, or
$R^{Cy1}$ is selected from halo, Cy², $C_{1-6}$ alkyl, $C(O)R^{b2}$, $C(O)NR^{c2}R^{d2}$, $NR^{c2}R^{d2}$, wherein said $C_{1-6}$ alkyl is optionally substituted with Cy²; and
$R^{Cy2}$ is selected from halo, $C_{1-6}$ alkyl, and OH.

13. The compound of claim 12, wherein
Cy is selected from $C_{6-10}$ aryl and $C_{3-10}$ cycloalkyl, each of which is optionally substituted with 1, 2, or 3 substituents independently selected from halo, $C_{1-6}$ alkyl, and $NR^{c2}R^{d2}$;
R⁸ and R⁹, together with the N atom to which they are attached, form a 5-10-membered heterocycloalkyl ring, which is optionally substituted with 1, 2, or 3 substituents independently selected from Cy², $C_{1-6}$ alkyl, $C(O)R^{b2}$, and $C(O)NR^{c2}R^{d2}$, wherein said $C_{1-6}$ alkyl is optionally substituted with Cy².

14. The compound of claim 13, wherein the compound of Formula (I) has formula:

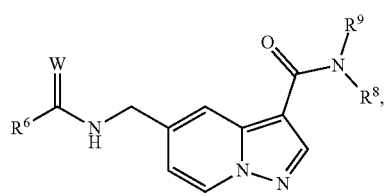

or a pharmaceutically acceptable salt thereof, wherein:
Cy is selected from phenyl and cyclopropyl, each of which is optionally substituted with 1, 2, or 3 substituents independently selected from halo, $C_{1-6}$ alkyl, and $NR^{c2}R^{d2}$;
Cy¹ is selected from phenyl, piperidine, pyridine, and pyrrolidone, each of which is optionally substituted with $C_{1-6}$ alkyl;
R⁸ and R⁹, together with the N atom to which they are attached, form a heterocycloalkyl ring selected from piperidine, piperazine, tetrahydroisoquinoline, and pyrrolidine, each of which is optionally substituted with 1, 2, or 3 substituents independently selected from Cy², $C_{1-6}$ alkyl, $C(O)R^{b2}$, and $C(O)NR^{c2}R^{d2}$, wherein said $C_{1-6}$ alkyl is optionally substituted with Cy²; and
Cy² is selected from phenyl, piperidine, benzoisothiazole, and benzodioxole, each of which is optionally substituted with 1, 2, or 3 independently selected $R^{Cy2}$.

15. The compound of claim 1, wherein the compound of Formula (I) is selected from any one of the following compounds, or a pharmaceutically acceptable salt thereof:

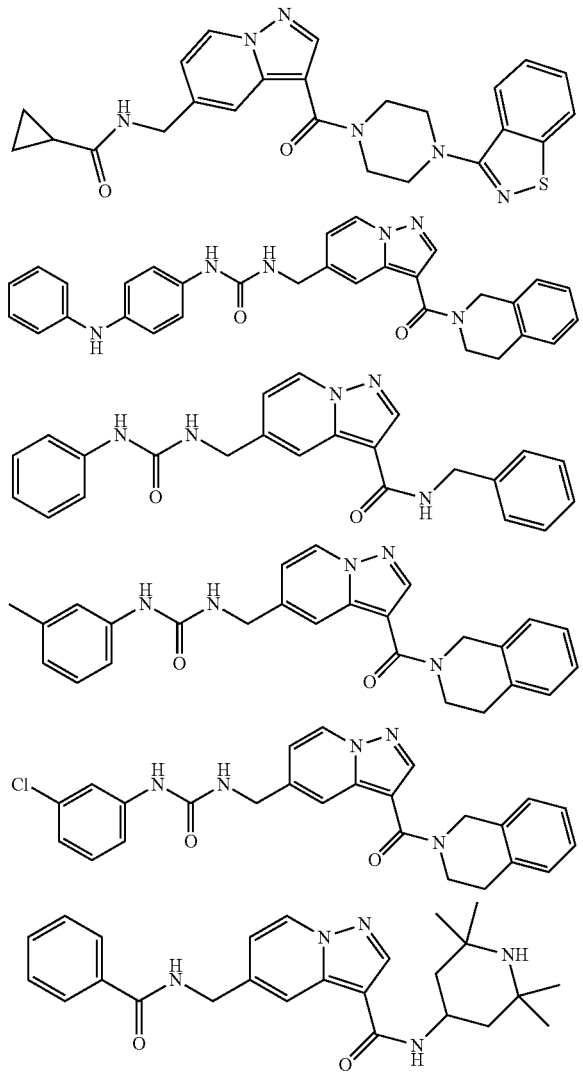

-continued
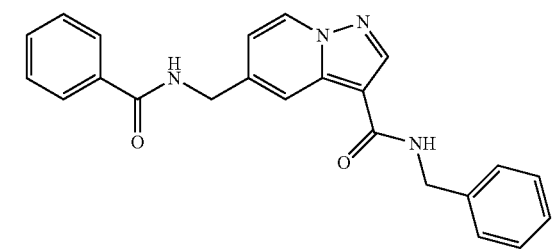
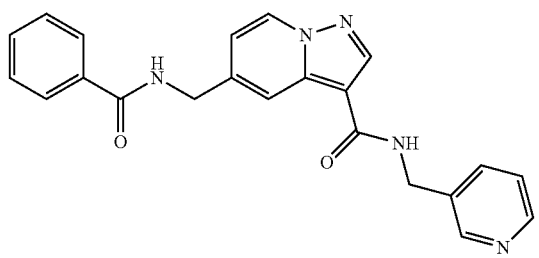
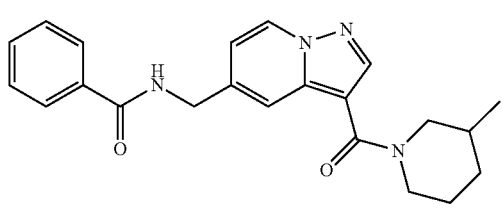
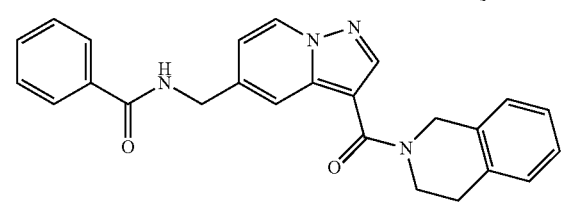
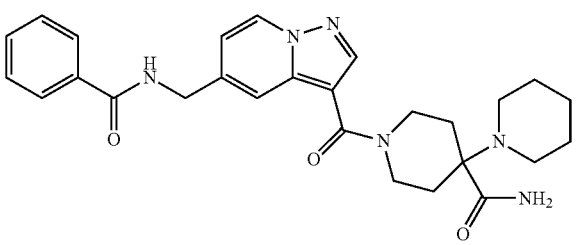
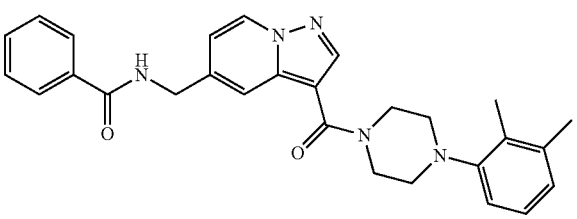
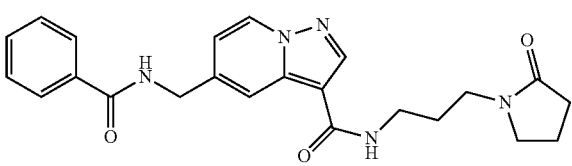
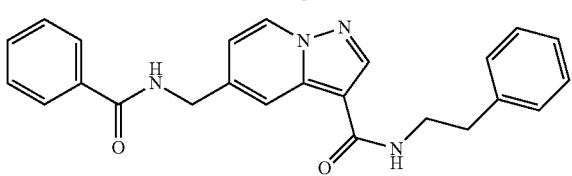
-continued
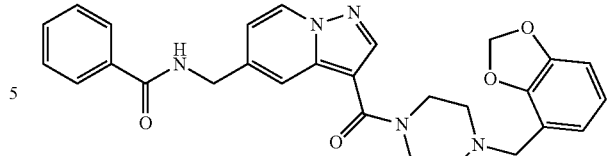
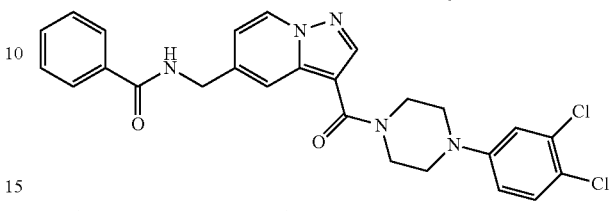
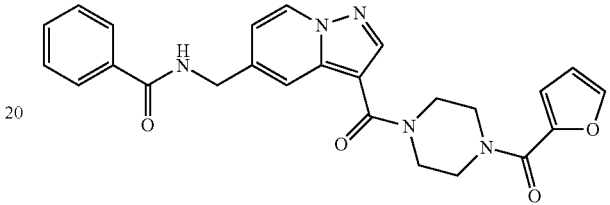
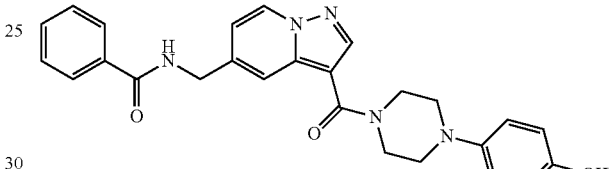
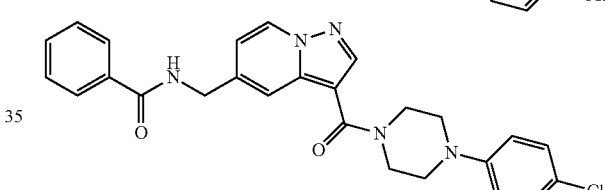
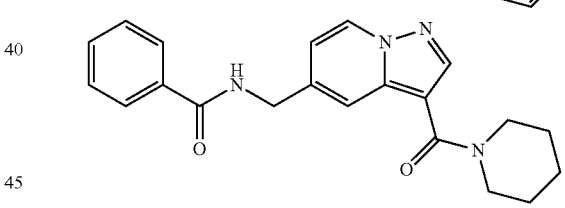
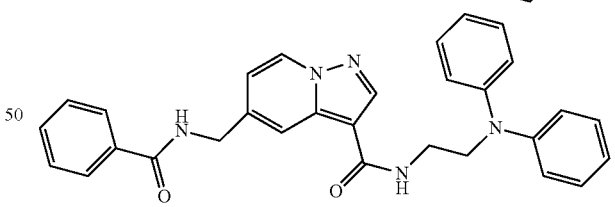
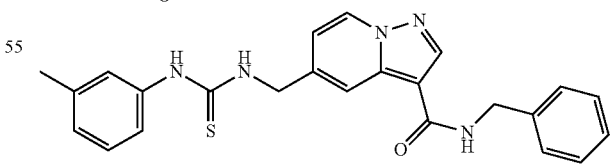
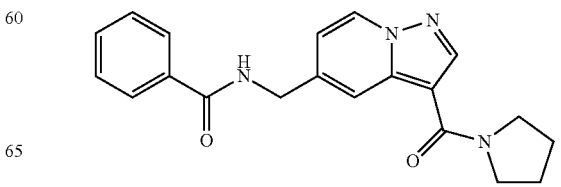

-continued
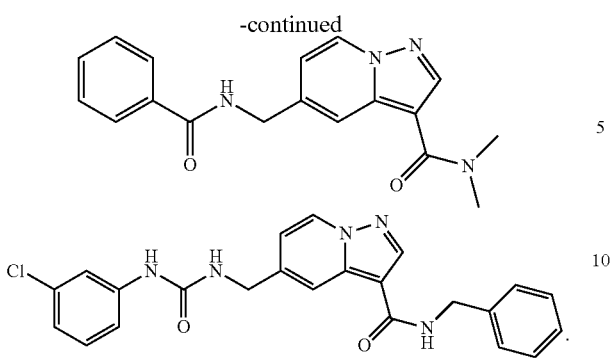
16. A pharmaceutical composition comprising a compound of claim 1, or a pharmaceutically acceptable salt thereof, and a pharmaceutically acceptable carrier.
* * * * *